United States Patent

Neville, Jr. et al.

(10) Patent No.: US 9,364,557 B2
(45) Date of Patent: Jun. 14, 2016

(54) FOLD-BACK DIABODY DIPHTHERIA TOXIN IMMUNOTOXIN AND METHODS OF USE

(75) Inventors: David M. Neville, Jr., Bethesda, MD (US); Jung-Hee Woo, Temple, TX (US); Arthur Frankel, Temple, TX (US)

(73) Assignees: THE UNITED STATES OF AMERICA, AS REPRESENTED BY THE SECRETARY, DEPARTMENT OF HEALTH AND HUMAN SERVICES, Washington, DC (US); SCOTT AND WHITE HEALTHCARE, Temple, TX (US)

( * ) Notice: Subject to any disclaimer, the term of this patent is extended or adjusted under 35 U.S.C. 154(b) by 1499 days.

(21) Appl. No.: 12/671,629

(22) PCT Filed: Aug. 1, 2008

(86) PCT No.: PCT/US2008/009321
§ 371 (c)(1),
(2), (4) Date: Jul. 9, 2010

(87) PCT Pub. No.: WO2009/017823
PCT Pub. Date: Feb. 5, 2009

(65) Prior Publication Data
US 2011/0189209 A1 Aug. 4, 2011

Related U.S. Application Data

(60) Provisional application No. 60/953,416, filed on Aug. 1, 2007.

(51) Int. Cl.
*A61K 39/00* (2006.01)
*C07K 16/00* (2006.01)
*C12P 21/08* (2006.01)
*A61K 38/00* (2006.01)
*A61K 47/48* (2006.01)

(52) U.S. Cl.
CPC ..... *A61K 47/48484* (2013.01); *A61K 47/48561* (2013.01); *A61K 47/48584* (2013.01); *A61K 47/48638* (2013.01); *A61K 47/48676* (2013.01); *A61K 38/00* (2013.01); *A61K 2039/505* (2013.01)

(58) Field of Classification Search
CPC ............ A61K 38/00; A61K 47/48561; A61K 2039/505
See application file for complete search history.

(56) References Cited

U.S. PATENT DOCUMENTS

| 6,103,235 | A | 8/2000 | Neville et al. ............ 424/183.1 |
| 7,192,586 | B2 * | 3/2007 | Bander ....................... 424/155.1 |
| 7,517,527 | B2 | 4/2009 | Neville, Jr. et al. |
| 7,696,338 | B2 | 4/2010 | Neville, Jr. et al. |

| 2004/0213791 | A1 | 10/2004 | Bander et al. ............ 424/155.1 |
| 2005/0079184 | A1 * | 4/2005 | Hsing-Chang et al. .... 424/178.1 |
| 2006/0020258 | A1 | 1/2006 | Strauss et al. ..................... 606/1 |

FOREIGN PATENT DOCUMENTS

| WO | 01/87982 A2 | 11/2001 |
| WO | WO 01/87982 | 11/2001 |
| WO | 2005/012495 A2 | 2/2005 |
| WO | WO 2005/012495 | 2/2005 |
| WO | WO 2005/070456 A2 * | 8/2005 |

OTHER PUBLICATIONS

Thompson et al., Protein Engineering, 2001; 14(12): 1035-1041.*
Ma et al., Bioconjugate Chem., 1997; 8: 695-701.*
Wang et al., Bioconjugate CHem., Mar. 13, 2007; 18: 947-955.*
Vallera et al., Clin. Cancer Res., 2005; 11(10):3879-3888.*
Thompson et al., J. Biol. Chem., 1995; 270(47): 28037-28041.*
Denmeade et al., Cancer Res., 1997; 57(21): 4924-4930.*
Woo et al., Protein Expression and Purification, 2002; 25: 270-282.*
Kim Geun-Bae et al., "A fold-back single-chain diabody format enhances the bioactivity of an anti-monkey CD3 recombinant diphtheria toxin-based immunotoxin", Protein Engineering, Design & Selection: PEDS Sep. 2007, vol. 20, No. 9, pp. 425-432.
Takemura Shin-Ichi et al., "A mutated superantigen SEA D227A fusion diabody specific to MUC1 and CD3 in targeted cancer immunotherapy for bile duct carcinoma", Cancer Immunology, Immunotherapy: CII Mar. 2002, vol. 51, No. 1, pp. 33-44.
Hexham et al., "Influence of relative binding affinity on efficacy in a panel of anti-CD3 scFv immunotoxins," *Mol. Immunol.*, 38:397-408, 2001.
Kim et al., "A fold-back single-chain diabody format enhances the bioactivity of an anti-monkey CD3 recombinant diphtheria toxin-based immunotoxin," *Protein Eng.*, 20:425-32, 2007.
Madshus et al., "Membrane translocation of diphtheria toxin carrying passenger protein domains," *Infect. Immun.*, 60:3296-3302, 1992.
Takemura et al., "A mutated superantigen SEA D227A fusion diabody specific to MUC1 and CD3 in targeted cancer immunotherapy for bile duct carcinoma," *Cancer Imunol. Immunother.*, 51:33-44, 2002.
Thompson et al., "Improved binding of a bivalent single-chain immunotoxin results in increased efficacy for in vivo T-cell depletion," *Protein Eng.*, 14:1035-41, 2001.
Williams et al., Structure/function analysis of interleukin-2-toxin (DAB486-IL-2). Fragment B sequences required for the delivery of fragment A to the cytosol of target cells, *J. Biol. Chem.*, 265:11885-9, 1990.

* cited by examiner

*Primary Examiner* — Gary Nickol
*Assistant Examiner* — Lakia Tongue
(74) *Attorney, Agent, or Firm* — Whitham, Curtis, Christofferson & Cook, P.C.

(57) ABSTRACT

Provided are methods and compositions related to diphtheria toxin diabody immunotoxins.

18 Claims, 17 Drawing Sheets

1. Full-length DTM1-scUCHT1

2. Full-length DTM1-dcUCHT1

3. 483 DTM1-scUCHT1

4. 483 DTM1-dcUCHT1

```
  1 GAGGTCCAAC TGGTACAGTC TGGACCTGAA GTGAAGAAGC CTGGGGCTAC    Vh de J591
    E   V   Q   L    V   Q   S    G   P   E    V   K   K   P    G   A   T       Vh aa-deJ591
    E   V   Q   L    Q   Q   S    G   P   E    L   K   K   P    G   T   S       Vh aa-optimized J591
  1 GAGGTCCAGT TGCAGCAATC TGGACCAGAG TTGAAGAAGC CAGGTACTTC    Vh optimized J591

51 AGTGAAGATA TCCTGCAAGA CTTCTGGATA CACATTCACT GAATATACCA    Vh de J591
    V   K   I    S   C   K   T    S   G   Y    T   F   T    E   Y   T   I       Vh aa-deJ591
    V   R   I    S   C   K   T    S   G   Y    T   F   T    E   Y   T   I       Vh aa-optimized J591
 51 TGTGAGAATT TCTTGTAAGA CTTCTGGTTA CACTTTCACT GAGTACACTA    Vh optimized J591

101 TACACTGGGT GAAGCAGGCC CCTGGAAAGG GCCTTGAGTG GATTGGAAAC    Vh de J591
    H   W   V    K   Q   A    P   G   K   G    L   E   W    I   G   N           Vh aa-deJ591
    H   W   V    K   Q   S    H   G   K   S    L   E   W    I   G   N           Vh aa-optimized J591
101 TTCATTGGGT TAAGCAATCT CATGGTAAGT CTTTGGAGTG GATTGGAAAC    Vh optimized J591

151 ATCAATCCTA ACAATGGTGG TACCACCTAC AATCAGAAGT TCGAGGACAA    Vh de J591
    I   N   P    N   N   G   G    T   T   Y    N   Q   K   F    E   D   K       Vh aa-deJ591
    I   N   P    N   N   G   G    T   T   Y    N   Q   K   F    E   D   K       Vh aa-optimized J591
151 ATCAACCCAA ACAACGGTGG AACTACCTAC AACCAAAAGT TCGAGGATAA    Vh optimized J591

201 GGCCACACTA ACTGTAGACA AGTCCACCGA TACAGCCTAC ATGGAGCTCA    Vh de J591
    A   T   L    T   V   D   K    S   T   D    T   A   Y    M   E   L   S       Vh aa-deJ591
    A   T   L    T   V   D   K    S   S   S    T   A   Y    M   E   L   R       Vh aa-optimized J591
201 GGCTACTTTG ACTGTTGATA AGTCTTCTTC CACTGCTTAC ATGGAATTGA    Vh optimized J591

251 GCAGCCTAAG ATCTGAGGAT ACTGCAGTCT ATTATTGTGC AGCTGGTTGG    Vh de J591
    S   L   R    S   E   D    T   A   V   Y    Y   C   A    A   G   W           Vh aa-deJ591
    S   L   T    S   E   D    S   A   V   Y    Y   C   A    A   G   W           Vh aa-optimized J591
251 GATCCTTGAC CTCTGAGGAT TCCGCTGTCT ACTACTGTGC TGCTGGTTGG    Vh optimized J591

301 AACTTTGACT ACTGGGGCCA AGGGACCCTG CTCACCGTCT CCTCA         Vh de J591
    N   F   D   Y    W   G   Q    G   T   L    L   T   V    S   S               Vh aa-deJ591
    N   F   D   Y    W   G   Q    G   T   T    L   T   V    S   S               Vh aa-optimized J591
301 AACTTCGATT ACTGGGGACA AGGAACCACT TTGACTGTTT CCTCT         Vh optimized J591
```

FIG.20A

```
  1 GACATCCAGA TGACCCAGTC TCCCTCATCC CTGTCCACAT CAGTAGGAGA      VI de J591
    D  I  Q  M  T  Q  S  P  S  S  L  S  T  S  V  G  D          VI aa-deJ591
    D  I  V  M  T  Q  S  H  K  F  M  S  T  S  V  G  D          VI aa-optimized J591
  1 GATATTGTTA TGACTCAATC TCATAAGTTC ATGTCCACTT CGGTGGGTGA      VI optimized J591

51 CAGGGTCACC CTCACCTGTA AGGCCAGTCA AGATGTGGGT ACTGCTGTAG      VI de J591
      R  V  T  L  T  C  K  A  S  Q  D  V  G  T  A  V  D        VI aa-deJ591
      R  V  S  I  I  C  K  A  S  Q  D  V  G  T  A  V  D        VI aa-optimized J591
 51 TAGAGTCTCT ATTATTTGTA AGGCTTCTCA GGACGTGGGT ACTGCTGTTG      VI optimized J591

101 ACTGGTATCA ACAGAAACCA GGACCATCTC CTAAACTACT GATTTATTGG      VI de J591
      W  Y  Q  Q  K  P  G  P  S  P  K  L  L  I  Y  W           VI aa-deJ591
      W  Y  Q  Q  K  P  G  Q  S  P  K  L  L  I  Y  W           VI aa-optimized J591
101 ATTGGTATCA ACAAAAGCCA GGTCAATCTC CAAAGTTGTT GATTTACTGG      VI optimized J591

151 GCATCCACTC GGCACACTGG AATCCCTAGT CGCTTCTCAG GCAGTGGATC      VI de J591
      A  S  T  R  H  T  G  I  P  S  R  F  S  G  S  G  S        VI aa-deJ591
      A  S  T  R  H  T  G  V  P  D  R  F  T  G  S  G  S        VI aa-optimized J591
151 GCTTCTACTA GACATACTGG TGTTCCAGAT AGATTCACTG GTTCTGGTTC      VI optimized J591

201 TGGGACAGAC TTCACTCTCA CCATTTCTAG TCTTCAGCCT GAAGACTTTG      VI de J591
      G  T  D  F  T  L  T  I  S  S  L  Q  P  E  D  F  A        VI aa-deJ591
      G  T  D  F  T  L  T  I  T  N  V  Q  S  E  D  L  A        VI aa-optimized J591
201 TGGTACTGAT TTCACCTTGA CTATCACTAA CGTCCAGTCT GAGGACTTGG      VI optimized J591

251 CAGATTATTA CTGTCAGCAA TATAACAGCT ATCCTCTCAC GTTCGGTCCT      VI de J591
      D  Y  Y  C  Q  Q  Y  N  S  Y  P  L  T  F  G  P           VI aa-deJ591
      D  Y  F  C  Q  Q  Y  N  S  Y  P  L  T  F  G  A           VI aa-optimized J591
251 CTGACTACTT CTGCCAGCAG TACAACTCTT ACCCATTGAC TTTCGGTGCT      VI optimized J591

301 GGGACCAAGG TGGACATCAA A                                     VI de J591
      G  T  K  V  D  I  K                                      VI aa-deJ591
      G  T  M  L  D  L  K                                      VI aa-optimized J591
301 GGAACCATGT TGGATTTGAA G                                     VI optimized J591
```

FIG.20B

FOLD-BACK DIABODY DIPHTHERIA TOXIN IMMUNOTOXIN AND METHODS OF USE

RELATED APPLICATIONS

This application is a 35 U.S.C. §371 U.S. national entry of International Application PCT/US2008/009321 (WO 2009/017823) having an International filing date of Aug. 1, 2008, which claims priority to United States Provisional Application 60/953,416 filed on Aug. 1, 2007, both of which applications are incorporated herein in their entirety by reference.

BACKGROUND OF THE INVENTION

1. Field of the Invention

The present invention relates to an immunotoxin. The invention further relates to a method of treating T cell leukemias or lymphomas, graft-versus-host diseases, cancer, and autoimmune diseases by administering an immunotoxin.

2. Background

Immunotoxins are toxins with altered receptor specificities. The alteration is achieved by coupling a monoclonal antibody (mAb) or growth factor to the toxin or toxin fragment. Plant and bacterial protein toxins intoxicate cells by a multi-step process whereby different toxin domains sequentially interact with cellular components. The intoxication pathway at a minimum consists of surface receptor binding, toxin processing, intracellular routing of toxin A chains to the cytosol, and enzymatic inactivation of protein synthesis (Neville and Hudson (1986) *Ann. Rev. Biochem.* 55:195). The goal of immunotoxin research has been to achieve targeted cell killing comparable to the enormous but indiscriminate cell killing power of the native toxins. An equally important goal has been to maintain the low non-target cell toxicity of toxin A chains, which lack cell receptor binding and membrane translocation functions (Youle and Neville (1982) *J. Clin. Biol.* 257:1598; Neville (1986) in CRC Crit. Rev., Therap. Drug Carrier Syst., CRC Press Inc., 2:329; Immunotoxins, Frankel ed. (1988) Kluwer Academic Publishers). Because of this latter consideration most in vivo clinical studies have focused on A chain immunotoxins or immunotoxins with truncated B chains lacking the receptor binding domain. While some clinical results have been encouraging, the reproducible achievement of both goals is at present uncertain (Program and Abstracts 2nd Int. Symposium on Immunotoxins, June 1990, Lake Buena Vista, Fla.).

Recently, Youle and co-workers have introduced highly efficacious holo-immunotoxins based on diphtheria toxin (DT) binding mutants (Greenfield et al. (1987) Science 238: 536; Johnson et al. (1988) *J. Biol. Chem.* 263:1295; Johnson et al. (1989) *J. Neurosurg.* 70:240). These DT binding site mutants were equal to the wild-type immunotoxins in potency when directed at the human transferrin receptor (TFR) or human CD3, a component of the T cell receptor complex. Since the binding of the mutants was only 1/100-1/1000 of native DT, the toxin receptor appeared to be not needed along the intoxication pathway. This conclusion is limited to immunotoxins which route through CD3 and TFR, because similar immunotoxins directed at CD5 and the high-molecular weight-melanoma-associated antigen are relatively non-toxic (Neville et al. (1989) *J. Biol. Chem.* 264: 14653). On the basis of data obtained with acid-cleavable conjugates which released free DT or the DT binding site mutant CRM9 in acidified endosomes, it was concluded that the DT receptor participates in the optimal intracellular routing of DT and many DT conjugates (Neville et al. (1989) *J. Biol. Chem.* 264:14653). It was also concluded that CD3 and TFR can perform the same routing function as the DT receptor, thus obviating the requirement of a DT receptor interaction for the binding site mutant conjugates anti-CD3-CRM9 and TFR-CRM9 (Intracellular routing of ricin based immunotoxins via the ricin receptor leading to enhanced efficacy has also been reported. Youle et al. (1981) *Cell* 23:551; Marsh and Neville (1986) *Biochem.* 25:4461; Youle and Colombatti (1987) *J. Biol. Chem.* 262:4676). The disadvantages of these chemically conjugated immunotoxins are linkage heterogeneity, Fc receptor interactions and a mutated toxin-binding domain in which binding to DT receptors is reduced but not eliminated. These disadvantages were overcome by developing recombinant immunotoxins based on diphtheria toxin truncated at residue 390 which provided optimal translocation of the toxin A chain into the cytosol while eliminating the toxin binding domain (Williams et al., 1990 and Thompson et al., 2001). These DT based immunotoxins were restricted to having the antibody moiety placed C-terminal to the truncated toxin because antibody domains fused to the N-terminal of the toxin interfered with translocation of biologically active A chain (Madshus et al., 1992 and Hexam et al., 2001).

SUMMARY OF THE INVENTION

The invention is one aspect relates to an immunotoxin comprising a diphtheria toxin moiety and a diabody targeting moiety.

It is a further object of the invention to provide a method of treating cancers such as prostate cancer, breast cancer, and T cell leukemias or lymphomas.

It is a further object of the invention to provide a method of treating autoimmune diseases.

It is a further object of the invention to provide a method of inhibiting graft rejection, inhibiting graft-versus-host disease, and inducing immune tolerance.

Further objects and advantages of the present invention will be clear from the description that follows.

BRIEF DESCRIPTION OF THE DRAWINGS

FIG. 20 shows the optimized variable chain amino acid and DNA sequences for the J591 variable heavy chain (Vh) (A), and J591 variable light chain (Vl) (B). de J591 is deimmunized J591. Characters highlighted in gray color indicate changes of DNA sequence. Vh de J591, Vh aa-deJ591, Vh-optimized, and Vh optimized J591 are SEQ ID NOs:16-19, respectively. Vl de J591, Vl aa-deJ591, Vl-optimized, and Vl optimized J591 are SEQ ID NOs:20-23, respectively.

DETAILED DESCRIPTION OF THE INVENTION

Figure 1A:
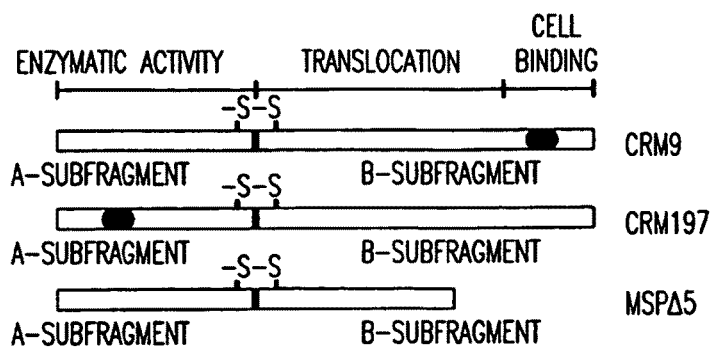
FIG. 1 shows that the epitopes involved in human serum's inhibition of its toxicity lie in the last 150 amino acids of DT. A schematic diagram of the DT mutants CRM9, CRM197 and MSPΔ5 is presented (A). The A- and B-subfragments and their relative size and position are shown. The filled circle represents a point mutation as described in the text. Goat (B) or human (C) serum (human serum was a pool from all samples with positive ELISA for anti-DT antibodies) was incubated with increasing molar concentrations of CRM197 (—O—), MSPΔ5 (—X—) or the B-subfragment (-Δ-) of DT for 30 minutes at room temperature. To this reaction, UCHT1-CRM9 was added to a final concentration of $1 \times 10^{-10}$ M. This mixture was then diluted 10-fold onto Jurkat cells in a protein synthesis inhibition assay as described in the Materials and Methods. Immunotoxin incubated with medium only inhibited protein synthesis to 4% of controls. The results are representative of two independent assays.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then the "less than or equal to 10," as well as "greater than or equal to 10" is also disclosed. It is also understood that throughout the application, data are provided in a number of different formats, and that these data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed, as well as between 10 and 15. It is also understood that each unit between two particular units are also disclosed. For example, if 10 and 15 are disclosed, then 11, 12, 13, and 14 are also disclosed.

Disclosed herein in one aspect are immunotoxins, comprising a mutant diphtheria toxin moiety linked to a targeting moiety, wherein the targeting moiety is a single chain variable region diabody. The immunotoxins disclosed herein in one aspect comprise diabodies. Herein, a "diabody" is a single chain antibody fragment comprising two scFv regions wherein one scFv region associates with a second scFv to form a dimer. Where the first scFv and the second scFv share the same antigen specificity, the diabody is referred to as "bivalent" (also called divalent). Where the first scFv and the second scFv are of different antigen specificities, the diabody is referred to as "bispecific." Thus it is understood and herein contemplated that the diabodies disclosed herein can be bivalent or bispecific.

It is understood and herein contemplated that the disclosed diabodies can act as a targeting moiety for the toxin moiety. Thus, it is disclosed herein that the disclosed diabodies can be specific for any antigen provided translocation of the toxin moiety is still possible. For example, the targeting moiety can be specific for the CD3 molecule on T cells and thus T-cell specific. Also, for example, the targeting moiety can be specific for a cancer antigen including but not limited to PSMA or viral antigen such as, for example, GP120. Thus, disclosed herein are diabodies wherein the diabody comprises the $V_L V_H$ region directed against CD3. Also disclosed are diabodies wherein the $V_L V_H$ region is derived from the anti-CD3 antibody UCHT1 or C207. Further disclosed herein are diabodies wherein the diabody comprises the $V_L V_H$ region directed against PSMA. Also disclosed are diabodies wherein the $V_L V_H$ region is derived from the anti-PSMA antibody J591

The immunotoxin can be a fusion protein produced recombinantly. Derivatives of this immunotoxin are designed and constructed as described herein.

As disclosed above, the toxin moieties of the immunotoxins disclosed herein are mutant diphtheria toxin moieties. It is understood that other toxin moieties such as ricin and pseudomonas exotoxin A (PeA) can be used with the disclosed methods and compositions. It is further understood that the disclosed mutant toxin moieties can comprise substitution mutants. Examples of such substitution mutants include but are not limited to, for example, CRM9. It is also understood that the disclosed mutant toxin moieties can comprise a truncation mutant. The deletion mutants can comprise C-terminal deletions of between 140 and 150 C-terminal amino acids. Thus, disclosed herein are toxin moieties wherein the truncation mutant comprises a deletion of 140, 141, 142, 143, 144, 145, 146, 147, 148, 149, or 150 C-terminal amino acids of the full length diphtheria toxin. Therefore, disclosed herein are immunotoxins wherein the diphtheria toxin is a deletion mutant with 140-150 C-terminal amino acids deleted. It is understood herein that the disclosed truncation mutants can be referred to either by designating the number of deleted C-terminal acids or by designating the number of remaining amino acids counting from the N-terminus. Thus, for example, a diphtheria toxin moiety comprising a deletion of 145 amino acids of the complete diphtheria toxin protein (535 amino acids) can be referred to as DT390. Likewise a deletion of 146 amino acids is DT389. Further examples of alternate naming of truncation mutants are as follows:

140 C-terminal truncation mutant=DT395
141 C-terminal truncation mutant=DT394
142 C-terminal truncation mutant=DT393
143 C-terminal truncation mutant=DT392
144 C-terminal truncation mutant=DT391
147 C-terminal truncation mutant=DT388
148 C-terminal truncation mutant=DT387
149 C-terminal truncation mutant=DT386
150 C-terminal truncation mutant=DT385

The C-terminally truncated toxin moiety retains its toxin function, and membrane translocation function to the cytosol in full amounts. The loss in binding function located in the C terminus of the protein diminishes systemic toxicity by reducing binding to non-target cells. The routing function normally supplied by the toxin binding function is supplied by the receptor bound by the targeting diabody component (e.g., an anti-CD3 diabody). The essential routing pathway is (1) localization to coated pits for endocytosis, (2) escape from lysosomal routing, and (3) return to the plasma membrane. Any receptor bound antibody which can route in this manner will be effective as a diabody for use with the toxin moiety, irrespective of the antigen or epitope to which the antibody is directed. Thus, a wide variety of cell types can in principle be targeted. In practical terms very few receptors fulfill these criteria. When antibodies dissociate from their receptors due to changes in receptor configuration induced in certain receptors as a consequence of endosomal acidification, they enter the lysosomal pathway. This can be prevented or minimized by directing the antibody towards an ecto-domain epitope on the same receptor which is closer to the plasma membranes (Ruud, et al. (1989) Scand. J. Immunol. 29:299; Herz et al. (1990) J. Biol. Chem. 265:21355). Other DT binding site mutants can be used to form derivatives by changing amino acids in the C-terminus which can reduce the binding function as long as the translocation function is maintained. Specific examples are described in the Examples.

Protein toxins of the A-B type have 3 distinct structural and functional domains. (1) an enzymatic domain called the A chain that is highly cytotoxic after transfer or translocation to the cytosol compartment. (2) a translocation domain located within the B chain that facilitates translocation of the a chain into the cytosol; and (3) a receptor binding domain that binds to a cell surface receptor (also in the B chain). The toxin A and B chain is linked by a protease cleavage site spanned by a disulfide bond. This site must be cleaved to achieve translocation into the cytosol compartment and full specific toxicity. Thus an added level of specificity can be built into fusion immunotoxins by replacing cleavage sites that most cells can cleave with cleavage sites that are unique to cancer cells or cancer neovasculature (Liu, S et al., Expert Opinion Biol Ther 3,843-853, 2003). Toxin receptors have several special properties. One property is that they are efficiently endocytosed into endosomal vesicles. A second property is that the toxin receptor routes the toxin along an intracellular pathway to its site of efficient translocation to the cytosol compartment. For diphtheria toxin this site is in the late endosomal compartment. For ricin and pseudomonas exotoxin A this site is along the endoplasmic reticulum/Golgi apparatus.

Immunotoxins are toxins that have been altered by replacing the toxin receptor binding domain with an alternate receptor binding domain chosen to target the toxin to a specific cell type in order to eliminate that cell type. However, in order for the immunotoxin to function efficiently, the new alternate receptor must also route the toxin to its efficient translocation site. The translocation efficiency of diphtheria toxin is 10 to 30-fold greater than that of ricin and pseudomonas exotoxin A, conferring considerable advantage to immunotoxins based on diphtheria toxin. However, the number of receptor types that route diphtheria toxin to the site efficient translocation are very limited, and until recently only 2 examples were known, the CD3ε chain of the T cell receptor complex expressed only on T cells and the transferrin receptor, expressed on all cells but up-regulated with increasing mitotic activity. With the finding herein that a DT-based immunotoxin directed at the prostate specific membrane antigen (PSMA) receptor is highly toxic, a third example has been found.

It is understood that the disclosed immunotoxins can comprise linkers between the toxin moiety and the diabody targeting moiety. It is understood and herein contemplated that any linker known by those of skill in the art can be used to make the disclosed immunotoxins. The choice of which linker to use can be determined by those of skill in the art based on the desired length and flexibility of the linker between each $V_H$ and $V_L$ domain as well as between the toxin and targeting moieties. Thus, it is understood that the linker can be a chemical linker. It is also understood that the linker (L) can be a Gly-Ser linker. The Gly-Ser linker can be but is not limited to (Gly4Ser)n or (Gly3Ser)n. Thus, for example, the linker can be G4S, (G4S)2, (G4S)3, (G4S)4, (G4S)5, (G4S)6, (G4S)7, (G4S)8, (G4S)9, (G4S)10, G3S, (G3S)2, (G3S)3, (G3S)4, (G3S)5, (G3S)6, (G3S)7, (G3S)8, (G3S)9, (G3S)10. It is further understood that the linkers used can be a combination of chemical and gly-ser linkers. For example, the linker between the toxin and the diabody can be a chemical linker and the linker between the diabody domains can be a Gly-Ser linker. It is further understood that the for greater flexibility, a longer linker is used; whereas, a shorter linker is used for application where more rigidity is needed. Typically, the linker between domains of a diabody will be between 3 and 12 amino acids long. More typically, the diabody linker is between 3 and 5 amino acids long. Thus, for example, specifically contemplated are immunotoxins where the linker between the $V_H$ and $V_L$ domains of the targeting diabody moiety are G4S. It is also understood that more than one of the disclosed linkers can be used in a single chain immunotoxin. Thus, for example, specifically contemplated herein are immunotoxins wherein the linker between the toxin moiety and a first $V_L$ of the targeting diabody is G4S, between the first $V_L$ and $V_H$ is G4S, between the first $V_H$ and second $V_L$ is (G4S)3 and between the second $V_L$ and $V_H$ is G4S. Alternatively stated, disclosed herein are immunotoxins where from left to right the immunotoxin comprises:

Toxin-$L_1$-$V_L$-L2-$V_H$-L3-$V_L$-L4-$V_H$; wherein L1, L2, and L4 comprise G4S and L3 comprises (G4S)3.

It is understood and herein contemplated that the disclosed immunotoxins (including fusion proteins and immunoconjugates) can be placed in a pharmaceutically acceptable carrier for administration to a subject. Furthermore, where a chemical linker is used to fuse the toxin and diabody moieties, both acid-cleavable and non-cleavable protein cross-linking reagents can be used in the construction of antibody-diphtheria toxin (Neville et al. (1989) *J. Biol. Chem.* 264:14653-14661); preferred are non-cleavable crosslinkers, such as bis-maleimidohexane and m-maleimidobenzoyl-N-hydroxysuccinimide ester. The synthesis of acid-cleavable protein cross-linking reagents based on orthoester, acetal, and ketal functionalities has been described (Srinivasachar and Neville (1989) *Biochemistry* 28:2501-2509). The unique feature of these functionalities is that their observed hydrolytic rate constants increase 10-fold for each drop in pH, a consequence of specific $H_3O^+$ catalysis leading to a carbonium ion intermediate (Cordes and Bull (1974) *Chem. Rev.* 74:581-603). Moreover, these functionalities are resistant to base catalysis permitting manipulation and storage at alkaline pH. The cross-linking reagents react with proteins via heterobifunctional groups (maleimide and N-hydroxysuccinimide ester) or homobifunctional groups (bis-maleimide). The maleimide cross-linking is accomplished by prior protein thiolation with iminothiolane. Cross-linked proteins exhibit first-order dissociation under acid conditions. The $t_{1/2}$ at pH 5.5 varies between 0.1 and 130 h for a series of six different cleavable cross-linkers (Srinivasachar and Neville (1989) *Biochemistry* 28:2501-2509).

Also disclosed herein, the disclosed diabodies can be formed in a "fold-back" formation. Such formation typically occurs through the use of rigid linkers from 3 to 12, more typically from 3 to 5 amino acids long such as the G4S linker. The Toxin-L1-$V_L$-L2-$V_H$-L3-$V_L$-L4-$V_H$; wherein L1, L2, and L4 comprise G4S and L3 comprises (G4S)3 is an example of a fold-back diabody immunotoxin. Therefore, disclosed herein are immunotoxin fusion proteins comprising a diphtheria toxin moiety and a targeting moiety, wherein the targeting moiety is a diabody, wherein the sequence from the amino terminus from left to right is toxin moiety, $L_1$, $V_{L1}$, $L_2$, $V_{H1}$, $L_3$, $V_{L2}$, $L_4$, $V_{H2}$, wherein the toxin moiety comprises a truncation mutation, $L_1$, $L_2$, and $L_4$ are (G4S) linkers, and $V_L$ and $V_H$ are the variable light and heavy domains. Also disclosed herein are immunotoxin fusion proteins comprising a diphtheria toxin moiety and a targeting moiety, wherein the targeting moiety is a diabody, wherein the sequence from the amino terminus from left to right is toxin moiety, $L_1$, $V_{L1}$, $L_3$, $V_{L2}$, $L_4$, $V_{H2}$, wherein the toxin moiety comprises a truncation mutation, $L_1$, $L_2$, and $L_4$ are (G4S) linkers, and $V_L$ and $V_H$ are the variable light and heavy domains, wherein $V_{L1}$ and $V_{H1}$ can be the same as $V_{L2}$ and $V_{H2}$.

Also disclosed herein are fold-back diabodies comprising toxin moieties wherein the truncation mutant comprises a deletion of 140, 141, 142, 143, 144, 145, 146, 147, 148, 149, or 150 C-terminal amino acids of the full length diphtheria toxin. Also disclosed herein are diphtheria toxin immunotoxins comprising a truncation mutant and a fold-back diabody specific for an antigen or cell surface determinant such as CD3 or PSMA. Also disclosed herein are diphtheria toxin immunotoxins comprising a truncation mutant and a fold-back diabody specific for an antigen or cell surface determinant such as CD3 or PSMA, wherein the $V_L$ and $V_H$ regions of the diabody are the $V_L$ and $V_H$ regions of an anti-CD3 or anti-PSMA antibody, respectively. For example, diabodies described herein have the $V_L$ and $V_H$ regions originating from the anti-CD3 antibodies UCHT1 and C207, and the anti-PSMA antibody J591, and the resulting immunotoxins are A-dmDT390scfbDb(UCHT1), A-dmDT390scfbDb(C207), and A-dmDT390scfbDb(J591), respectively. Thus, for example disclosed herein is A-dmDT390scfbDb(C207)

wherein C207 is an anti-CD3 diabody affinity matured mutant of FN18 (wherein din indicates a deletion mutant and scfbDb indicates a single chain fold-back diabody). Also disclosed herein are A-dmDT390scfbDb(C207) immunotoxins wherein the furin site amino acid sequence cleavage site RVRRSV has been replaced with the MMP cleavage site GPLGMLSQ or the PSA cleavage site HSSKLQ. Also disclosed herein, for example, is A-dmDT390scfbDb(UCHT1) wherein UCHT1 is an anti-CD3 diabody clone. Also disclosed herein, for example, is A-dmDT390scfbDb(J591) wherein J591 is an anti-PSMA diabody clone. Additional examples of immunotoxins disclosed herein include but are not limited to A-dmDT395scfbDb(J591); A-dmDT394scfbDb(J591); A-dmDT393scfbDb(J591); A-dmDT392scfbDb(J591); A-dmDT391scfbDb(J591); A-dmDT389scfbDb(J591); A-dmDT388scfbDb(J591); A-dmDT387scfbDb(J591); A-dmDT386scfbDb(J591); A-dmDT385scfbDb(J591); A-dmDT395scfbDb(anti-PSMA); A-dmDT394scfbDb(anti-PSMA); A-dmDT393scfbDb(anti-PSMA); A-dmDT392scfbDb(anti-PSMA); A-dmDT391scfbDb(anti-PSMA); A-dmDT389scfbDb(anti-PSMA); A-dmDT388scfbDb(anti-PSMA); A-dmDT387scfbDb(anti-PSMA); A-dmDT386scfbDb(anti-PSMA); A-dmDT385scfbDb(anti-PSMA); A-dmDT395scfbDb(UCHT1); A-dmDT394scfbDb(UCHT1); A-dmDT393scfbDb(UCHT1); A-dmDT392scfbDb(UCHT1); A-dmDT391scfbDb(UCHT1); A-dmDT389scfbDb(UCHT1); A-dmDT388scfbDb(UCHT1); A-dmDT387scfbDb(UCHT1); A-dmDT386scfbDb(UCHT1); A-dmDT385scfbDb(UCHT1); A-dmDT395scfbDb(C207); A-dmDT394scfbDb(C207); A-dmDT393scfbDb(C207); A-dmDT392scfbDb(C207); A-dmDT391scfbDb(C207); A-dmDT389scfbDb(C207); A-dmDT388scfbDb(C207); A-dmDT387scfbDb(C207); A-dmDT386scfbDb(C207); A-dmDT385scfbDb(C207); A-dmDT395scfbDb(anti-CD3); A-dmDT394scfbDb(anti-CD3); A-dmDT393scfbDb(anti-CD3); A-dmDT392scfbDb(anti-CD3); A-dmDT391scfbDb(anti-CD3); A-dmDT389scfbDb(anti-CD3); A-dmDT388scfbDb(anti-CD3); A-dmDT387scfbDb(anti-CD3); A-dmDT386scfbDb(anti-CD3); A-dmDT385scfbDb(anti-CD3).

It is herein contemplated that the disclosed immunotoxins can be produced recombinantly as fusion proteins.

Also are disclosed herein fold-back diabody immunotoxins formed with A-dmDT390scfbDb(J591) or its derivatives in which the amino acids of the furin protease cleavage RVRRSV (SEQ ID NO: 24) that begins at residue 191 from the amino terminus is replaced by a matrix metalloprotease cleavage site GPLGMLSQ (SEQ ID NO: 25, Liu, S et al., Expert Opinion Biol Ther 3,843-853, 2003) or a prostatic specific antigen cleavage site HSSKLQ (SEQ ID NO: 26, Denmeade S R et al., Cancer Research 57, 4924-30, 1997) accomplished by PCR mutagenesis. These fold-back immunotoxins have higher specificity towards cancers permitting higher doses in vivo.

Although many workers express immunotoxins in *E. coli* and refold these immunotoxins from solubilized solid *E. coli* granules, this technology is only applicable to simple antibody domains such as single chain scFv. In order to express biscFv domains and fold-back diabody domains the refolding machinery present in eukaryote endoplasmic reticulum is needed. The yeast, *P. pastoris*, has this machinery. The use of toxin-resistant eukaryotic cells can overcome the immunotoxin toxicity. However, selection and characterization of toxin-resistant eukaryotic cells are tedious, labor intensive and time-consuming work. Furthermore, the bivalent immunotoxin production in a EF-2 mutant CHO cell expression system was limited to 5 mg/L and could not be increased by selection for multiple gene insertions. Due to this limitation, with three exceptions (12, 20, 25) all recombinant immunotoxin production for therapeutic uses has been limited to *E. coli* production necessitating denaturation and refolding from inclusion bodies (6). However, refolding of the multi-domain structure of the bivalent immunotoxin from *E. coli* was inefficient and full bioactivity was not recovered (25). Also, the multi-domain structure of the bivalent immunotoxin hinders efficient production in *Escherichia coli*. Therefore, the attempt to develop a robust *Pichia pastoris* production system for the bivalent or bispecific immunotoxin was driven by the inadequacy of the existing productions systems.

*Pichia pastoris* is a good expression system for the bivalent and bispecific immunotoxins disclosed herein. For example, *Pichia* was good for the bivalent anti-T cell immunotoxin A-dmDT390-bisFv as it provides optimal protein folding compared to prokaryotic expression systems and provides higher yields compared to mammalian cell expression (CHO cells). Antibody fusion proteins require correct disulfide bridges and the endoplasmic reticulum of yeast provides an oxidizing environment like that of eukaryotic antibody producing cells. The multi-domain structure of the bivalent or bispecific immunotoxin requires a eukaryotic expression system to properly fold this complex protein. Yet most eukaryotes are sensitive to the effects of protein synthesis inhibition upon expression of the immunotoxin. However, a budding yeast, *Pichia pastoris* has a certain degree of tolerance to DT (Neville et al., 1992; Woo et al., 2002) and yielded the immunotoxin at a level of 40 mg/L in fermentor culture. The immunotoxin was produced by fermentation of genetically engineered *Pichia pastoris* (JW102, renamed from pJHW#2 (Woo et al., 2002)) via the secretory route. As shown in Example 41, the present method provides a yield of 120 mg/l after a 163 h induction period and the purified yield is 90.8 mg/L.

After gene optimization to reduce the AT content of the DNA sequence, secreted expression levels under the AOX1 promoter of 25-30 mg/L can be obtained in bioreactors after 24-44 hours of induction. *Pichia pastoris* was sensitive to the toxic effects of cytosolic expressed diphtheria toxin A chain which ADP ribosylates elongation factor 2 (EF-2) leading to cessation of protein synthesis. Toxicity to expression of A-dmDT390-bisFv by the secretory route was indicated by a continuous fall in methanol consumption after induction. A mixed feed of glycerol and methanol was provided to the cells. Expression of the catalytic domain (A chain) of DT in the cytosol is lethal to *Pichia pastoris*. When cells bearing the construct A-dmDT390-BisFv (UCHT1) were induced by methanol to express the immunotoxin, nearly 50% were killed after 24 hours (Woo et al., 2002). In contrast, when the same immunotoxin was expressed in CHO cells that had been mutated to DT resistance, no toxic effect was observed (Liu, et al., 2000; Thompson, et al., 2001). In the cytosol of eukaryotes, the catalytic domain of DT catalyzes ADP ribosylation of elongation factor 2 (EF-2), leading to inhibition of protein synthesis and cell death (by protein starvation and or apoptosis, Van Ness et al., 1980; Houchins, 2000). The sensitivity of the eukaryotic EF-2 to ADP-ribosylation by these toxins lies in the structure of protein. EF-2 is a single polypeptide chain of about 850 amino acids and is composed of two domains. The N-terminal G domain is responsible for binding and hydrolysis of GTP that promotes translation, and the C-terminal R (or diphthamide) domain is thought to interact with the ribosome (Kohno et al., 1986; Perentesis et al., 1992). The diphthamide domain contains a histidine residue in a region of 22 residues that are well conserved in the EF-2 of all eukaryotes. This conserved histidine is specifically modified post-translationally to the derivative, diphthamide, which is the unique target for ADP-ribosylation by DT (Van Ness et al., 1880). In *S. cerevisiae*, the conserved histidine can be mutated and substitutions with some other 2 amino acids yielded functional EF-2s that were resistant to ADP-ribosylation (Phan et al., 1993; Kimata and Kohno 1994). However, cells with EF-2 mutated at diphthamide grew more slowly than those expressing wild-type EF-2. In CHO cells, a single substitution of arginine for glycine, which is another well conserved residue located at the 3rd position to the C-terminal side of the diphthamide, also prevented the formation of diphthamide (Kohno & Uchida, 1987; Foley et al., 1992) and resulted in non-ADP-ribosylatable EF-2. This mutation had the same effect on EF-2 of *S. cerevisiae* (Kimata et al., 1993). In contrast to the mutation at diphthamide, the Gly to Arg mutation in EF-2 did not affect cell growth of CHO and *S. cerevisiae* (Foley et al., 1992; Kimata and Kohno 1994; Kimata et al., 1993).

In order to determine if the expression level of the immuntoxins disclosed herein including for example the diphtheria toxin diabody immunotoxins and diphterhia toxin bivalent antibody immunotoxins disclosed herein such as A-dmDT390-scfbDb and A-dmDT390-bisFv could be further increased by rendering *Pichia pastoris* insensitive to toxin, the EF-2 gene of *Pichia pastoris* has been mutated so that the Gly at position 701 was changed to Arg, which has been shown to prevent ADP-ribosylation of EF-2 in other organisms. The EF-2 mutagenesis required cloning of the gene, introduction of the in vitro mutated sequence with a selection marker, URA3, to the genome and PCR identification of mutated clones. The entire EF-2 gene of *Pichia pastoris* has been cloned and sequenced. The coding sequence of *Pichia pastoris* EF-2 is 2526 nucleotides coding for 842 amino acids. The *Pichia pastoris* EF-2 is the same as the EF-2 of *S. cerevisiae* and *S. pombe* in length and shares 88% and 78% of identity in amino acid sequence with these two, respectively. In contrast to these two yeasts, *Pichia pastoris* has only one copy of the EF-2 gene that contains a short intron. Before the complete sequence of EF-2 was known, different approaches were used to mutate *Pichia pastoris* to obtain DT resistant strains. All these efforts were unsuccessful due to the lack of robust selection. Based on the EF-2 sequence obtained, a pBLURA-Δ5' mutEF-2 was constructed that targets the *Pichia pastoris* EF-2 gene and introduces a mutation of Gly 701 to Arg in the gene by homologous recombination. The construct contains the 3' end 1028 nucleotides of EF-2 that has been mutagenized in vitro to contain the amino acid substitution and the auxotrophic marker URA3. A PCR detection method was also developed for fast and accurate identification of mutant clones after uracil selection. The targeted mutation strategy with construct pBLURA-Δ5' mutEF-2 allowed mutation of the EF-2 gene of *Pichia pastoris* with about 40% of uracil positive clones being found to contain the introduced mutations. EF-2 mutants were developed with different auxotrophic markers, (specifically mutEF2JC308 (ade1 arg4 h is 4), mutEF2JC303 (arg4 his4) and mutEF2JC307 (his4)) and demonstrated that the Gly 701 to Arg mutation in EF-2 confers resistance to the cytosolic expression of DT A chain.

When EF-2 mutants were used to express A-dmDT390-bisFv under the control of AOX1 promoter, they did not show the advantage over the non-mutated expressing strain JW102 in the production of the protein in shake-flask. However, in large-scale fermentation culture under conditions adopted from those optimal for JW102, the production of the mutant strain YYL#8-2 [mutEF2JC307-8(2)], increased continuously for 96 hours and reached a level 1.46-fold greater than the non-mutated JW102 strain. Cell growth and methanol consumption rates of the mutant strain expressing A-dmDT390-bisFv were the same as that of the non-expressing wild type strain. Therefore it appeared that expression of A-dmDT390-bisFv was not toxic to the mutant strain. The EF-2 mutants allowed expression of A-dmDT390-bisFv under the control of the constitutive GAP promoter ($P_{GAP}$). In shake-flask culture, the production of A-dmDT390-bisFv under $P_{GAP}$ was about 30% higher than that under $P_{AOX1}$. The increase in production under $P_{GAP}$ may be more significant in fermentation cultures since fermentation allows cells to grow to very high density.

In the *Pichia pastoris* expression system, most heterologous proteins such as botulinum neurotoxin fragments for vaccine use (Potter et al., 2000), hepatitis B surface antigen (Hardy et al., 2000), gelatin (Werten et al., 1999), collagen (Nokelainen et al., 2001), and insulin (Wang et al., 2001) were successfully expressed and/or secreted by using a simple defined medium. The cytosolic expression of the catalytic domain of DT causes protein synthesis inhibition, leading to complete cell death in the defined medium, but not in complex media (Liu et al., 2003). This finding indicates that complex media play a role in attenuation of protein synthesis inhibition that is caused by ADP-ribosylation of EF-2. A very low production of the bivalent immunotoxin was observed in the defined medium but not in a complex medium in shake flask culture. Fermentation of *Pichia pastoris* for expression of heterologous proteins had been developed on the basis of a defined medium but use of complex media for expression of the bivalent immunotoxin in a secreted form provides a higher level of production.

In the present large scale production of bivalent or bispecific immunotoxins in *Pichia pastoris*, lowering the induction temperature to 15° C. substantially improved the secretion of bioactive immunotoxin, and thereby compensated for the limitation in *Pichia pastoris* secretory capacity. In addition, the use of complex medium containing yeast extract further enhanced immunotoxin secretion, apparently by attenuating the toxic effects of the immunotoxin on the *Pichia pastoris* host.

The expression level of an exemplary bivalent or bispecific immunotoxin was improved by 4-fold in bioreactor culture compared to shake flask culture by optimizing the fermentation conditions in *Pichia pastoris* as follows: (1) use of Soytone Peptone and yeast extract based complex medium, (2) use of methanol/glycerol mixed feed (4:1) to supplement the energy source during methanol induction, (3) continuous feeding of PMSF and yeast extract during induction, and (4) lowering temperature to 15° C. during methanol induction. The lowered temperature resulted in a 2-fold increase in secretion relative to using 23° C. during methanol induction.

As noted above, a major problem in production of the bivalent immunotoxin was reduction of methanol utilization during the methanol induction phase. The reduction of methanol utilization results from a reduction in the activity of the rate limiting enzyme, alcohol oxidase (AOX1). This could be secondary to protein synthesis inhibition by the bivalent immunotoxin reaching the cytosol compartment through leakage from the secretory compartment or by proton dependent translocation from the mildly acidic secretory compartment (Arata et al., 2002). The fact that methanol utilization is not affected by immunotoxin production in a *Pichia pastoris* strain mutated to toxin resistance in the EF-2 gene (Liu et al., 2003) indicates that toxin induced ADP-ribosylation is the cause of the decreased AOX1 activity in strain JW102. However, control of AOX1 level is balanced by both synthesis as well as degradation, and degradative mechanisms could be augmented in response to toxin mediated ADP-ribosylation. For reasons unknown, yeast extract increased methanol utilization, though not to wild type levels. In addition, low methanol utilization negatively affected *Pichia pastoris* cell growth. This was corrected in the present method by adding another carbon source, glycerol, and continuous feeding of yeast extract during methanol induction. These two corrections raised the methanol consumption to 80% of the non-expressing strain.

To further compensate for *Pichia pastoris* protein synthesis inhibition by the expressed immunotoxin, the fermentation conditions were manipulated for full activation of alcohol oxidase I (AOX1), the rate limiting enzyme for methanol metabolism (Veenhuis et al., 1983). Since the immunotoxin gene was under the control of the same strong promoter as the AOX1 gene, the immunotoxin should be highly expressed. However, it has previously been observed in the secretion of heterologous proteins that each protein appears to have an optimal secretion level. Expression beyond the optimal level (overexpression) of secreted heterologous proteins can cause a reduction in secreted protein yields in mammalian, insects and yeast cells (Bannister and Wittrup, 2000; Liebman et al., 1999; Liu et al., 2003; Pendse et al., 1992). In order to determine whether the bivalent immunotoxin was being overexpressed in *Pichia pastoris*, the induction temperature was lowered during methanol induction. Since most cellular activities including protein synthesis are decreased at low temperature, lowering induction temperature should decrease the synthetic rate of the bivalent immunotoxin. Any resulting change in secretion rate was judged. Bivalent immunotoxin expression was increased at low induction temperatures, reaching a maximum at 17.5° C., and secretion of bioactive immunotoxin reached a maximum at 15° C., in spite of the fact that methanol consumption rate at 15° C. fell to 75% of its 23° C. value. Because continuous feeding of PMSF and yeast extract during induction effectively inhibited protease activity in supernatants, it appears unlikely that a reduction in protease activity with lower induction temperature accounts for the nearly 2-fold increase in bivalent immunotoxin secretion seen at 15° C. The limitation in *Pichia pastoris* secretion of bivalent immunotoxin previously described may actually represent an overexpression at 23° C. that is reduced at 15° C. achieving a better balance of input and output within the secretory compartment.

In short, the immunotoxin was produced in *Pichia pastoris* (JW102) via the secretory route under control of the AOX1 promoter in the fermentor using methanol as a carbon source. There were two major impediments to efficient immunotoxin production, the toxicity of the immunotoxin towards *Pichia pastoris* and the limited secretory capacity of *Pichia pastoris* for the immunotoxin. The toxicity towards *Pichia pastoris* resulted in a decrease in the metabolic rate of methanol consumption, a cell growth rate reduction and very low productivity in a defined medium during methanol induction. These problems were overcome by (1) using an enzymatic digest of soy protein (e.g., Soytone peptone) and yeast extract based complex medium, (2) using methanol/glycerol mixed feed (4:1) to supplement energy source during methanol induction, and (3) continuously feeding PMSF and yeast extract during methanol induction. Lowering the induction temperature to 15° C. improved secreted immunotoxin yield by almost 2-fold, up to 40 mg/L (at 67 hours induction) compared to secretion at an induction temperature of 23° C., even though methanol consumption was reduced. In addition, with the use of the present method, the fraction of immunotoxin present as biologically inactive oligomeric forms was decreased. In addition further improvements in fold-back diabody immunotoxins are possible by engineering extra copies of proteins into *Pichia pastoris* (JW102) that are involved in overcoming degradation of heterologous proteins by the manifestations of the unfolded protein response.

In a method of producing immunotoxin, the method can comprise methods of enhancing codon preference that are known and exemplified.

It is understood that any of the disclosed immunotoxins are useful for the treatment of various conditions or diseases. Therefore, disclosed herein in one aspect are methods of treating a cancer in a subject comprising administering to the subject an immunotoxin or a derivative thereof, under conditions such that the cancer is treated. Further disclosed herein are methods of treating a cancer in a subject comprising administering to the subject an immunotoxin that is a truncation mutant, wherein the truncation mutant comprises a deletion of 140, 141, 142, 143, 144, 145, 146, 147, 148, 149, or 150 C-terminal amino acids of the full length diphtheria toxin. Also disclosed are methods wherein the diabody is an anti-PSMA diabody such as, for example, a diabody wherein the diabody comprises the $V_L V_H$ regions of J591. PSMA or prostate specific membrane antigen is a transmembrane antigen expressed on prostate cells and highly over-expressed in prostate tumors. It is weakly expressed on some other tissues and is considered highly tissue specific and thus is considered a prime target for immunotoxin mediated therapy of prostatic cancer (Fracasso, G et al., *The Prostate* 53, 9-23, 2002 and Huang, X et al., *The Prostate* 61, 1-11, 2005). In addition, PSMA is over-expressed on the neovasculature that feeds a variety of human primary cancers and their metastatic counterparts such as breast, lung and kidney (Milowsy, M I et al., *J. Clin Oncol* 25,540-47,2007). PSMA is a homodimer with a 2-fold axis of symmetry. Thus a divalent anti-PSMA diabody immunotoxin with binding sites oriented 180 degrees apart is ideally suited to complex PSMA. PSMA is a functional glutamate carboxylase metalloprotease. It is an analog of the transferrin receptor (Davis, M I et al., *PNAS* 102, 5981-86, 2005) that has been previously shown to route DT-based immunotoxins to the site of efficient translocation to the cytosol compartment. As disclosed herein, it is understood that the toxin moiety can be a truncation mutant such as, for example, DT395, DT394, DT393, DT392, DT391, DT390, DT389, DT388, DT387, DT386, and DT385. Thus, for example disclosed herein are methods of treating a cancer in a subject wherein the immunotoxin that is administered to the subject is A-dmDT390scfbDb(J591); A-dmDT389scfbDb (J591); A-dmDT380scfbDb(J591); A-dmDT395scfbDb (J591), or any other DT truncation mutant J591 fold-back diabody combination. It is understood that the disclosed methods of treating a cancer have utility for treating any cancer where PSMA is expressed on cancerous tissue, such as, for example, prostate cancer or in a cancer where PSMA is expressed in the neovasculature, breast cancer, lung cancer, and renal cancer.

It is further contemplated that any cancer with a targetable antigen can be treated with the disclosed methods providing that the targeted epitope routes DT to its efficient translocation site. For example, the cancer can comprise a T-cell leukemia. Thus disclosed herein are methods of treating T cell leukemias or lymphomas in an animal comprising administering to the animal one of the disclosed diphtheria toxin diabody immunotoxins, or derivatives thereof, under conditions such that the T cell leukemias or lymphomas are treated. It is understood and herein contemplated that the immunotoxin for treating a T cell leukemia can comprise a diabody wherein the diabody is an anti-CD3 diabody. It is further understood that any anti-CD3 diabody can be used in the disclosed methods. Thus, for example, the diabody can comprise the VLVH regions of UCHT1. It is further contemplated that any of the disclosed anti-CD3 diabodies can be used with any of the disclosed toxin moieties including, for example, DT390, DT389, DT395, DT394, DT393, DT392, DT391, DT388, DT387, DT386, and DT385. Thus, for example, the immunotoxin can comprise A-dmDT390scfbDb(UCHT1) or A-dmDT390scfbDb(C207).

"Treatment," "treat," or "treating" mean a method of reducing the effects of a disease or condition. Treatment can also refer to a method of reducing the disease or condition itself rather than just the symptoms. The treatment can be any reduction from native levels and can be, but is not limited to, the complete ablation of the disease, condition, or the symptoms of the disease or condition. Therefore, in the disclosed methods, treatment" can refer to a 10%, 20%, 30%, 40%, 50%, 60%, 70%, 80%, 90%, or 100% reduction in the severity of an established disease or the disease progression. For example, a disclosed method for reducing the effects of prostate cancer is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition, but an improvement in the outlook of a disease or condition.

The compositions and immunotoxins disclosed herein are useful in transplantation related conditions and disease such as graft versus host disease, graft rejection, and the induction of immune tolerance. The role of T cells in the aforementioned transplantation related diseases and conditions makes the CD3 molecule (i.e., the T cell receptor), which is only present on T cells, a viable target for the action of the disclosed immunotoxins. Therefore, disclosed herein are methods of treating graft-versus-host disease in an animal, comprising administering to the animal an immunotoxin disclosed herein, or derivatives thereof under conditions such that the graft-versus-host disease is treated. In particular disclosed herein are methods of treating graft versus host disease wherein the immunotoxin is an anti-CD3 diphtheria toxin immunotoxin. It is understood that any anti-CD3 antibody derived diabody such as a diabody derived from UCHT1, C207, or FN18 can be used in the methods disclosed herein. It is further contemplated that any of the disclosed anti-CD3 diabodies can be used with any of the disclosed toxin moieties including, for example, DT390, DT389, DT395, DT394, DT393, DT392, DT391, DT388, DT387, DT386; and DT385. Thus, for example, the immunotoxin can comprise A-dmDT390scfbDb(UCHT1) or A-dmDT390scfbDb(C207).

Also disclosed are methods of inducing immune tolerance to a graft in a recipient, comprising: a) administering to the recipient an anti-CD3 immunotoxin disclosed herein, thereby reducing the recipient's T-cell population; and b) administering to the recipient an agent that inhibits dendritic cell maturation. It is understood that any anti-CD3 antibody derived diabody such as a diabody derived from UCHT1, C207, or FN18 can be used in the methods disclosed herein. It is further contemplated that any of the disclosed anti-CD3 diabodies can be used with any of the disclosed toxin moieties including, for example, DT390, DT389, DT395, DT394, DT393, DT392, DT391, DT388, DT387, DT386; and DT385. Thus, for example, the immunotoxin can comprise A-dmDT390scfbDb(UCHT1) or A-dmDT390scfbDb(C207).

Also disclosed herein are methods of inhibiting a rejection response in a primate recipient to a foreign mammalian graft comprising the steps of a) administering to the recipient an anti-CD3-DT immunotoxin, wherein the immunotoxin comprises scfbDb-DT, so as to reduce the recipient's T-cell lymphocyte population by at least 80%, as compared to the recipient's T-cell lymphocyte population prior to administration of the immunotoxin; and b) transplanting the graft into the recipient, such that a rejection response by the recipient to the graft is inhibited. It is understood that any anti-CD3 antibody derived diabody such as a diabody derived from UCHT1, C207, or FN18 can be used in the methods disclosed herein. It is further contemplated that any of the disclosed anti-CD3 diabodies can be used with any of the disclosed toxin moieties including, for example, DT390, DT389, DT395, DT394, DT393, DT392, DT391, DT388, DT387, DT386; and DT385. Thus, for example, the immunotoxin can comprise A-dmDT390scfbDb(UCHT1) or A-dmDT390scfbDb(C207).

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

It is contemplated herein that the disclosed methods of treating graft-versus-host disease, inducing immune tolerance to a graft, and inhibiting a rejection response can be complemented by the use of an immunosuppressive agent in addition to the methods already disclosed. It is understood and herein contemplated that the immunotoxin for treating graft-versus-host disease can comprise a diabody wherein the diabody is an anti-CD3 diabody. It is further understood that any anti-CD3 diabody can be used in the disclosed methods. Thus, for example, the diabody can comprise the VLVH regions of UCHT1. It is further contemplated that any of the disclosed anti-CD3 diabodies can be used with any of the disclosed toxin moieties including, for example, DT390, DT389, DT395, DT394, DT393, DT392, DT391, DT388, DT387, DT386, and DT385. Thus, for example, the immunotoxin can comprise A-dmDT390scfbDb(UCHT1) or A-dmDT390scfbDb(C207). Therefore, disclosed herein are methods of treating graft-versus-host disease, inducing immune tolerance to a graft, and inhibiting a rejection response, further comprising administering an immunosuppressive agent. Examples of suitable immunosuppressive agents include but are not limited to cyclosporine, rapamycin, and mycophenolate mofetil and the anti-B cell antibody (anti-CD20) rituximab. It is further contemplated that the disclosed immunosuppressive agent can be an agent that inhibits dendritic cell maturation. Such action can occur, for example through the inhibition of nuclear translocation, such as, inhibition of nuclear translocation of NFκB. Thus, for example disclosed herein are methods of treating graft-versus-host disease, inducing immune tolerance to a graft, and inhibiting a rejection response further comprising an immunosuppressive agent wherein the immunosuppressive agent is an agent that inhibits dendritic cell maturation is an inhibitor of nuclear translocation of NFκB. Specifically contemplated herein are immunosuppressive agents that are inhibitors of dendritic cell maturation that are inhibitors of nuclear translocation of NFκB such as, for example, deoxyspergualin and analogs or derivatives of deoxyspergualin including, for example, methyl-deoxyspergualin or a deoxyspergualin analog lacking a chiral center (e.g., LF 08-0299) (Andoins et al., 1996, which is incorporated herein by reference). Other derivatives or analogs of deoxyspergualin can be used that include, for example, those identified in U.S. Pat. Nos. 4,518,532; 4,518,532; 4,525,299; 4,956,504; 5,162,581; 5,476,870; 5,637,613; W.O. 96/24579; EP 600762; EP 669316; EP 7433000; EP 765866; and EP 755380, which are incorporated herein by reference. Also disclosed are inhibitors of dendritic cell maturation that are inhibitor of nuclear translocation of NFκB such as the proteosome inhibitor bortezomib. Also disclosed are methods wherein immunosuppressive agents that inhibit dendritic cell maturation wherein the agent that inhibits dendritic cell maturation activates one or more NF-AT dependent Th2 cytokines. Also disclosed are methods wherein the immunosuppressive agents that inhibit dendritic cell maturation wherein the agent that inhibits dendritic cell maturation inhibits one or more NFκB dependent Th1 cytokines. It is further contemplated that the disclosed immunosuppressive agent that is an inhibitor of dendritic cell maturation can function through other means. Therefore, disclosed herein are methods of treating graft-versus-host disease, inducing immune tolerance to a graft, and inhibiting a rejection response wherein the inhibitor of dendritic cell maturation is a soluble IL-17 receptor Fc fusion protein; a glucocorticoid; blocker of tumor necrosis factor alpha binding; blocker of granulocyte macrophage colony stimulating factor binding; blocker of IL-12p70 binding; blocker of IL-1β binding; and/or an anti-CD154 ligand.

It is understood that one of skill in the art will be able to determine the optimal time to administer the immunosuppressive agent. Such administration can occur 24 hours before transplantation. In particular, administration can occur 0 to 12 hours before transplantation. Further contemplated are methods wherein the immunosuppressant is administered beginning from about 0 to 6 hours before the transplantation. The immunosuppressive agent can be administered to the recipient as well as the donor. Specifically contemplated herein are methods wherein the agent that inhibits dendritic cell maturation is administered to the recipient at least once. Also disclosed herein are methods comprising administering to a transplant donor, prior to harvesting the transplant, an agent that inhibits dendritic cell maturation.

It is understood herein that the graft used in the methods disclosed herein can comprises donor cells, tissue or organ. It is further contemplated that the donor cells, tissue, or organ is selected from the group consisting of kidney, liver, heart, pancreas, lung, skin, and isolated cell transplants of pancreatic islets, hepatocytes, stem cell, and differentiated precursors cells. It is understood and herein contemplated that the donor graft (tissue, cell, or organ) can be from an allogeneic, syngeneic, or xenogeneic donor. It is further contemplated that the donor source can be a cadaver.

In another embodiment, the present invention relates to a pharmaceutical composition comprising a diabody-DT mutant in an amount effective to treat T cell leukemias or lymphomas, which carry the CD3 epitope, graft-versus-host disease or autoimmune diseases, or treat a cancer such as prostate cancer or breast cancer which carries PSMA and a pharmaceutically acceptable diluent, carrier, or excipient. One skilled in the art will appreciate that the amounts to be administered for any particular treatment protocol can readily be determined. Suitable amounts might be expected to fall within the range of 0.1 to 0.25 mg (toxin content) per kg of body weight.

Thus, one embodiment of the invention provides a method of treating an autoimmune disease in an animal comprising administering to the animal an immunotoxin comprising a mutant diphtheria toxin moiety and an antibody moiety which routes by the anti-CD3 pathway, or derivatives thereof, under conditions such that the autoimmune disease is treated. It is understood and herein contemplated that in a T cell mediated autoimmune disease, because the immune response is T cell mediated, eliminating or inducing tolerance in the autoreactive T cells will treat the autoimmune disease. Stated another way, by reducing the number of or inducing tolerance in the T cells responsible for the autoimmune disease through the use of the immunotoxins disclosed herein, the autoimmune disease will be treated. Any of the immunotoxins described herein can be used. It is understood and herein contemplated that the immunotoxin for treating an autoimmune disease can comprise a diabody wherein the diabody is an anti-CD3 diabody. It is further understood that any anti-CD3 diabody can be used in the disclosed methods. Thus, for example, the diabody can comprise the VLVH regions of UCHT1. It is further contemplated that any of the disclosed anti-CD3 diabodies can be used with any of the disclosed toxin moieties including, for example, DT390, DT389, DT395, DT394, DT393, DT392, DT391, DT388, DT387, DT386, and DT385. Thus, for example, the immunotoxin can comprise A-dmDT390scfbDb(UCHT1) or A-dmDT390scfbDb (C207).

Also disclosed are methods for treating acquired immunodeficiency syndrome in an animal, comprising administering to the animal an immunotoxin comprising a diphtheria toxin binding mutant moiety and an antibody moiety which routes by the anti-CD3 pathway, or derivatives thereof under conditions such that the acquired immunodeficiency syndrome is treated. Alternatively, a method of treating acquired immunodeficiency syndrome in an animal, comprising administering to the animal a non-toxic mutant of diphtheria toxin followed by an antibody-diphtheria toxin immunotoxin which routes by the anti-CD3 pathway or derivatives thereof under conditions such that the acquired immunodeficiency syndrome is treated is provided. It is understood that any anti-CD3 antibody derived diabody such as a diabody derived from UCHT1, C207, or FN18 can be used in the methods disclosed herein. It is further contemplated that any of the disclosed anti-CD3 diabodies can be used with any of the disclosed toxin moieties including, for example, DT390, DT389, DT395, DT394, DT393, DT392, DT391, DT388, DT387, and DT386. Thus, for example, the immunotoxin can comprise A-dmDT390scfbDb(UCHT1) or A-dmDT390scfbDb(C207).

The present invention will be illustrated in further detail in the following non-limiting examples.

EXAMPLE 1

Cell Depletion in Rhesus Monkeys Induced by FN18-CRM9 FN18-CRM9 Conjugate

Conjugation of anti-Vβ and anti-VαIgG monoclonal antibodies to CRM9 is performed by the same methods used to conjugate anti-CD3 to CRM9 using a non-cleavable linker such as bismaleimidohexane and previously described in detail (Neville et al. (1988) *J. Biol. Chem.* 264:14653-61). The monoclonal antibody FN18 is the monkey equivalent of the human anti-CD3 (UCHT1) and is known to bind the same CD3 receptor epitopes (ε and γ) as bound by the human CD3 antibody and is the same isotype as the human CD3 antibody. Thus, in terms of the parameters relevant for predicting successful T cell depletion, the present CD3-CRM9 conjugate and FN18-CRM9 are expected to have the same activity.

Administration

Conjugates can be administered as an I.V. bolus in a carrier consisting of 0.1M $Na_2SO_4$+0.01M phosphate buffer, pH 7.4 plus 1 part in 50 of serum previously obtained from the subject. The dose schedule is every other or third day for 3 to 6 days. The total dose is preferably from 25 to 200 micrograms of toxin per kg of body weight.

The actual dose of FN18-CRM9 used was equal to 0.167 of the minimum lethal dose (MLD) in guinea pigs. Since the estimation of the MLD was performed in an animal lacking an immunotoxin target cell population (guinea pigs), the true MLD of FN18-CRM9 and anti-CD3-CRM9 is expected to be higher in monkeys and humans than in guinea pigs.

T Cell Kill

Helper T cell (CD4+ cells) numbers in peripheral blood fell dramatically after the initial administration of FN18-CRM9 in two rhesus monkeys. T cell counts began to rise by day 4 (sampled just prior to the second dose of FN18-CRM9). On day 5 in monkey 8629, CD4+ cells were depressed below the limit of detection (<50 cells/$mm^3$). Cells remained below or equal to 200/$mm^3$ out to day 21. This low level of CD4+ cells is associated with profound immunodeficiency in humans and in monkeys (Nooij and Jonker (1987) *Eur. J. Immunol.* 17:1089-1093). The remarkable feature of this study is the long duration of helper T cell depletion (day 21) with respect to the last administration of immunotoxin (day 4) since intravenously administered immunotoxins were cleared from the vascular system with half-lives <9 hours (Rostain-Capaillon and Casellas (1990) Cancer Research 50:2909-2916), the effect outlasting circulating immunotoxin. This is in contrast to T cell depletion induced by Unconjugated anti-CD3 antibodies (Nooij and Jonker (1987) *Eur. J. Immunol.* 17:1089-1093).

In monkey 1WS the second dose of conjugate only appeared to result in a diminished rate of CD4+ cell recovery. However, CD4+ cells were still fewer than normal at day 21. The blunted response of monkey 1WS to the second dose of immunotoxin was found to be due to a preexisting immunization of this animal to the toxin. Monkey 1WS had a significant pre-treatment anti-diphtheria toxin titer as revealed by a Western blot assay. This titer was markedly increased at day 5, indicative of a classic secondary response. In contrast, monkey 8629 had no detectable pre-treatment titer and only a trace titer by day 5 and a moderate titer by day 28.

The specificity of FN18-CRM9 toward T cells can be seen by comparing the total white blood cell (WBC) count in the same two monkeys. WBCs fell, but only to 45% of baseline value on day 2 compared to 6% of baseline values for the CD4+ T cell subset. Most of the fall in WBC values can be accounted for by the T cell component of the WBC population (~40%). However, B cells are initially depleted after FN18-CRM9 although these cells recover more quickly. FN18 is an IgG, isotype and as such is known to bind to $Fc_{11}$ receptors present on B cells and macrophages with low affinity. The FN18-CRM9 depletion of B cells indicates that significant interactions between the Fc portion of the FN18 antibody and B cells is taking place.

The peripheral T cell depletion induced by unconjugated FN18 at a dose known to produce immunosuppression 0.2 mg/kg/day (Nooij and Jonker (1987) *Eur. J. Immunol.* 17:1089-1093) was compared to the immunotoxin FN18-CRM9 administered at ⅙th the FN18 dose. Peripheral CD4+ T cell depletion is more pronounced and more long-lasting with the conjugate. The demonstration that FN18-CRM9 reduces the peripheral helper T cell subset (CD4+) to levels less than or equal to 200 cell/$mm^3$ for a period as long as 21 days demonstrates that this immunotoxin and its anti-human analogs are effective immunosuppressive reagents.

The demonstration that FN18-CRM9 is a potent agent for inducing T cell depletion in non-human primates demonstrates that an anti-human homolog of FN18-CRM9, UCHT1-CRM9 (Oxoid USA, Charlotte, N.C.) for example, is a potent agent for inducing T cell depletion in humans.

The Fc binding region of anti-TCR/CD3 monoclonals may or may not be needed to induce T cell depletion when the anti-TCR/CD3 monoclonals are conjugated to CRM9. The $Fc_{11}$ binding regions can be removed, for example, by forming the conjugates with $F(ab')_2$ derivatives as is indicated in the literature (Thorpe et al. (1985) *J. Nat'l. Cancer Inst.* 75:151-159). In addition, anti-TCR/CD3 IgA switch variants such as monoclonal antibody T3.A may be used (Ponticelli et al. (1990) *Transplantation* 50:889-892). These avoid rapid vascular clearance characteristic of $F(ab')_2$ immunotoxins. $F(ab')_2$ and IgA switch variants of anti-TCR/CD3-CRM9 immunotoxins are therefore derivative anti-TCR/CD3 immunotoxins. These derivatives will avoid the B cell interaction noted and can increase specificity. However, $IgG_{2a}$ switch variants will maximize T cell activation through the $Fc_1$, receptor and may be useful in certain situations where T cell activation aids immunotoxin induced toxicity.

General methods to make antibodies lacking the Fc region or to make antibodies which are humanized are set forth in Harlow and Lane, Antibodies: A Laboratory Manual, Cold Spring Harbor Laboratory, Cold Spring Harbor, N.Y., 1988. Thus, as used in the claims, antibody can mean the entire antibody or any portion of the antibody sufficient for specific antigen or receptor binding.

EXAMPLE 2

Treatment of Autoimmune Diseases Using Other Antibody-CRM9 Conjugates which Route by the Anti-CD3 Pathway Since receptor recycling is a requirement for effective CRM9 based immunotoxins and since TCR/CD3 recycles as a unit, antibodies directed at other epitopes on TCR/CD3 will constitute effective derivatives, in particular antibodies directed at the approximately 50 Vβ subset families or the approximately equal number of Vα subsets can be used to conjugate CRM9 and ablate specific Vβ or Vα subsets in vivo. In addition, in some cases it will be desirable to develop specific monoclonal antibodies reacting with unique rearrangements of either the Vα or Vβ subset families.

The advantage of targeting the specific Vβ or Vα subset(s) as opposed to the entire T cell population is twofold: (1) Elimination of a Vβ subset does not create a generalized immunodeficiency, only a hole in the immune repertoire is generated. Therefore, the ability to ward off most infections and maintain immune surveillance of most malignant transformations would remain intact. (2) Immunotoxin log kill increases linearly as the target cell burden decreases, assuming dose is unchanged. A 50-fold increase in log kill can be obtained as the target is changed from the entire set of T cells to a single Vβ subset. However, due to (1) the high affinity of binding of these immunotoxins, (2) the very low total dose given which is below target cell receptor saturation and (3) the irreversible nature of the endocytotic process, the target cells deplete the effective dose and this depletion decreases as target burden decreases. Since the log kill is exponential in effective dose, much higher increases in log kill than 50-fold on changing the target from T cells to a Vβ subset can occur. The expected increase in log kill will only occur if the immunotoxin is specific for the defined target. Extraneous interactions with other cell types via the antibody Fc piece is preferably eliminated.

Because HIV has been shown to preferentially infect one ($V\beta_{12}$) or a few of the 20 $V\beta$ subset families providing a small T cell reservoir of HIV replication, and because HIV infection apparently involves an unknown superantigen, CRM9 based immunotoxins directed at these specific $V\beta$ subsets such as anti-$V\beta_{12}$-CRM9 can reduce the HIV virus load. In addition, total ablation of a $V\beta$ subset in the presence of an endogenous superantigen can lead to long-term ablation of the subset since maturing T cells are negatively selected in the presence of endogenous superantigens. Since the specific $V\beta$ subset responding to the superantigen is eliminated, infection cannot take place.

The two strategies that can be utilized for using anti-$V\beta_{12}$-CRM9 immunotoxins to treat HIV infections are (1) treatment depleting the susceptible $V\beta$ subset to an extent where continued infection cannot be maintained and (2) treatment to the extent that all or nearly all of the $V\beta_{12}$ subset is eradicated.

Anti-human $V\beta$ monoclonal antibodies such as S5-11 (anti-$V\beta_{12}$) are available (T Cell Sciences, Cambridge, Mass.) and can be conjugated to CRM9 by standard methodologies.

Briefly, as in Example 5, conjugation of anti-$V\beta$ and anti-V$\alpha$IgG monoclonal antibodies to CRM9 is performed by the same methods used to conjugate anti-CD3 to CRM9 using a non-cleavable linker such as bismaleimidohexase and previously described in detail (Neville et al. (1988) *J. of Biol. Chem.* 264:14653-61).

Conjugates can be administered as an I.V. bolus in a carrier consisting of 0.1M $Na_2SO_4$+0.01M phosphate buffer, pH 7.4 plus 1 part in 50 of serum previously obtained from the patient. The dose schedule is every other or third day for 3 to 6 days. The total dose is preferably from 25 to 200 micrograms of toxin per kg of body weight, but may be increased if anti-diphtheria toxin antibodies are present in the patient's sera in significant amounts.

Other $V\beta$ or $V\alpha$ subsets which may be found to be associated with HIV infection can be treated in the same manner described herein by conjugating the CRM9 to the antibody specifically reactive with the appropriate $V\beta$ or $V\alpha$ subset.

EXAMPLE 3

T Cell Depletion and Immunosuppression in Monkeys Using the Immunotoxin Anti-CD3-CRM9

CRM9 is a diphtheria toxin (DT) binding site mutant and forms the basis of the anti-T cell immunotoxin anti-CD3-CRM9. This immunotoxin has been constructed against human and rhesus T cells and has shown above to kill 3 logs of human T cells in a nude mouse xenograft system. The present example demonstrates a 2 log kill of T cells in rhesus monkey lymph nodes that is also shown to produce prolongation of skin allograft rejection in monkeys.

Humans are immunized against diphtheria toxin by exposure to DPT vaccines in childhood. This long lasting immunity may interfere with the efficacy of DT based immunotoxins. Many monkeys are immunized against DT by natural exposure to toxin producing *Corynebacterium*. The present method addresses any potential interference of pre-existing DT antibodies with the activity of the present immunotoxins.
ELISA ELISA assays were performed in order to determine the levels of anti-DT titers existing in 9 individuals in a population ages 27 to 55. There were 3 individuals with titers of 1:100 (low) and 6 with titers of 1:1000 (moderate).

Rhesus monkeys were screened by the same assay and a 1:1000 titered monkey was selected.
Administration of Non-Toxic Diphtheria Toxin Mutant Monkeys were treated by I.V. route 5 min prior to the immunotoxin dose with a 100 fold excess of CRM197 over the CRM9 content of the immunotoxin to be administered. Just prior to administering CRM197, a H1 histamine blocking agent such as Benadryl or Tagevil was given I.V. to minimize any possibility of an anaphylactic reaction (for Benadryl 4 mg/kg). No histaminic reaction was detected.

Anti-CD3-CRM9 was given at a total dose between 0.1 and 0.2 mg/kg (toxin weight) in 3 equally divided doses (approximately 0.033 mg/kg) on 3 consecutive days. In these monkeys, the total dose of immunotoxin was 0.1 mg/kg.

A comparison of the efficacy of anti-CD3-CRM9 in monkeys was conducted by comparing the decrease in the lymph node T/B cell ratio (a measure of lymph node T cell depletion) and the immunosuppressive effect of the immunotoxin as judged by prolongation of mismatched skin graft survival. Effects on the survival of skin grafts is a clear indicator of the general effect a given treatment has on the subject's immune system.

The monkey with the preexisting anti-DT titer that was pretreated with CRM197 shows the same level of T/B cell inversion as in the negative titered monkey. Skin graft survival was significantly prolonged over the titered monkey treated without CRM197. The failure to achieve a prolongation of graft survival equal to the negatively titered monkey is likely due to the lower weight of this monkey which causes T cells to repopulate faster, in this case 3-4 days faster, due to the larger thymic T cell precursor pool in younger animals. Age related effects such as these can be compensated for by modification of dosage levels and timing of administration.

EXAMPLE 4

Immunotoxin UCHT1-CRM9 for the Treatment of Steroid Resistant Graft-Versus-Host Disease Treatment protocols for this type of disease can be expected to last a year, with Patients being followed for at least 5 years.
Characterization of UCHT1-CRM9 and CRM197

UCHT1-CRM9 is a covalent 1:1 conjugate of anti-human CD3 IgG1 monoclonal antibody and CRM9. The conjugate is synthesized, purified, sterile filtered and assayed for concentration, biological efficacy toward target cells and non-target cell toxicity by standardized culture assays. The method of synthesis, purification assay are identical to that used for FN18-CRM9 which was used in the pre-clinical monkey studies described in Examples 5-7.

CRM9 and CRM197 are produced by the Biotechnology Unit, NIH and purified by the Cooperating Facility. UCHT1 is produced in mouse ascites fluid and is purified by affinity chromatography over Protein A Sepharose. The synthesis, purification and storage of UCHT1-CRM9 is performed in a dedicated secure area. UCHT1-CRM9 is purified in 2 mg lots which are pooled and stored at 4° C. Shelf life is documented to be five months at full biological potency but does not exceed 4 months for this study. Preferably, most of the immunotoxin is used within 3 months of synthesis.
Patient Population The patient population consists of individuals suffering from steroid resistant GVHD whose prognosis is poor. Patients are assayed for anti-CRM9 (anti-DT) titers and antibodies to murine immunoglobulin. Patients having anti-CRM9 titers of 1:1000 and below are treated according to the present protocol. Patients who have a history of receiving murine immunoglobulins or who exhibit positive anti-Ig titers may require special consideration.

Dosage of CRM9 Immunotoxin and Non-Toxic Mutant

UCHT1-CRM9 is administered at a dose which is 1/10 or less of the estimated minimum lethal dose (MLD) in a T lymphopenic patient. The MLD is expected to be at least 0.15 mg/kg (CRM9 content) based on the MLD of 0.15 mg/kg of IgG1-CRM9 in guinea pigs which lack a target cell population for the IgG1. (The presence of target cells in humans raises the MLD by providing a sink for the immunotoxin.) The optimal dose schedule has been found in monkeys to be administration on 3 consecutive days in 3 equally divided doses, and this schedule can be used throughout the treatment period. This permits administration of the total dose before any rise in pre-existing antitoxin titers due to a secondary response. In addition, the initial repopulation from the thymus is also eliminated, thus, further lowering the total T lymphocyte pool. Therefore, a total of 0.0125 mg/kg in three equally divided doses is given to the patient. This dose does induces T cell depletion in monkeys so that monitoring of T cell subsets and signs and symptoms of GVHD is relevant at the lowest dose. For the administration of this dose patients with anti-CRM9 titers of 1:100 or less will be treated. This permits pretreatment doses of CRM197 at 0.33 mg/kg or 1/10 the dose easily tolerated in monkeys. A second dosage group can include patients selected for antitoxin titers of 1:330 or less to whom CRM197 will be given at 1.0 mg/kg. A third dosage group can include patients with 1:1000 antitoxin titers or less will be given CRM197 at 3.3 mg/kg, a dose expected to be tolerable in humans, because it is easily tolerated by monkeys (see Example 7). The monkey MLD data should be very similar to humans on a per weight basis. However, GVHD patients are expected to be more like guinea pigs, because they have a smaller target cell population compared to non-GVHD patients.

Dose escalation can be tested by increasing the dose by a factor of 1.5. Table 1 exemplifies such a dose escalation test. For example three patients are used in each dosage group. There is a 3 to 4 week delay between each patient so that any late toxicity is detected before a dosage group is completed:

TABLE 1

| Patient # | CRM9 Dose each day mg/kg | Total Dose Mg/kg | Week ending |
| --- | --- | --- | --- |
| 1, 2, 3 | 0.00417 | 0.0125 | 12 |
| 4, 5, 6 | 0.00636 | 0.019 | 24 |
| 7, 8, 9 | 0.0083 | 0.028 | 36 |
| 10, 11, 12 | 0.0125 | 0.042 | 48 |

Assuming each patient weighs on the average 70 kg, the first dosage group will consume 2.6 mg of the CRM9 immunotoxin, and will be supplied as a pool of two 2 mg batches. The second group will consume 3.9 mg and will also be supplied as 2 pooled batches. The third group will require 5.9 mg and will be supplied as three pooled batches. The fourth group will require 8.9 mg and will be supplied as three pooled batches and an additional two pooled batches.

Administration

Prior to administering CRM197 a H1 histamine blocking agent such as Benadryl or Tagevil is given I.V. to minimize any possibility of an anaphylactic reaction (for Benadryl 4 mg/kg). The CRM197 is administered I.V. in a 5 mg/ml sterile filtered solution in phosphate buffered saline pH 7.4 (PBS) over a 5 min time period. The immunotoxin is then given I.V. at 0.2 mg/ml over 2 min time period in a sterile filtered solution of 0.90 mM sodium sulfate and 10 mM sodium phosphate pH 7.4.

Measurements of Biological Parameters

The following parameters can be measured at various intervals during treatment (as exemplified by the schedule below):

A Cytokines, TNF alpha, gamma IFN, IL-6

B Routine clinical chemistries

C WBC, Hct, diff; lymphocyte subsets CD3, CD4, CD8, CD2, CD16, CD20

D Body Weight

E Immune function assays. ELISA assays of serum to monitor antibody responses to UCHT1 (primary response) and CRM9 (secondary response). ELISA assays to monitor antibody responses to polio and DPT reimmunizations done at 1 year following bone marrow transplantation.

| | | |
|---|---|---|
| (before IT) Day 0 | A, B, C, D, E | Also A 2 hrs post |
| Day 1 | A, C, D | |
| Day 2 | A, C, D | |
| Day 3 | A, B, C, D | |
| Day 4 | C, D | |
| Day 7 | A, C, D | |
| Day 10 | B, C | |
| Day 14 | A, C, D | |
| Day 21 | C, D | |
| Day 28 | A, B, C, D, E | |
| Day 45 | C, D | |
| Day 60, | B, C, D, E | |

EXAMPLE 5

An Anti-CD3 Single-Chain Immunotoxin with a Truncated Diphtheria Toxin Avoids Inhibition by Pre-Existing Antibodies in Human Blood The present Example examines the effect of human serum with pre-existing anti-DT antibodies on the toxicity of UCHT1-CRM9, an immunotoxin directed against CD3 molecules on T-lymphocytes. Sera with detectable anti-DT antibodies at 1:100 or greater dilutions inhibited the immunotoxin toxicity. Experiments with radiolabeled-UCHT1-CRM9 indicate that anti-DT antibodies partially block its binding to the cell surface as well as inhibit the translocation from the endosome to the cytosol. The inhibitory effect could be adsorbed using a full-length DT mutant or B-subfragment. A C-terminal truncation mutant could not adsorb the inhibitory effect, suggesting that the last 150 amino acids contain the epitope(s) recognized by the inhibitory antibodies.

Therefore, an anti-CD3 single-chain immunotoxin, sFv-DT390, was made with a truncated DT. The $IC_{50}$ of sFv-DT390 was $4.8\times10^{-11}$ M, 1/16 the potency of the divalent UCHT1-CRM9. More importantly, sFv-DT390 toxicity was only slightly affected by the anti-DT antibodies in human sera. "sFv" and "scUCHT1" both are singe chain antibodies containing the variable region.

Mutated full-length and truncated diphtheria toxin (DT) molecules are used for making immunotoxins. These immunotoxins show strong cytotoxic effects to their target cells, and some of them have already been used in clinical trials (1-7).] Previously, an immunotoxin directed against the CD3ε molecule of the T-cell receptor complex, a pan T-cell marker was constructed. This construct is made with a monoclonal antibody of mouse-origin, UCHT1, and a binding site mutant of diphtheria toxin (DT), CRM9 (8). The immunotoxin, UCHT1-CRM9, is capable of regressing established xenografted human T-cell (Jurkat) tumors in nude mice (9). A rhesus monkey analog of UCHT1-CRM9, FN18-CRM9 was capable of not only depleting circulating T-cells but also depleting resident T-cells in the lymph nodesl. This immunotoxin also delayed skin allograft rejection as compared to antibody treatment and non-treatment controls. FN18-CRM9 has also been used as an adjunct in inducing tolerance to mismatched kidney transplants (24).

In contrast with ricin and *Pseudomonas* exotoxin (PE) based immunotoxins, there is a potential problem using UCHT1-CRM9, or other DT-based immunotoxins, in the treatment of human diseases. Most people have been immunized against DT. Therefore these people have a pre-existing anti-DT antibody titer which could potentially inhibit or alter the efficacy of these immunotoxins. This limitation also occurred in rhesus monkey studies. FN18-CRM9 could deplete T cells in the blood, but to a much lesser extent in animals with anti-DT antibodies, and the T cells repopulated several days earlier compared to those monkeys without anti-DT titers. In order to overcome this antibody mediated inhibition, the first examination of the effect and the mechanism of human sera containing anti-DT antibodies on UCHT1-CRM9 toxicity was done.

A DT point-mutant, a truncation mutant and DT-subfragments were used in an attempt to neutralize the anti-DT effect in human sera. Based on the neutralization data, a single-chain immunotoxin was constructed with a C-terminal deletion mutant of DT which is expected to bypass the inhibitory effect of the pre-existing anti-DT antibodies.

Cells.

Jurkat cells (ATCC) were maintained in RPMI 1640 supplemented with 10% fetal calf serum, 25 mM sodium bicarbonate and 50 µg/ml of gentamycin sulfate.

Serum and adsorbing molecules.

Goat anti-DT serum was provided by Dr Randall K. Holmes (USUHS, Bethesda, Md.). Human serum samples were provided by Dr. Henry McFarland (NINDS, Bethesda Md.). CRM197, an A-subfragment mutant (Gly 52 to Glu) of DT (see FIG. 1A), with no enzymatic activity (10) is available from Biocine-IRIS (Siena, Italy). MSPΔ5, a truncation mutant (amino acid 385) of DT with an additional 5 amino acids at the C-terminus was provided by Dr. Richard Youle (NINDS, NIH, Bethesda Md.). Purification of the DT B-subfragment has been described (11). Immunotoxins-UCHT1-CRM9 synthesis has been described (12).

The recombinant immunotoxin, sFv-DT390, was generated in two phases. First the coding sequences for the variable light ($V_L$) and variable heavy ($V_H$) chain regions of the UCHT1 antibody were amplified by a two step protocol of RT-PCR using primers based on the published sequence (13). The 5' $V_L$ primer added a unique NcoI restriction enzyme site while the 3' $V_H$ primer added a termination codon at the J to constant region junction and an EcoRI site. The $V_L$ region was joined to the $V_H$ region by single-stranded overlap extension and the two regions are separated by a $(Gly_3Ser)_4$ linker that should allow for proper folding of the individual variable domains to form a function antibody binding site (14). Second, genomic DNA was isolated from a strain of *C. diphtheriae* producing the DT mutant CRM9 (C7[$\beta^{htox-201to-9h'}$]) as described (15). This DNA was used for PCR. The 5' primer was specific for the toxin gene beginning at the signal sequence and added a unique NdeI restriction site. The 3' primer was specific for the DT sequence terminating at amino acid 390 and added an NcoI site in frame with the coding sequence. The PCR products were digested with the appropriate restriction enzymes and cloned into the *E. coli* expression plasmid pET-17b (Novagen, Inc., Madison, Wis., USA) which had been linearized with NdeI and EcoRI. The resulting plasmid was used to transformed *E. coli* BL21/DE3 cells. Cells were grown to an $OD_{590}$ of 0.5, induced with 0.5 M IPTG (Invitrogen, San Diego, Calif., USA) and incubated for an additional 3 hours. The sFv-DT390 protein was isolated in the soluble fraction after cells were broken with a French Press and the lysate subjected to centrifugation at 35,000×g.

Protein Synthesis Inhibition Assay.

Inhibition assays were performed as described (12) with the following modifications. Immunotoxins were incubated for 30 minutes with the indicated serum sample or leucine, free medium at room temperature prior to addition to cells. In some experiments the serum was pre-incubated for 30 minutes with an adsorbing molecule at the given concentrations to bind the antibodies. The immunotoxin/serum mixture was incubated with Jurkat cells ($5\times10^4$ cells/well in 96 well plate) for 20 hours. A 1 hour pulse of [$^3$H]-leucine (4.5 µCi/ml) was given before cells were collected onto filters with a Skatron harvester. Samples were counted in a Beckman scintillation counter. Each experiment was performed in 4 replicates. Results were calculated into a mean value, and recorded as a percentage of control cells.

Serum Antibody Detection.

Anti-DT antibodies were detected in human serum by ELISA. CRM9 (10 µg/ml) was adsorbed to Costar 96-well EIA/RIA flat bottom plates (Costar, Cambridge, Mass., USA) for 2 hours and then washed in phosphate buffered saline (PBS) containing 0.1% Tween 20. Each well was then incubated with PBS containing 3% gelatin to prevent non-specific binding of antibodies to the plastic. Serum samples were diluted in PBS containing 0.1% Tween 20 and 0.3% gelatin prior to addition to the plate. After 1 hour incubation, the wells were washed as above, and incubated for an additional hour with protein A/G-alkaline phosphatase (1:5,000; Pierce, Rockford, Ill., USA). Wells were washed, and phosphatase substrate (Pierce) was added following the manufacturer's directions. After 30 minutes color development was stopped with NaOH and the optical density (OD) was measured with a kinetic microplate reader (Molecular Devices Corporation, Palo Alto, Calif., USA). Each sample was performed in triplicate. Results are presented as O.D. values and antibody titers.

Endocytosis Assay.

UCHT1-CRM9 was iodinated using the Bolton-Hunter reagent (NEN Dupont, Wilmington, Del., USA) as described (16). Jurkat cells were washed twice with binding medium (RPMI 1640 supplemented with 0.2% bovine serum albumin, 10 mM Hepes (pH 7.4) and without sodium bicarbonate). Cells ($1.5\times10^6$) were incubated for 2 hours on ice with $^{125}$I-UCHT1-CRM9 ($1\times10^{-9}$M) that had been pre-incubated with serum or binding medium. Unbound antibody was removed by washing the cells twice in PBS (pH 7.4) with centrifugation and resuspension. Duplicate samples were incubated for 30 minutes on ice or at 37° C. One sample from each temperature point was centrifuged at 800×g to separate the total cell associated (pellet) from the exocytosed or dissociated counts (supernatant). Both fractions were counted in a Beckman a γ-counter. To determine the amount of internalized immunotoxin, cells from the second sample at each temperature were incubated in low pH medium (binding medium containing 10 mM morpholinoethanesulfonic acid, all of which was titrated to pH 2.0 with HCl) for 5 minutes to dissociate the surface bound $^{125}$I-immunotoxin (17). Samples were centrifuged at 800×g to separate the internalized (pellet) from the membrane bound (supernatant). Both fractions were counted in a Beckman 7-counter (Beckman, Fullerton, Calif., USA).

Serum with Anti-DT Antibodies Inhibits UCHT1-CRM9 Toxicity.

Since humans are immunized against DT, the presence of anti-DT antibodies in the serum was determined by ELISA (Table 2). In a limited sample population, 80% of the serum samples had an anti-DT antibody titer of 1:100 or above. The vaccination status of the donors was not available. To determine the effect of these antibodies on UCHT1-CRM9 toxicity, the immunotoxin was pre-incubated with different concentrations of serum and the toxicity of the mixture was assayed (Table 2). Serum samples without a significant ELISA O.D. (2 fold above background) were incapable of affecting UCHT1-CRM9 toxicity at high concentrations of serum (1:10). However, serum samples with a positive ELISA result could neutralize the cytotoxic effect at 1:10 dilution, and those with a high ELISA O.D. (7-11 fold above background) inhibited toxicity even at a 1:100 dilution. Similar results were seen in assays conducted with monkey serum samples.

TABLE 2

Human serum with anti-DT antibodies inhibits the toxicity of UCHT1-CRM9 and the inhibition correlates with the anti-DT titer

| Sample | ELISA O.C. (X ± S.D.) | Titer | Protein Synthesis[b] (% control) 1:10 | 1:100 | 1:1,000 |
|---|---|---|---|---|---|
| 10010 | 0.738 ± 0.017 | 1:750 | 97 ± 3 | 79 ± 8 | 2 ± 0 |
| 10011 | 0.568 ± 0.048 | 1:500 | 104 ± | 13 ± 2 | 2 ± 0 |
| 10012 | 0.491 ± 0.025 | ND[c] | 96 ± 3 | 19 ± 2 | 2 ± 0 |
| 10013 | 0.411 ± 0.052 | 1:500 | 105 ± 8 | 7 ± 1 | 2 ± 0 |
| 10014 | 0.390 ± 0.047 | 1:500 | 96 ± 2 | 7 ± 0 | 2 ± 0 |
| 10015 | 0.353 ± 0.008 | 1:250 | 125 ± 6 | 6 ± 4 | 2 ± 0 |
| 10019 | 0.359 ± 0.019 | 1:250 | 101 ± 7 | 6 ± 1 | 2 ± 0 |
| 10016 | 0.141 ± 0.015 | 1:100 | 22 ± 1 | 3 ± 0 | 2 ± 0 |
| 10017 | 0.100 ± 0.006 | <1:100 | 4 ± 0 | 3 ± 0 | 2 ± 0 |
| 10018 | 0.071 ± 0.001 | <1:100 | 2 ± 0 | 2 ± 0 | 2 ± 0 |
| Goat | 1.450 ± 0.013 | 1:10$^5$ | | 102 ± 19 | 104 ± 3 |

[a]ELISA was performed in triplicate for each serum sample as described under "Materials and Methods." The O.D. values were derived from 1:100 dilutions and presented as a mean value ± SD. The background value was 0.060 ± 0.02. titers are recorded as the highest serum dilution that showed a positive reaction in ELISA.
[b]UCHT1-CRM9 (2 × 10$^{-10}$) was incubated with different dilutions of serum for 30 min. The mixture was then added to cells as described under "Materials and Methods." Four replicates were performed for each sample. Data are presented as a mean value ± S.C. in percentage of the control counts. UCHT1-CRM9 inhibited protein synthesis to 2.0% of controls. The goat anti-DT serum could be diluted to 1:10,000 and still completely inhibited the toxicity of UCHT1-CRM9.
[c]ND, not done Sera do not Inhibit Endocytosis of UCHT1-CRM9.

The inhibitory effect of serum on UCHT1-CRM9 toxicity could be due to prevention of the immunotoxin binding to the cell surface or the endocytosis of UCHT1-CRM9 into the cell. Endocytosis assays were conducted using $^{125}$I-UCHT1-CRM9 to determine if either of these processes were affected by anti-DT antibodies present in sera. The results indicate that the presence of serum (goat anti-DT or human) reduces as much as 80% of the immunotoxin counts binding to the cell surface (Table 3). While this is a significant reduction in binding, limiting 90% of input immunotoxin (one log less UCHT1-CRM9) in toxicity assays reduces protein synthesis to <25% of controls (see FIG. 1). In contrast, the inhibitory effect of serum containing anti-DT antibodies is 100%. Therefore the effect of the anti-DT antibodies is not all at the level of inhibition of binding to the cell surface. The pre-incubation of $^{125}$I-UCHT1-CRM9 for 2 hours on ice and subsequent washing at room temperature resulted in 18 to 25% of the total cell associated counts internalized (Table 3). After incubation for 30 minutes at 37° C., there is a doubling of internalized counts both with and without serum, indicating that the same percentage of labeled immunotoxin is endocytosed. The identical dilutions of serum were incubated with non-labeled UCHT1-CRM9 and used in protein synthesis inhibition assays. The results demonstrate that the ratio of immunotoxin to serum used was capable of completely inhibiting the toxicity (Table 3), although the endocytosis of UCHT1-CRM9 was not affected.

TABLE 3

Inhibition of UCHT1-CRM9 toxicity by serum does not correlate with inhibition of endocytosis.

| Serum Sample | Time (37° C.) | % Bound | % of Bound internalized | Protein Synthesis (% Control) |
|---|---|---|---|---|
| — | 0 | 100 | 23.6. | N.D.[a] |
| — | 30 | 100 | 58.8 | 3 ± 1 |
| Human | 0 | 20 | 18.1 | N.D.[a] |
| Human | 30 | 19 | 35.9 | 105 ± 5 |
| — | 0 | 100 | 25.3 | N.D.[a] |
| — | 30 | 100 | 54.0 | 3 ± 1 |
| Goat | 0 | 37 | 24.4 | N.D.[a] |
| Goat | 30 | 33 | 50.7 | 92 ± 14 |

[$^{125}$I]-UCHT1-CRM9 (2 × 10–9M) was incubated with medium or anti-DT serum (1:4 dilution of human sample 10010 or a 1:1,000 dilution of goat serum; Table 2) for 30 minutes at room temperature. This mixture was added to Jurkat cells (1.5 × 106) for 2 hours on ice (final concentration of [$^{125}$I]-UCHT1-CRM9 was 1 × 10–10). The cells were then washed and endocytosis assays performed as described in Materials and Methods. The % Bound value represents the cell associated counts divided by the cell associated counts divided by the cell associated counts without serum. Non-labeled UCHT1-CRM9 was incubated with the above dilutions of sera and the resulting mixture was used in protein synthesis inhibition assays. The results shown are representative of two independent assays.

The Inhibitory Effect of Anti-DT Antibodies can be Removed by Adsorption.

Figure 1B:
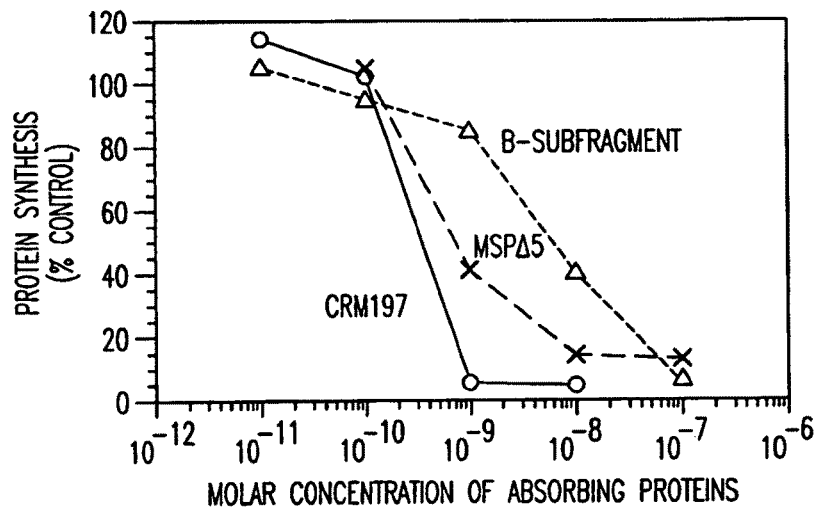
Figure 1C:
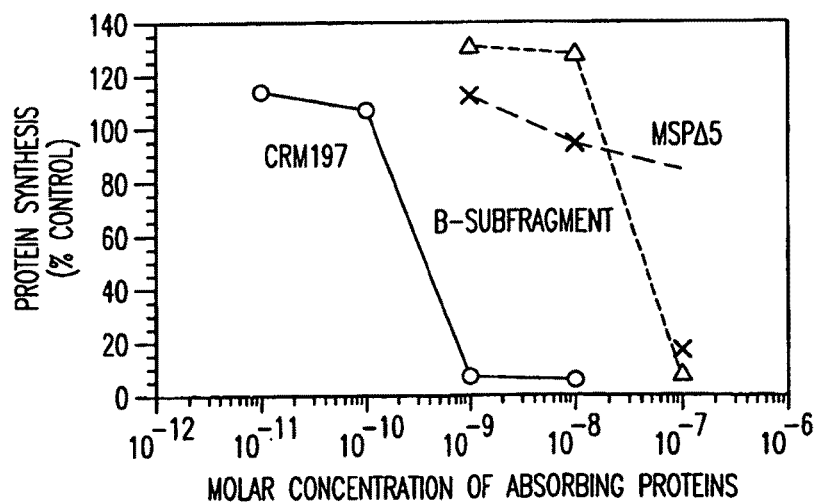

To prevent the inhibitory effect of serum as well as gain insight into the mechanism by which serum inhibits toxicity, experiments were designed to adsorb the protective anti-DT antibodies from the serum. The serum (a pool of all human sera with positive anti-DT ELISA or goat anti-DT) was pre-incubated for 30 minutes with increasing concentrations of CRM197 (an A-chain mutant of DT with no enzymatic activity), MSPΔ5 (a truncation mutant missing the last 150 amino acids) and the purified A- and B-subfragments of DT (FIG. 1A). The adsorbed serum was then incubated with UCHT1-CRM9 in protein synthesis inhibition assays. CRM197, the full length DT-like construct, was capable of completely adsorbing the protective antibodies from both goat (FIG. 1B) and pooled human serum (FIG. 1C). The B-subfragment of DT is also capable of complete adsorption, however ~100 fold more is required. The A-subfragment of DT had little or no effect on either serum, although the serum samples were demonstrated to contain antibodies reactive to both the A- and the B-subfragments by Western Blot analysis. Of interest were the results seen with MSPΔ5, the truncation mutant. Adsorption of goat serum with MSPΔ5 gave a dose dependent removal of the serum's protecting effect (FIG. 1B). However, this adsorption could not bring toxicity down to levels obtained when CRM197 or the B-subfragment was used.

In contrast to the results observed with the goat serum, MSPΔ5 had little effect on pooled human serum (FIG. 1C). These results suggest that the pre-existing anti-DT antibodies important for the protecting effect in human serum are mainly directed against the last 150 amino acids of DT.

sFv-DT390 is not Inhibited by Anti-DT Antibodies Present in Human Sera.

Having observed that the epitope(s) recognized by the antibodies important for protection lay in the C-terminal 150 amino acids, a single-chain immunotoxin was generated with the first 390 amino acids (out of 535) of DT. Position 390 was chosen for 2 reasons: first, the 3 dimensional structure of DT suggested that this position was an external point on the molecule away from the enzymatic domain (18), and second, fusion toxins have been generated with longer DT subfragments with no reports of serum effects (19). The DNA encoding the first 390 amino acids of DT was ligated to DNA encoding the anti-CD3εsFv ($V_L$ linked to $V_H$ using a $(Gly_3Ser)_4$ linker sequence). The predicted molecular weight for the fusion protein is 71,000 Daltons and has been confirmed by Western Blot analysis of both in vitro transcribed and translated protein as well as protein isolated from E. coli using goat anti-DT antibodies. The toxicity of sFv-DT390 protein, isolated from E. coli strain BL21/DE3, was compared to UCHT1-CRM9 in protein synthesis inhibition assays. The $IC_{50}$ (concentration required to inhibit protein synthesis to 50% of controls) of sFv-DT390 was $4.8 \times 10^{-11}$ M compared to $2.9 \times 10^{-12}$ M for UCHT1-CRM9, a 16-fold difference (i.e., 16-fold less toxic). To demonstrate the specificity of the sFv-DT390 construct, competition experiments were performed using increasing concentrations of UCHT1 antibody as competitor. The results showed that approximately ⅛ antibody is needed to compete the sFv-DT390 toxicity to 50% as compared to UCHT1-CRM9. The antibody was capable of totally competing toxicity of both constructs thereby showing their specificity. The immunotoxins were then subjected to protein synthesis assays in the presence of increasing dilutions of serum (Table 4).

UCHT1-CRM9 toxicity was completely inhibited with a 1:10 dilution of the human sera but at a 1:100 dilution toxicity was equivalent to controls without serum. In contrast, the sFv-DT390 immunotoxin is only partially inhibited with the 1:10 dilution of the human sera and the 1:100 dilution no effect on the toxicity. Both immunotoxins are completely inhibited by goat anti-DT serum (1:1,000 dilution). These results indicate that the sFv-DT390 immunotoxin partially evades the pre-existing anti-DT antibodies present in most human sera.

These results indicate that the pre-existing anti-DT antibodies present in human serum inhibit the toxicity of the immunotoxin UCHT1-CRM9. This inhibition of toxicity was also observed with goat anti-DT serum, however less goat serum was needed to completely inhibit toxicity. The experiments were designed in such a way to mimic the in vivo situation. The peak concentration of circulating immunotoxin currently being tested in animal models is $1 \times 10^{-9}$ M. The immunotoxin concentration incubated with the 1:10 dilution of human serum was $1 \times 10^{-10}$ M, thus approximating in vivo conditions. The inhibition of toxicity correlates with the serum antibody levels as determined by ELISA (Table 3), indicating that sera with higher anti-DT titers have a stronger inhibitory effect. Similarly, the goat anti-DT serum which gave the highest ELISA value could be diluted 10,000 times and still completely inhibited UCHT1-CRM9 toxicity. Since this correlation exists, there is no indication that any other component of the serum inhibits the toxicity of UCHT1-CRM9.

Furthermore, the data show that a titer of 1:100 dilution is necessary for an inhibition of the immunotoxin toxicity. A construct in which the first 486 amino acids of DT were fused to interleukin-2, $DAB_{486}IL-2$, was used in lymphoid malignancy patients. A partial response to $DAB_{486}IL-2$ was observed in several patients who had a anti-DT titer below 1:100 dilution prior to the treatment.

Intoxication of cells by immunotoxins can be subdivided into four general stages: 1) specific binding to the cell surface, 2) endocytosis into the cell, 3) translocation of enzymatic domain of the toxin out of the endosome and 4) enzymatic inactivation of the target molecule. The results presented indicate that, while the amount of immunotoxin reaching the cell surface is lower in the presence of serum, the same percentage of bound immunotoxin is endocytosed. Taking into account the reduced amount of immunotoxin bound to the cell, the amount of endocytosed immunotoxin should intoxicate the cells to below 25% of controls. However, the immunotoxin had no effect on protein synthesis in the presence of serum containing anti-DT antibodies. Since the A-subfragment of DT could not adsorb the protective effect of serum while the B-subfragment could, the effect of serum is not likely to be at the level of inhibiting enzymatic activity of the toxin. Therefore, the anti-DT antibodies probably affect the translocation of the A-subfragment into the cytosol.

CRM197, B-subfragment, and MSPΔ5 could adsorb the protecting anti-DT antibodies from the goat and rhesus monkey sera. However, among the 3 DT mutants, MSPΔ5 could not prevent the UCHT1-CRM9 toxicity in the presence of the human sera, showing a difference in the anti-DT antibody repertoire among humans, goat and rhesus monkeys. This difference does not seem to be due to immunization routes, because monkeys used in the present study were not immunized for DT and presumably acquire the antibodies after a natural infection with toxigenic strains of C. diphtheriae. There have been reports showing that rhesus monkeys and humans shared a similar antibody repertoire (21), but the present results suggest that the effect of antibodies from the host for whom immunotoxin treatment is intended should be useful.

To overcome the blocking effect of the pre-existing anti-DT antibodies in human sera, there are basically two pathways existing. One is to neutralize the antibodies with non-toxic DT mutants, and the other is to modify the DT structure used for making immunotoxin (3). The antibody neutralization pathway has been tested in monkey studies of FN18-CRM9 treatment as described above.

The present results showed that although antibodies against both A- and B-subfragments existed in human sera, MSP5 could not neutralize the pre-existing protective anti-DT antibodies, and therefore could not prevent the inhibition of the cytotoxicity of UCHT1-CRM9. However, it did block the inhibitory effect of the goat and monkey sera. This prompted the construction of the present recombinant immunotoxin, sFv-DT390. The $IC_{50}$ of sFv-DT390 is $4.8 \times 10^{-11}$ M, 1/16 as potent as UCHT1-CRM9. Like many other single-chain constructs, sFv-DT390 is monovalent as compared to immunotoxins generated with full length, bivalent antibodies. The reduced toxicity in sFv-DT390 could be explained primarily on this affinity difference. Immunotoxins generated with purified F(ab)' fragments of antibodies also show an in vitro loss in toxicity (generally a 1.5 log difference) when compared to their counterparts generated with full length antibodies (22). The toxicity of sFv-DT390 is comparable to that reported for DAB486IL-2 (23). From the present data some advantages of sFv-DT390 are expected. First, sFv-DT390 is only 1/3 of the molecular weight of UCHT1-CRM9. The molar concentration of sFv-DT390 will be 3 times higher than that of UCHT1-CRM9 if the same amount is given (for example, 0.2 mg/kg). Therefore, their difference in potency could be reduced to approximately 5 times. Second, in an in vitro experiment (Table 4), the same molar concentration of sFv-DT390 and UCHT1-CRM9 was used for serum inhibition test, although the former is only 1/16 potent compared to the latter. The pre-existing anti-DT antibodies in human sera could only partially block the toxicity of sFv-DT390 while the effect of UCHT1-CRM9 was completely blocked. Thus, sFv-DT390 is expected to bypass the anti-DT antibodies in in vivo situations while UCHT1-CRM9 cannot. Third, sFv-DT390 contains only the variable region of UCHT1, and is expected to have less immunogenicity in human anti-mouse antibody (HAMA) responses than the native murine antibody UCHT1. Finally, the production cost of sFv-DT390 is much lower than that of UCHT1-CRM9. Based on these reasons, sFv-DT390, or others with similar properties, are expected to be useful in the treatment of T-cell mediated diseases in humans, especially in anti-DT positive individuals and in patients who need repeated treatments. To obtain evidence supporting this assumption, it is only necessary to construct a rhesus monkey analog of sFv-DT390, and test it in monkey models as described in previous examples.

TABLE 4

Anti-DT antibodies present in human sera have reduced effect on sFv-DT390 toxicity.

| | | Protein synthesis (% Contol) | | | | | |
|---|---|---|---|---|---|---|---|
| | ELISA value | UchT1CRM9 | | | sFv-DT390 | | |
| Serum Sample | (±S.D.) | 1:10 | $1:10^2$ | $1:10^3$ | 1:10 | $1:10^2$ | $1:10^3$ |
| 10012 | 0.491 ± 0.025 | 119 ± 24 | 8 ± 2 | ND[a] | 47 ± 9 | 21 ± 8 | ND |
| Pooled | 0.331 ± 0.015 | 108 ± 37 | 7 ± 1 | ND[a] | 49 ± 7 | 16 ± 7 | ND |
| Goat | 1.450 ± 0.013 | ND | ND | 94 ± 21 | ND | ND | 8 ± 11 |

[a]Not done
UCHT1CRM9 or sFv-DT390 ($2 \times 10^{-9}$M) was incubated with the indicated dilutions of serum for 30 min. The mixture was then added to cells as described under "Materials and Methods." The final concentration of immunotoxin on cells was $1 \times 10^{-10}$ M. Four replicates were performed for each sample. Data are presented as a mean value ±S.D. in percentage of the control counts. UCHT1-CRM9 inhibited protein synthesis to 5% of controls while the sFv-DT390 inhibited protein synthesis to 18% of controls.
The ELISA value was determined using a 1:100 dilution of serum. The results are representative of two independent experiments.

EXAMPLE 6

Expression and Characterization of a Divalent Chimeric Anti-Human CD3 Single Chain Antibody Murine anti-CD3 monoclonal antibodies (mAbs) are used in clinical practice for immunosuppression. However, there are two major drawbacks of this treatment: the associated cytokine release syndrome and human anti-mouse antibody response. To overcome these side effects, a chimeric anti-human CD3 single chain antibody, scUCHT1 was generated. It is an IgM variant of the UCHT1 described in Example 9. scUCHT1 consists of the light and heavy variable chain binding domains of UCHT1 and a human IgM Fc region ($CH_2$ to $CH_4$). The method used was reported by Shu et al. [37] and is further described below. The following data show that the engineered chimeric anti-CD3 single chain antibody (scUCHT1) will be useful in clinical immunosuppressive treatment.

Oligonucleotide Primers and DNA Amplification.

Figure 2:
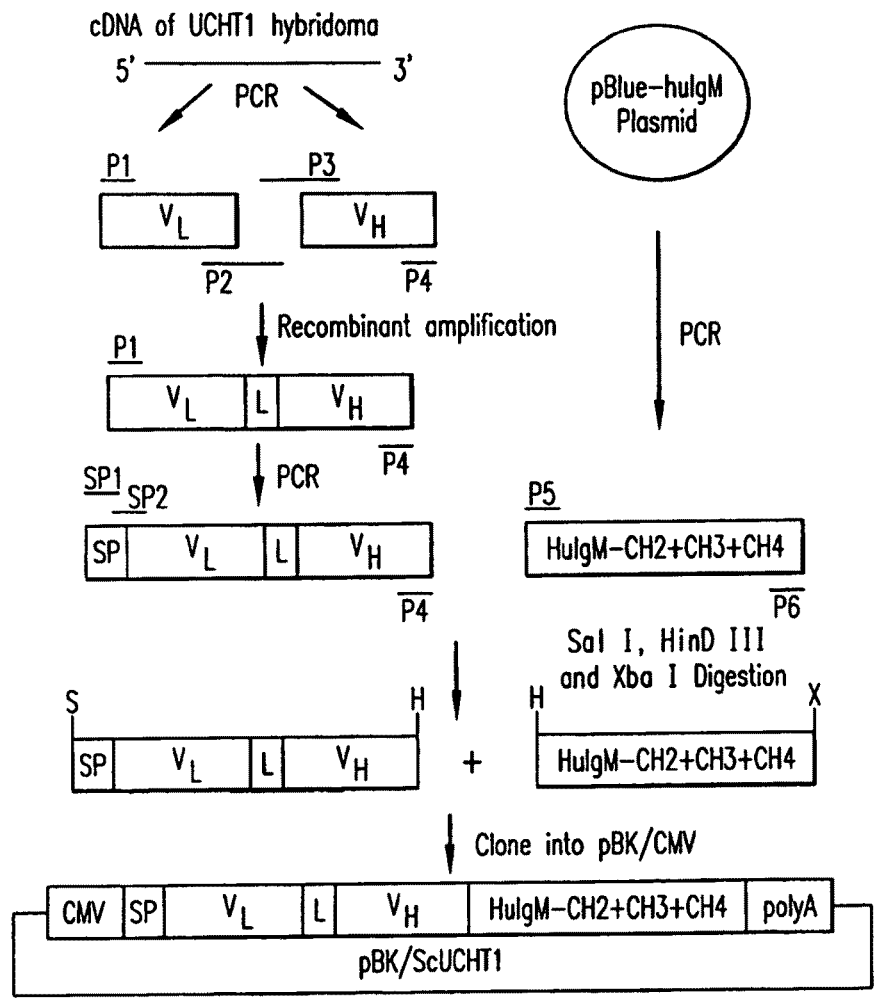
FIG. 2 shows the schematic flow sheet for generation of the single chain antibody scUCHT1 gene construct. PCR: polymerase chain reaction; L: linker; SP: signal peptide. P1 to P6, SP1, and SP2 are primers used in PCR.

The procedures of cloning scUCHT1 is schematically depicted in FIG. 2. mRNA isolated from UCHT1 hybridoma cells (provided by Dr. P. C. Beverley, Imperial Cancer Research Fund, London was reverse transcribed into cDNA. The $V_L$ and $V_H$ regions of UCHT1 were amplified with polymerase chain reaction (PCR) from the cDNA using primer pairs P1, P2 and P3, P4 respectively. Primers P2 and P3 have a 25 bp complementary overlap and each encoded a part of a linker peptide $(Gly_4Ser)_3$. The single chain variable fragment ($V_L$-linker-$V_H$) was created by recombinant amplification of $V_L$ and $V_H$ using primers P1 and P4. A mouse kappa chain signal sequence was added at the $V_L$ 5'-end by PCR, first with primers SP2 and P4, and then with primers SP1 and P4. The human IgM Fc region ($CH_2$ to $CH_4$) was amplified from the plasmid pBlue-huIgM (kindly provided by Dr. S. V. S. Kashmiri, National Cancer Institute, Bethesda. This gene fragment was about 1.8 kb. The $V_L$-linker-$V_H$-CH2 region which is important for antigen recognition was confirmed by sequence analysis. Finally, the single chain variable fragment and the human IgM Fc region were cloned into plasmid pBKJCMV (Stratagene, La Jolla, Calif., USA). Using the generated pBK/scUCHT1 plasmid as template, an in vitro transcription-translation assay yielded a product of 75 kDa, the expected size.

Expression in COS-7 and SP2/0 Cells.

The gene fragment encoding scUCHT1 was then cloned into an expression vector pLNCX [36]. The scUCHT1 gene construct was introduced into COS-7 cells with a calcium-phosphate method [32], and introduced into SP2/0 myeloma cells by electroporation [33]. Cells transfected were selected with 500 μg/ml G418 (GIBCO/BRL, Gaithersburg, Md., USA) in DMEM medium. The drug resistant transfectants were screened for scUCHT1 secretion by an anti-human IgM ELISA technique. Transfectants secreting scUCHT1 were cloned by limiting dilution.

Two stable clones, COS-4C10 and SP2/0-7C8, which could produce about 0.5 mg/ml scUCHT1 in culture medium, were selected for further evaluation. The culture supernatant of COS-4C10 and SP2/0-7C8 cells was analyzed by immunoblotting using anti-human IgM antibody. Human IgM antibody was included as a control in the analysis. Under reducing conditions, scUCHT1 produced by COS-7 and SP2/0 cells had a similar electrophoretic mobility to that of the control human IgM heavy chain (75 kDa). Under non-reducing conditions, scUCHT1 from COS-7 cells appeared as a single band of approximately 150 kDa, which was thought to be a homodimer of the single chain antibody. SP2/0 cells mainly produced a protein of similar size with some higher molecular weight products.

In constructing scUCHT1, the domain orientation of sFv, $V_H$-$V_L$, which Shu et al. used to $V_L$-$V_H$ orientation, was changed so that the heavy chain constant domains were linked to the $V_H$ domain. In mammalian cells, secretion of immunoglobulin molecules is mediated by light chain, and free light chain is readily secreted [38]. However, free heavy chain is generally not secreted [39]. In a bacterial expression system, the yield of secreted sFv with a $V_L$-$V_H$ domain orientation was about 20-fold more than that obtained with a $V_H$-$V_L$ domain orientation [40]. It was reasoned that $V_L$ at the NH2-terminal position and $V_H$ linked to heavy chain constant region in scUCHT1 construct might enhance the secretion of this immunoglobulin-like molecule in mammalian cells. In fact scUCHT1 was efficiently produced by both COS-7 and SP2/0 cells. Hollow fiber culture should increase its production. Moreover, scUCHT1, the IgM-like molecule, has a secretory tailpiece with a penultimate cysteine (Cys 575) which is involved in polymerization and also provides retention and degradation of IgM monomers [41-43]. Replacing the Cys 575 with serine might also greatly improve the yield.

scUCHT1 secreted from COS-7 cells was shown to be a divalent form by immunoblotting, suggesting a disulfide bond linkage of two monovalent molecules. The disulfide bond is likely situated between the CH2 and CH3 regions, where the Cys 337-Cys 337 disulfide bond is thought to exist. Cys 337 is believed to be sufficient for assembly of IgM monomers, and was neither sufficient nor necessary for formation of polymers. However, Cys 575 was necessary for assembly of IgM polymers, and Cys 414 was not required for formation of IgM monomers or polymers [44]. This divalent form of the single chain antibody should increase its binding affinity. While scUCHT1 produced from SP2/0 cells was mainly in the divalent form, a small fraction of the antibody had a higher molecular weight, nearly comparable to that of the human IgM pentamer, the natural form of secreted human IgM.

Western Blotting Analysis of scUCHT1.

scUCHT1 was precipitated from the culture supernatant using goat anti-human IgM-Agarose (Sigma, St. Louis, Mo., USA), and separated on 4-20% SDS-PAGE gradient gel under reducing and non-reducing conditions. The separated proteins were transferred to ProBlott™ membrane (Applied Biosystems, Foster City, Calif., USA) by electroblotting at 50 volts for 1 hour. The membrane was blocked and incubated with alkaline phosphatase labeled goat anti-human IgM antibody (PIERCE, Rockford, Ill., USA) following the manufacturer's instruction. Color development was carried out with substrate NBT/BCIP (PIERCE).

Purification of scUCHT1.

Culture supernatant was mixed with anti-human IgM-Agarose, and incubated at 4° C. with shaking overnight, and then the mixture was transferred to a column. The column was washed with washing buffer (0.01 M Na-phosphate, pH 7.2, 0.5 M NaCl) until the OD280 of flow-through was <0.01. scUCHT1 was eluted with elution buffer (0.1 M glycine, pH 2.4, and 0.15 M NaCl). The fractions were neutralized with 1 M Na-phosphate (pH 8.0) immediately, and then concentrated and dialyzed against PBS.

Competitive Binding Assay.

The parental antibody UCHT1 was iodinated using Bolton-Hunter Reagent (NEN, Wilmington, Del., USA) as described previously [34]. The $^{125}$I-labeled UCHT1 was used as tracer and diluted with DMEM medium to 0.3-0.6 nM. UCHT1 and the purified scUCHT1 from COS-7 and SP2/0 transfectant cells were used as competitors. Human CD3 expressing Jurkat cells were suspended in DMEM medium ($2\times10^7$/ml). 50 µl of such cell suspension ($1\times10^6$) was incubated with 50 µl diluted tracer and 50 ml diluted competitors on ice for 2 hours. Afterwards, cells were pelleted, and counted in a gamma counter. Results were expressed as a percentage of the $^{125}$I-UCHT1 bound to cells in the absence of competitors.

scUCHT1 from both COS-7 and SP2/0 cells could specifically inhibit the binding of $^{125}$I-UCHT1 to Jurkat cells in a dose dependent way. As the concentration of the competitors (UCHT1, scUCHT1 from COS-7 and SP2/0 cells) increased from 1 to 100 nM, the tracer ($^{125}$I iodinated UCHT1) bound to Jurkat cells decreased from 80% to nearly 0%. No significant difference was observed among the affinity curves of UCHT1 and scUCHT1 from COS-7 and SP2/0 cells. This indicates that the engineered antibody scUCHT1 has nearly the same affinity as UCHT1. Moreover, scUCHT1 contains human IgM constant region, and is expected be less immunogenic than UCHT1. The degree of its immunogenicity might vary due to the murine variable region of scUCHT1. Humanized variable regions by CDR-grafting or human variable regions can be used to further reduce its immunogenicity [31].

T-Cell Proliferation Assay.

T-cell proliferation in response to UCHT1 and scUCHT1 was tested on human PBMCs from a healthy donor. Human peripheral blood mononuclear cells (PBMCs) were isolated from blood of a healthy adult by density centrifuge over Ficoll-Hypaque gradient [34]. The PBMCs were resuspended in RPMI 1640 supplemented with 10% FCS and aliquoted to 96-well U-bottom plates at $5\times10^4$ cells/well. Increasing amounts of anti-CD3 antibodies (UCHT1, scUCHT1) were added. After 72 hours of culture at 37° C. in a humidified atmosphere containing 5% $CO_2$, 1 µCi [$^3$H]thymidine (NEN) was added to each well. 16 hours later, cells were harvested and [$^3$H]thymidine incorporation was counted in a liquid scintillation counter.

The parental antibody UCHT1 started to induce proliferation at 0.1 ng/ml, and peaked at 100 ng/ml. A small drop in CPM was observed as the concentration increased to 1,000 ng/ml. However, [$^3$H]thymidine incorporation in PBMCs incubated with scUCHT1 was only slightly increased in the range of 0.1-10 ng/ml, and when the concentration was higher than 10 ng/ml, the incorporated counts decreased and were close to 0 counts at 1,000 ng/ml. Thus showing that scUCHT1 did not induce a human T cell proliferation response.

Measurement of TNF-α and IFN-γ.

TNF-α and IFN-γ productions of human PBMCs induced by UCHT1 and scUCHT1 were measured with ELISA. $4\times10^5$ PBMCs were cultured with serial dilutions of anti-CD3 antibodies (UCHT1, scUCHT1) in 96-well flat-bottom plates in RPMI 1640 supplemented with 10% FCS. Supernatant was collected at 36 hours for TNF-α and 72 hours for IFN-γ after the start of the culture [35]. TNF-α and IFN-γ were measured with ELISA kits (Endogen Inc. Cambridge, Mass., USA) following the manufacturer's instruction.

The native antibody UCHT1 induced production of both TNF-α and IFN-γ in a dose dependent way. Higher concentration of UCHT1 induced higher production of TNF-α and IFN-γ. On the contrary, scUCHT1 did not induce secretion of TNF-α at any concentration, and inhibited IFN-γ production when its concentration was higher than 0.1 ng/ml. At the time of supernatant harvesting, the PBMCs cultured with UCHT1 and scUCHT1 were also checked with trypan blue exclusion test. Cells were shown to be alive in both situations. In TNF-α and IFN-γ ELISA assays, an unrelated human IgM was included and it did not affect the TNF-α and IFN-g production.

Anti-CD3 mAbs can induce T cell activation and proliferation both in in vitro and in vivo situations [45]. Crossing-linking of anti-CD3 antibody between T cells and FcR expressing cells is an essential step in this process [46]. T cell activation therefore reflects an efficient interaction of the mAb with a human FcR. Previous data of in vitro study indicated that T cell activation resulted in increased production of TNF-α, IFN-γ, and IL-2 [24]. Human IgG Fc receptors (FcγR I, FcγR II, FcγR III) are distributed on human monocytes, T, B lymphocytes, and NK cells [47]. FcγR I and FcγR II can recognize both mouse and human IgG. In accordance with the above observation, UCHT1 was potent in induction of T cell proliferation and TNF-α and IFN-γ release. Human IgM Fc receptor (FcµR) was reported to be present mainly on a small fraction of B lymphocytes, NK cells, and possibly a helper subset of T lymphocytes [47, 48]. Pentamer form of IgM and an intact $CH_3$ domain are required for optimal binding to FcµR. Monomeric or dimeric subunits of IgM are less efficient in binding to FcµR [49, 50]. Cross-linking of IgM to FcμR on T cells inhibited the mitogen-induced T cell proliferation, and FcμR may function as a negative signal transducing molecule [51, 52].

Therefore, it can specifically bind to human CD3 molecule and FcμR. It is conceivable that scUCHT1 can cross-link human B and T cells, and possibly T and T cells. In an in vitro assay, scUCHT1 from both COS-7 and SP2/0 cells had little effect in the T cell proliferation assay at low concentrations (below 10 ng/ml), and became inhibitory as the concentration increased. In accordance with these results, scUCHT1 did not induce TNF-α production and even inhibited the basal yield of IFN-γ.

The present chimeric anti-CD3 single chain antibody scUCHT1 possesses high human CD3 binding specificity and affinity, and does not induce T cell proliferation and cytokine release. Moreover, it has a human IgM Fc fragment, which should decrease the possibility of inducing human anti-mouse antibody response. Thus, scUCHT1 can be used for clinical immunosuppressive treatment.

EXAMPLE 7

Cloning the Full-Length of DT Gene for the Construction of DTM2

Corynebacteriophage beta (*C. diphtheriae*) tox 228 gene sequence was from genebank. (*Science* 221, 885-858, 1983). The sequence is 2220 bp. There are 300 bp of 5' untranslated region (1 to 300) including the promoter sequence around (−180 to −10), 1682 of coding region (301-1983) including signal peptide (301 to 376), A chain (377 to 955) and B chain (956 to 1983), and 3' untranslated region (1984 to 2220).

The full-length DT was amplified in two fragments. The pelB leader sequence (ATG AAA TAC CTA TTG CCT ACG GCA GCC GCT GGA TTG TTA TTA CTGCGCT GCC CAA CCA GCG ATG GCC 3') SEQ ID NO:1) was added to the 5' end of the DT coding sequence to all the constructs during polymerase chain reaction by primer EcosignalDT-1 and EcosignalDT-2. The upstream fragment of 311 bp (from position 301 to 546 bp) was amplified by oligo EcosignalDT-2 and p546R with CRM9 DNA as a template and the downstream fragment of 1471 bp was amplified by p514S and p1983R with the DTM1 DNA as template. Then, the combined PCR product of full-length DT was amplified with primer EcosignalDT-1 and p1983R. As a result, the amplified DT coding sequence (position 376 to 1983 bp) acquired the pelB leader sequence added to the 5' end and contains the two mutant sites [(508 Ser to Phe) and (525 Ser to Phe)] as DTM1 does.

Primers:

EcosignalDT-1
(SEQ ID NO: 2)
5' ATG AAA TAC CTATTG CCT ACG GCA GCC GCT GGA TTG TTA TTA CTC GCT GCC CAA 3'

EcosignalDT-2
(SEQ ID NO: 3)
5' GGA TTG TTA TTA CTC GCT GCC CAA CAA GCG ATG GCCGGC GCT GAT GATGTT GTT GAT TC 3' p546R:
(SEQ ID NO: 4)
5' CGGTACTATAAAACTCTTTCCAATCATCGTC 3' p514S:
(SEQ ID NO: 5)
5' GACGATGATTGGAAAGAGTTTTATAGTACCG 3' p1983R:
(SEQ ID NO: 6)
5' AGATCTGTCGA/CTCATCAGCTTTTGATTTCAAAAAATAGCG 3'.

A mutant residue was introduced at position 52. The glycine (GGG) at position 52 wild type DT was substituted by glutamic acid (GAG). The two primers p546R and p514S carried the mutant codon (GGG to GAG). The PCR products of these two primers contained the substituted codon (GAG) instead of codon GGG. The jointed double stranded DNA of the two fragments (1683 bp) were cloned into pET 17b by restriction site NdeI and BamHI.

The data show that anti-human blocking antibodies are specifically directed at the toxin C-terminus. Although a specific sequence derived from the UCHT1 VLVH regions is described, anyone skilled in the art could make sequence variations in VLVH domains which can be designed to increase the affinity of the sc-anti-CD3-antibody conferring a more favorable therapeutic ratio to fusion immunotoxins using this derivative. Such modifications are within the scope of the present teaching. The disadvantage of the monovalent antibody VLVH construct, is that it has a lower affinity for T cells compared to the chemically coupled conjugate which utilizes a divalent antibody.

These are believed to be the first instances of a sc anti-CD3 antibodies. IgM was chosen since very few B cells or macrophages contain IgM Fc receptors. (Binding of immunotoxin to cells other than T cells reduces the specificity of the anti-T cell immunotoxin and this situation is purposefully avoided). However, using a bacterial expression system no carbohydrate is attached to the antibody which also eliminates Fc receptor binding. Thus, substituting other human IgG constant domains would be a routine modification and should be claimed.

Figure 3:
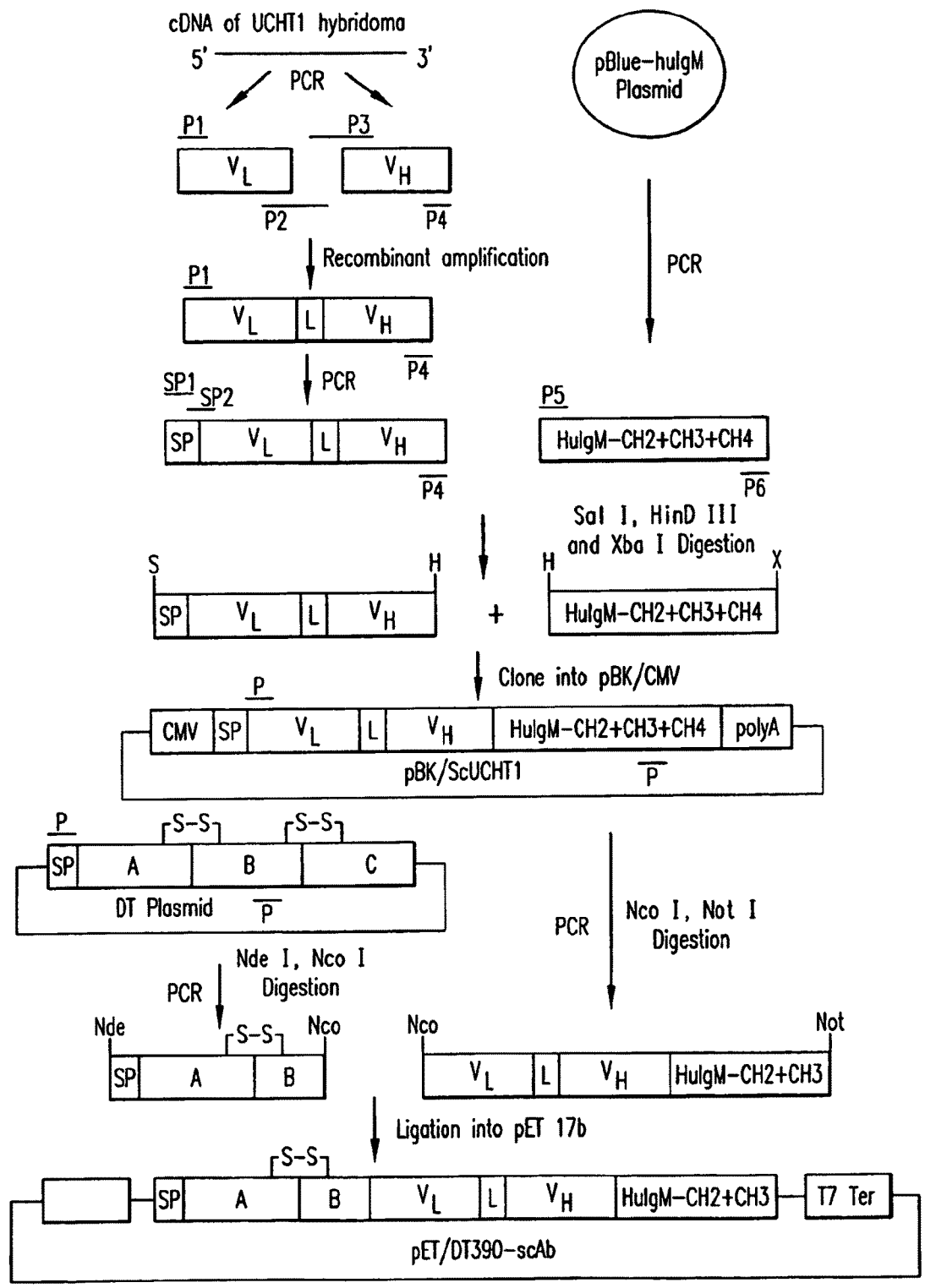
FIG. 3 shows one clone expressing the divalent immunotoxin fusion protein shown in FIG. 5.
Figure 4:
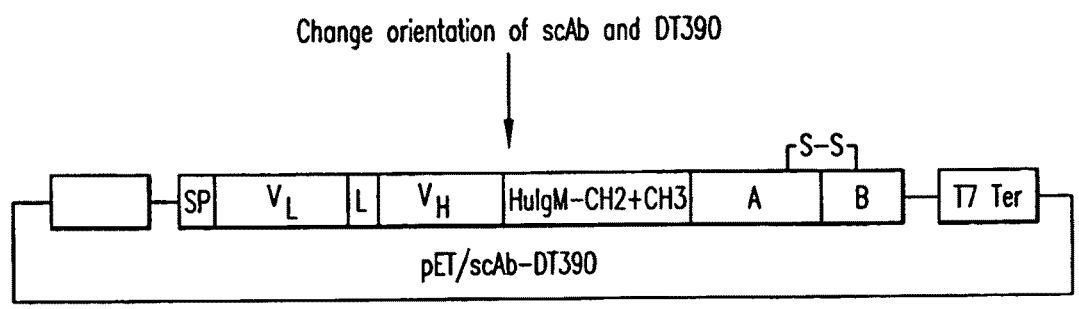
FIG. 4 shows another clone expressing a divalent immunotoxin fusion protein shown in FIG. 7.
Figure 5:
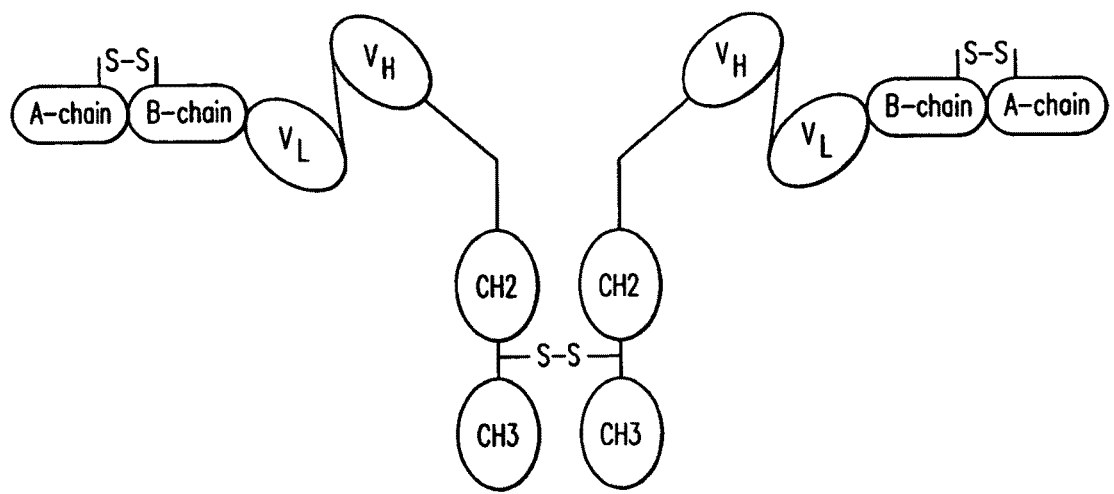
FIG. 5 is a schematic of a divalent fusion immunotoxin.
Figure 6:
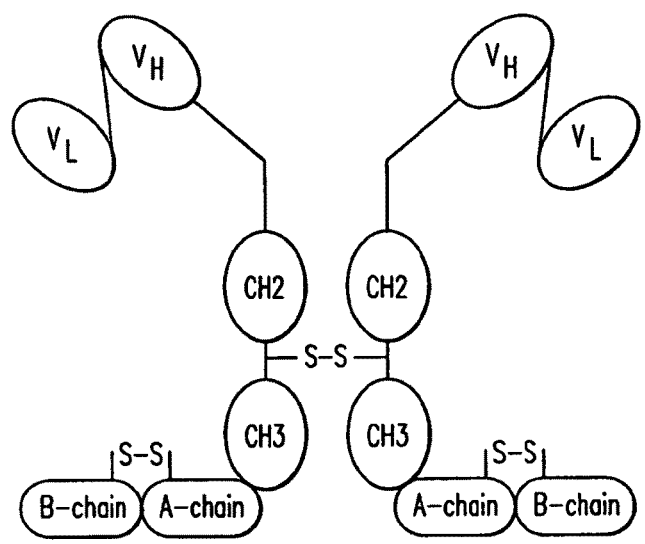
FIG. 6 is a schematic of a divalent fusion immunotoxin.
Figure 7:
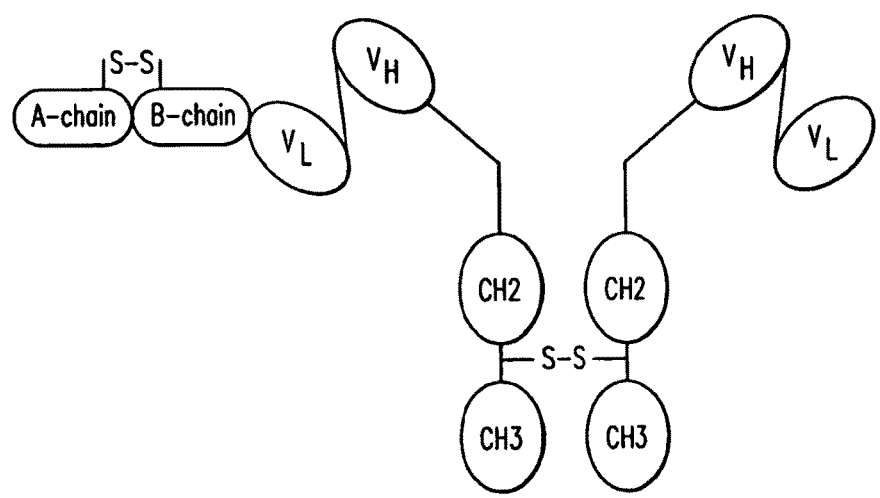
FIG. 7 is a schematic of a divalent fusion immunotoxin.

A variety of divalent fusion protein immunotoxins are provided: These have been expressed in *E. coli*, and Western blots of reduced and non-reduced SDS gels confirm that most of the immunotoxin is secreted as the dimeric (divalent) species. The position of the toxin has been varied in an attempt to minimize stearic hindrance of the divalent antibody site, yet provide the best interactions with the CD3 receptor to facilitate toxin translocation across the membrane. PCR amplification was conducted using BamHI and NdeI restriction sites and the pET17b vector. FIGS. 3 and 4 show two different clones expressing divalent immunotoxin fusion proteins cartooned in FIGS. 5 and 6, respectively. Another variation is shown in FIG. 7. The clone producing this consists of a clone constructed by using the single chain antibody followed by a stop codon and the single chain immunotoxin, all under one promoter (Better et al. *Proc. Natl. Acad. Sci.* 90:457-461, January 1993). After secretion and oxidation of the interchain disulfide, 3 species are present: sc divalent antibody, divalent fusion immunotoxin, and a divalent sc antibody containing only one toxin. This species is isolated by size separation and is the species cartooned in FIG. 7. The advantage of this species is that stearic hindrance to the divalent antibody domains is limited by the presence of only one toxin domain. Other variations are routine to construct given the methods described herin and in the art. Those diagramed are considered to be the most likely to exhibit divalent character. Numerous orientations of toxin relative to antibody domains can be made and many are expected to be effective.

Figure 8:
FIG. 8 shows the cloning scheme used to obtain scUCHT1 fusion protein with DTM1 and DT 483.
Figure 8:
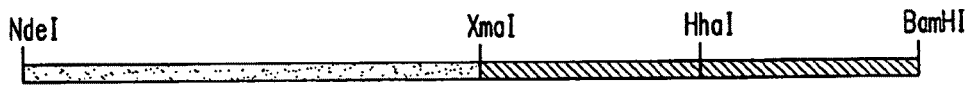
Figure 8:
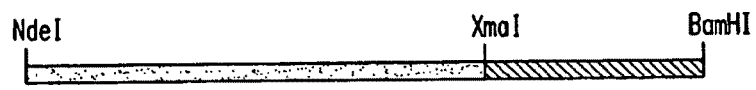
Figure 8:
Figure 8:
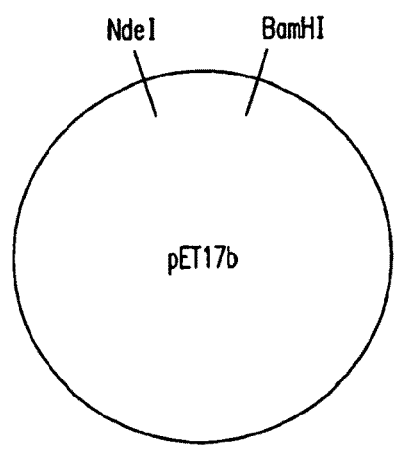
Figure 9:
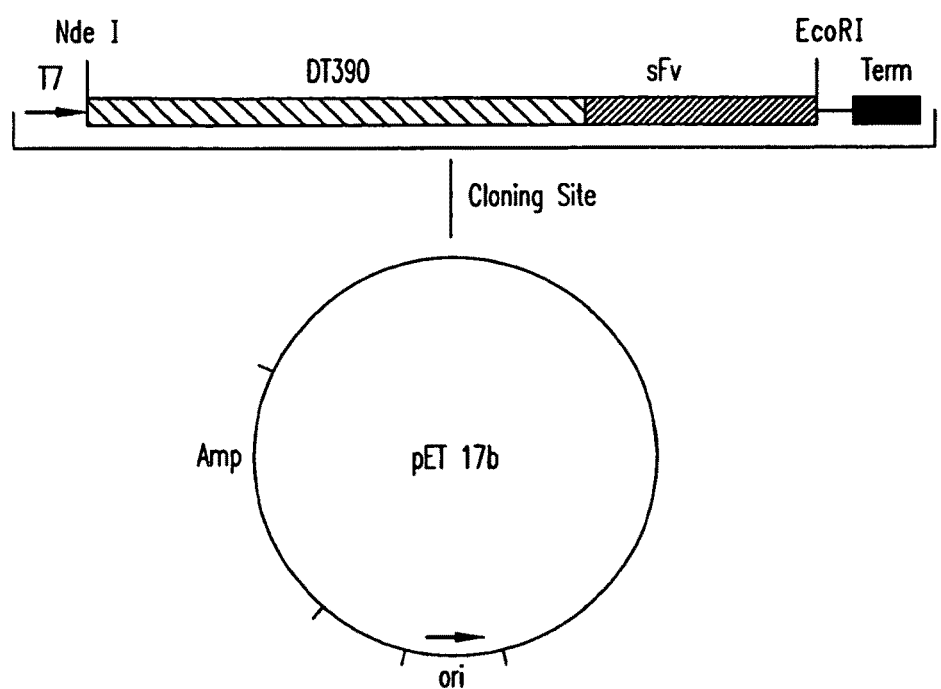
FIG. 9 shows the cloning scheme used to obtain scUCHT1 fusion protein with DT 390.
Figure 10:
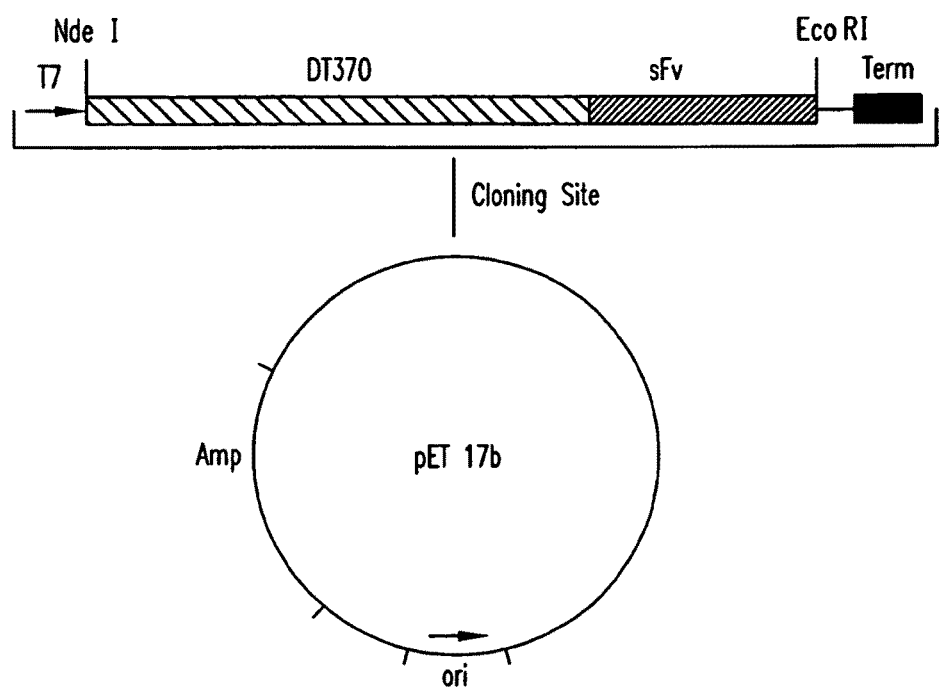
FIG. 10 shows the cloning scheme used to obtain scUCHT1 fusion protein with DT 370.

In addition, the length of the toxin C-terminus has been varied to provide optimization between two competing functions. The numbers after DT refer to the number of amino acid residues counting the amino terminus of the toxin A chain as 1. The full length toxin is called DTM1 and was provided by Dr. Richard Youle NINDS, NIH (Nicholls et al. *J. Biol. Chem.* 268(7):5302-5308, 1993). It has point mutations S to F at positions 508 and 525. This full length toxin mutant has the essential mutation of CRM9, S to F at 525 which reduces binding to the DT receptor by 3-4 logs without abolishing the translocation function. The other mutation S to F at 508 has been added because of previous restrictions on cloning mutant DT that can revert to wild type toxin with a minimum lethal dose of 0.1 microgram/kg by means of a single base pair reversion. Other mutations can be routinely made in the C terminus to perform this function (Shen et al. *J. Biol. Chem.* 269(46):29077-29084, 1994). They are: F530A; K526A; N524A; V523A; K516A Y514A. A clone having a single point mutation in DT reducing toxicity by 10-100 fold can be made providing that the clone contains an antibody fragment fusion protein, because chemical conjugation of antibody to DT has been shown to reduce systemic wild type toxin toxicity by 100 fold (Neville et al. *J. Biol. Chem.* 264(25):14653-14661, 1989). Therefore, the present invention provides a full length mutant DT sequence with the 525 S to F mutation alone as well as those listed above. These same mutations are also contemplated for the B chain mutant site in DTM2 and can be made similarly. Previous data with chemical conjugation has shown that the longer the C-terminus the better the translocation function (Colombatti et al. *J. Biol. Chem.* 261 (7):3030-3035, 1986). However, the shorter the C-terminus has the less effect of circulating anti-toxin blocking antibodies. Since patients have different levels of blocking antibodies which can be measured, the optimal immunotoxin can be selected for individual patients. scUCHT1 fusion proteins with DTM1 and DT483 (see FIG. 8), DT390 (FIG. 8) and DT370 (FIG. 10) have been cloned and expressed in *E. coli*. Each of these variations as well as the divalent scUCHT1 fusion proteins using each of these toxin domains are provided.

The present invention provides an improvement on CRM197 (a non-toxic toxin mutant described in U.S. Ser. No. 08/034,509, filed Sep. 19, 1994) referred to herein as DTM2. DTM2 has the same mutation as CRM197 plus two mutations in the C-terminus which block binding (see sheet). This is expected to reduce the likelihood of immune complex disease which could result when CRM197 becomes bound to cells and then is further bound by circulating antitoxin. Kidneys are particularly susceptible. DTM2 can not bind to cells thereby lessening the possibility of tissue damage. In addition DTM2 is made for high level production by including the pelB secretory signal for production in *E. coli* or a iron independent mutated promoter DT sequence cloned from CRM9 DNA for production in *C. diptheriae*. The essential feature of DTM2 is the S to F mutation at 525 and the G to E mutation at 52, and a construct containing these two mutations is provided.

All of the constructs reported here can be expressed in *E. coli* using pelB signal sequences or other appropriate signal sequences. Expression can also be carried out in *C. diphtheriae* using appropriate shuttle vectors (Serwold-Davis et al. FEMS Microbiol. Letters 66:119-14, 1990) or in protease deficient strains of *B. subtilis* and using appropriate shuttle vectors (Wu et al. *Bio. Technol.* 11:71, January 1993).

Throughout this application various publications are referenced by numbers within parentheses. Full citations for these publications may be found at the end of the specification immediately preceding the claims. Also, some publications mentioned hereinabove are hereby incorporated in their entirety by reference. The disclosures of these publications in their entireties are hereby incorporated by reference into this application in order to more fully describe the state of the art to which this invention pertains.

While the foregoing invention has been described in some detail for purposes of clarity and understanding, it will be appreciated by one skilled in the art from a reading of this disclosure that various changes in form and detail can be made without departing from the true scope of the invention and appended claims.

EXAMPLE 8

A Fold-Back Single-Chain Diabody Format Enhances the Bioactivity of an Anti-CD3 Recombinant Diphtheria Toxin Based Immunotoxin Anti-CD3 immunotoxins induce profound but transient T cell depletion in vivo by inhibiting eukaryotic protein synthesis, and they have utility in non-human primate models of transplantation tolerance and autoimmune disease therapy (Neville et al., 1992; Hu et al., 1997; Fechner et al., 1997, Thomas et al., 1997 and Contreras et al., 2003). The conjugated immunotoxins were formed by chemically cross-linking the antibody or antibody fragment to a diphtheria toxin binding site mutant, CRM9. In this way the binding site of the immunotoxin was dictated by the antibody moiety (Neville et al., 1996). The disadvantages of these chemically conjugated immunotoxins are linkage heterogeneity, Fc receptor interactions and a mutated toxin-binding domain in which binding to DT receptors is reduced but not eliminated. These disadvantages were overcome by developing recombinant immunotoxins based on diphtheria toxin truncated at residue 390 which provided optimal translocation of the toxin A chain into the cytosol while eliminating the toxin binding domain (Williams et al., 1990 and Thompson et al., 2001). These DT based immunotoxins were restricted to having the antibody moiety placed C-terminal to the truncated toxin because antibody domains fused to the N-terminal of the toxin interfered with translocation of biologically active A chain (Madshus et al., 1992 and Hexam et al., 2001). Although the affinity of anti-CD3 scFv was reduced to 3% of its initial value when tethered to the C-terminus of DT390, this loss was partially compensated by forming a biscFv construct by adding second scFv through a $(G4S)_3$ linker (Thompson et al., 2001). The beneficial effect of the second scFv was ascribed to the divalent character of the biscFv binding, which in the case of the anti-human CD3 antibody UCHT1 was increased 5-fold for the biscFv binding over the scFv binding toward human T cells.

The construction of an anti-monkey CD3 immunotoxin utilizing a biscFv format of an affinity-matured mutant of antibody FN18 known as C207 was recently reported (Wang et al., 2007). Anti-monkey CD3 immunotoxins are important tools in organ transplantation research where the primary goal is to achieve tolerance to allografted organ transplants. Rodents are easily tolerized and are not a good model for human transplantation tolerance protocols compared to monkeys (Fechner et al., 1997, Thomas et al., 1997 and Contreras et al., 2003). The FN18 scFv appeared more sensitive than anti-human UCHT1 to positional loss of affinity when placed distal to the DT390 toxin domains compared to the UCHT1 scFv. The divalent character of the C207 biscFv was judged to be suboptimal as determined by the relatively low increase in binding to monkey T cells of the biscFv relative to the scFv which was only 1.7±0.4 fold, compared to 5-fold for the UCHT1 biscFv/scFv binding ratio. The weaker binding of C207 biscFv could occur through suboptimal associations between the 2 sets of $V_L/V_H$ domains within the biscFv. Thus, a more rigid structure that forced optimal $V_L/V_H$ pairing would produce a higher affinity immunotoxin. The current work explores the use of diabody formats to increase the binding of anti-monkey immunotoxins based on the C207 mutant. Diabodies are recombinant non-covalent dimeric molecules with cross-over pairing of the $V_L$ and $V_H$ domains achieved by linking the $V_L$ and $V_H$ domains with a peptide linker that is too short to allow the interchain assembly of a functional Fv fragment (Holliger et al., 1993). If the linked $V_L$ and $V_H$ domains are derived from the same Fv the diabody will be bivalent. If the linked $V_L$ and $V_H$ domains are derived from two different Fv structures the diabody will be bispecific (Le Gall et al., 2004). These structures spontaneously form non-covalent dimers and are stabilized by the presence of 4 simultaneous variable domain interactions. Single-chain monomeric diabodies have also been generated by linking two diabodies through a longer linker that allows the diabody subunits to fold back head to tail (Kontermann and Muller, 1999).

The initial exploration of anti-monkey CD3 immunotoxin efficacy was done using the continuous cultured monkey T line HSC-F (Akari et al., 1996). Specific cytotoxicity was assayed by the inhibition of protein synthesis. Equilibrium binding studies were also performed in order to determine the correlation between cytotoxicity and immunotoxin T cell binding. Previous studies on the equilibrium binding of anti-CD3 antibodies to T cells and the kinetics of dissociation had revealed a multicomponent binding process consisting of a combination of monovalent and bivalent binding and two equilibrium constants for both monovalent and bivalent binding differing by 10-fold. These were associated with two different dissociation rates also differing by 10-fold (Marano et al., 1989). In order to simplify binding comparisons between antibody fragments and immunotoxins in different formats, equilibrium binding competition studies were performed competing the same labeled tracer, FITC-FN18, and monitor relative binding by the ratios of concentrations at equal tracer displacement. Also cytotoxicity was assayed in resting monkey T cells between different formats. These positive in vivo tests showed that serum clearance was not a limiting factor for in vivo T cell depletion for these new recombinant immunotoxins.

Plasmids, Bacterial and Yeast Strains, Antibodies, Cell Lines.

Plasmid pPICZα was purchased from Invitrogen. The hybridoma secreting FN18 was kindly provided by Dr. Margreet Jonker, Biomedical Primate Research Center Rijswijk, and was produced and purified by the National Cell Culture Center, Minneapolis, Minn. Chemically conjugated anti-monkey CD3 immunotoxin, FN18-CRM9, was prepared as previously described (Neville et al., 1989). The Herpes Saimiri virus transformed cynomolgous cell T cell line HSC-F (Akari et al., 1996) was supplied by the Centralized Facility for AIDS Reagents supported by EU Programme EVA and the UK Medical Research Council. This cell line exhibits the moderate binding FN18 phenotype (Liu et al., 2007).

Protein Synthesis Inhibition Assay.

This was performed by measuring the incorporation of $^3$H-labeled leucine into HSC-F cells after a 20 h exposure to immunotoxins at different concentrations. Means and standard deviations of 6 replicates were calculated and divided by the means of non-immunotoxin treated controls ×100 to give % control protein synthesis as previously described (Thompson et al., 2001).

T Cell Binding Assay of Recombinant scFv Antibodies and Immunotoxins.

FN18-FITC conjugate was purchased from Biosource and added to 250,000 HSC-F cells at $5\times10^{-9}$M in the presence of varying concentrations of scFv and immunotoxin binding competitors at 4° C. for 30 min. The displacement of FN18-FITC was measured by FACS on a Beckman-Coulter Cytomics FC 500 instrument after washing the cells two times at 400×g at 4° C. and resuspending in 0.5 mL of 1×PBS containing 2.5 µg of propidium iodide to exclude dead cells from further analysis. Mean channel fluorescent values, MCI, were corrected (MCF') by subtracting an appropriate FITC-isotope control from both the FN18-FITC tracer, and FN18-FITC tracer plus competitor MCF values. The % inhibition Was determined as $[(MCF'_{FN18\text{-}FITC}-MCF'_{FN18\text{-}FITC+COMPETITOR})/MCF'_{FN18\text{-}FITC}]\times100$. Relative binding affinity between any two competitors was determined by dividing their respective concentrations at equal % inhibition obtained from plots of % inhibition versus concentration as previously described (Thompson et al., 2001).

Immunotoxin Induced Loss of CD3$^+$ CD4$^+$ Resting Monkey T Cells.

T cells from normal monkeys were isolated from blood by two centrifugation through Lymphocyte Separation Medium from BioWhittaker following the manufacturer's directions. About 400,000 cells were washed and incubated in RPMI 1640 medium containing 25 mM HEPES (Gibco) with 10% fetal calf serum+2 g/L NaHCO$_3$, adjusted to pH 7.4, +0.1 mM nonessential amino acids+1.0 mM sodium pyruvate+50 µg/L of gentamicin sulfate with and without varying concentrations of immunotoxins for 72 h at 5% CO$_2$, 37° C. Cells were washed and then stained for 30 min at 4° C. with anti-CD3 (SP34-2-PE BD Pharmingen), anti-CD4-FITC (BD Pharmingen), anti-CD20-PE Cy7 (BD Biosciences), and the vital dye 7-ADD (BD Pharmingen) and analyzed on a Beckman-Coulter Cytomics FC 500 instrument counting $10^4$ events. Cells were analyzed for uptake of the vital dye, the percent of cells within the lymphocyte forward scatter/side scatter gate, and the percent of cells within the lymphocyte gate within the quadrant displaying the CD3$^+$ and CD4$^+$ epitopes by 2-color FACS. The % of cells within the lymphocyte gate at each immunotoxin concentration was divided by % of cells within the lymphocyte gate for the 72 h no-treatment control (G1). The % of cells within the CD3$^+$CD4$^+$ quadrant at each immunotoxin concentration was divided by % of cells within the CD3$^+$CD4$^+$ quadrant for the 72 h no-treatment control (Q1). The % loss of CD3$^+$CD4$^+$ cells was calculated as G1×Q1×100.

Expression and Purification of biscFv(C207) and DT390-biscFv(C207).

C207 is an affinity matured anti-rhesus CD3 mutant antibody selected from a library of FN18 sFvs randomly mutagenized with nucleotide analogs, displayed on yeast and selected by sorting flow cytometry using dye-labeled monkey CD3εγ ectodomain heterodimer (Wang et al., 2007). Construction of biscFv(C207) and its production in *P. pastoris* has been described as has the construction of the diphtheria toxin based immunotoxin utilizing biscFv(C207) (Wang et al., 2007) shown in Table 5 schematic E. In brief, the $V_L$ and $V_H$ domains of C207 were linked by a (G4S)$_3$ linker to form the scFv and two scFvs were linked by third (G4S)$_3$ linker to form the biscFv (Table 5, D).

TABLE 5

Schematic of fusion proteins (A) scFv(C207): VL_{C207} — (G$_4$S)$_3$ — VH_{C207}

(B) Db(C207): VL_{C207} — G$_4$S — VH_{C207}

(C) scfbDb(C207): VL_{C207} — G$_4$S — VH_{C207} — (G$_4$S)$_3$ — VL_{C207} — G$_4$S — VH_{C207}

(D) biscFv(C207): VL_{C207} — (G$_4$S)$_3$ — VL_{C207} — (G$_4$S)$_3$ — VL_{C207} — (G$_4$S)$_3$ — VL_{C207}

(E) A-dmDT390-biscFv(C207): Catalytic domain — Translocation domain — VL_{C207} — (G$_4$S)$_3$ — VH_{C207} — (G$_4$S)$_3$ — VL_{C207} — (G$_4$S)$_3$ — VL_{C207}

(F) A-dmDT390-Db(C207): Catalytic domain — Translocation domain — VL_{C207} — G$_4$S — VH_{C207}

(G) A-dmDT390-scfbDb(C207): Catalytic domain — Translocation domain — VL_{C207} — G$_4$S — VH_{C207} — G$_4$S — VL_{C207} — (G$_4$S)$_3$ — VH_{C207} — G$_4$S — VH_{C207}

Expression and Purification of Diabody (C207) and Fold-Back Diabody (C207) in *P. pastoris*.

For the construction of diabody form of C207, (Table 5, B) the (G$_4$S)$_3$ linker existing between V$_L$ and V$_H$ scFv(C207) (Table 5, A) was replaced with a G$_4$S linker. The scFv(FN18-C207) gene was amplified by PCR using C207 yeast display plasmid as a template DNA and primers GP-095 and WP-052. The primers GP-94, GP-95 and GP-96 are listed in Table 6. (All of the remaining GP and WP primers are listed in Table 1 of Wang et al., 2007.) Sequencing of this vector, pGK1903, was performed using two universal primers, T4 and SP6 located on the TA cloning vector, pDrive (Qiagen). Then, this plasmid was used as a template for the PCR in order to construct Db(C207) (Table 5, B) and scfbDB(C207) (Table 5, C). As described in the previous paper (Wang et al., 2007), the original α-factor signal sequence in the vector system was replaced with a killer toxin (kt) signal peptide in order to have a complete cleavage between the signal peptide sequence and the inserted protein sequences of interest. To obtain diabody (C207), the Db(C207) gene was PCR-amplified from the plasmid pGK1903 using the primers GP-102 and WP-052. These vectors were sequenced using two primers located in the pPICZα, 5'-AOX1 primer and 3'-AOX1 primer (Invitrogen). Expression and purification of diabody (C207) and fold-back diabody (C207) was performed using a protein L affinity resin as described previously (Wang et al., 2007).

Expression and Purification of the Diabody and Fold-Back Diabody Immunotoxins in *P. pastoris*.

To make A-dmDT390-scfbDb(C207), fold-back diabody bivalent immunotoxin, (Table 5, G) the Db(C207) gene was PCR amplified from plasmid pGK1903 using two primer sets; the first amplification used primers GP-94 & WP-053 and second used primers GP-90 & WP-052.

The first PCR product was digested with NcoI and BamHI and the second PCR product was digested with BamHI and EcoRI. Then the two scFv parts in the vector pGK2006 (A-dmDT390-biscFv(C207) in pwPICZα) were sequentially replaced with C207-Db counterparts using NcoI and BamHI for the first scFv and BamHI and EcoRI for the second scFv (see Table 5, G). The resulting plasmid (pGK2019) was transformed into *Pichia pastoris* JW107 and the transformants were selected on YPD plates containing zeocin (100 µg/ml). Because A-dmDT390-scfbDb(C207) expression in strain JW107 was too low to be purified from the induction medium, the expression cassette was moved from pGK2019 to the vector pPIC9K (Invitrogen) by SacI and EcoRI digestion, and then introduced into a new *Pichia pastoris* stain (Liu & Neville, unpublished data) that had a much higher expression level. This new strain, alleviates some of the negative effects of the unfolded protein response that is induced by the expression of certain heterologous proteins in *P. pastoris* (Liu et al., 2005).

To make A-dmDT390-Db(C207) diabody bivalent immunotoxin, Table 5, F the Db(C207) gene from pGK1903 was cut out with NcoI and EcoRI digestion and the 753 bp fragment was purified by gel electrophoresis followed by elution from the gel and then ligated into pGK2019 which was treated with the same restriction enzymes. The resulting plasmid (pGK2017) was transformed into *Pichia pastoris* JW107 and transformants were selected as described above. The vectors for constructing the diabody and fold-back diabody immunotoxins were sequenced using 5'-AOX1 primer, 3'-AOX1 primer (Invitrogen) and two internal primers Reverse 1 and Forward 1 (Table 6). Expression and purification of DT390-Db(C207) was performed as described previously for A-dmDT390-biscFv(C207) (Wang et al., 2007).

TABLE 6

Primer sequence for the construction and sequencing of diabody and diabody-immunotoxin fusion proteins[a]

| Primers | Sequence (5'→3') |
|---|---|
| GP-094 | CTAGC CATGG GGTGG AGGTG GTTCT GACTT TGTTATGTCT CAATC TCC (SEQ ID NO: 7) |
| GP-095 | GAGCA TGCTA GCCAT GGGGT GGAGG TGGCT CTGAC TTTGT TATGT CTCAA TC (SEQ ID NO: 8) |
| GP-096 | CGATG CAATT GGACT TGGGA ACCTC CGCCA CCCTT GATTT CCAAC TTGGT ACC (SEQ ID NO: 9) |
| Reverse 1 | TCCAC CCCAT GGCAA GAATG (SEQ ID NO: 10) |
| Forward I | CCACA ACTCC TACAA CCGTC (SEQ ID NO: 11) |

[a]Restriction sites are underlined.
Boldface indicates the DNA sequences used to integrate a G4S linker.

DT390-scfbDb(C207) Induced T Cell Depletion in Monkeys

A-dmDT390-scfbDb(C207) (Table 5, G) was administered as an intravenous bolus in two dosing schedules; (A) doses given on day 0 and 2 doses at a total dose of 0.15 mg/kg (monkey CX3X) and (B) 8 divided doses given over 4 days, 6 hours apart for a total dose of 0.2 mg/kg (monkey 32972). Lymphocyte phenotype levels were monitored in blood and also in lymph nodes following maceration by flow cytometry on a Beckman-Coulter Cytomics FC 500 instrument counting $10^4$ events. Staining reagents were: $CD3^+$ (CD3 sp34 FITC, Pharmingen, Catalog #556611, clone SP34), $CD4^+$ (CD4 PerCP-Cy5.5, Pharmingen, Catalog #552838, clone L200), $CD8b^+$ (CD8beta ECD, Coulter, Catalog #6607123, clone 2st8.5h7), $CD20^+$ (CD20 PeCy7, BD/Pharmingen, Catalog #335793). Appropriate IgG isotype controls (isotype for sp34: IgG3 FITC, Southern Biotech, Catalog #0105-02, clone B10 and isotype for fn18: IgG1 FITC, Coulter, Catalog #IM0639U, clone 679.1Mc7) were subtracted from mean fluorescent values. Blood T and B cell values were calculated by multiplying the total lymphocyte count per $mm^3$ by the % of T cells or B cells enumerated by flow cytometry. When the total lymphocyte count was not performed on a cytometry day, the count obtained on the previous day was used.

Purity of Fusion Protein Constructs.

Figure 12:
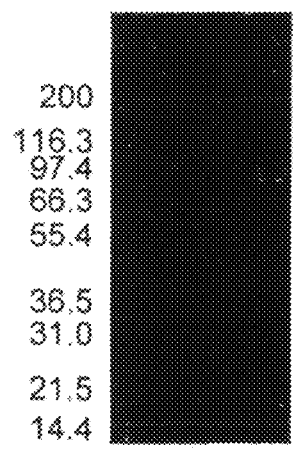
FIG. 12 shows a SDS 12% acrylamide bis-tris non-reducing gel of the fold-back immunotoxin A-dmDT390-scfbDb (C207) (Table 5, G), after the 3-step purification procedure, is shown in third lane from right alongside molecular weight markers in the first lane with marker kDa values printed at the left. (The trace band in the second lane is spillover from lane 3.)

Purified diabody immunotoxin A-dmDT390-Db(C207) (Table 5, F) ran as a single band by SDS-PAGE coincident with A-dmDT390-biscFv(C207) (Table 5, E) (FIG. 12) and gave a major peak on Superdex-200 10/300 GL (Amersham Biosciences) corresponding to the dimeric protein and a small trailing shoulder corresponding to the monomer representing 8.3% of the applied protein in 276 nm absorbance area units. On HPLC size exclusion chromatography on a calibrated Superdex-200 10/300 GL (Amersham Biosciences) 85.7% of the applied purified fold-back immunotoxin A-dmDT390scfbDb(C207) (Table 5, G) eluted coincident with DT390-biscFv (96,500 Da) while 9.7% of the protein eluted corresponding to a molecular weight of 210,000. An additional band, 4.6% eluted at the column front. Since these higher molecular weight species were not seen on the SDS gel it is likely that they correspond to head to tail non-covalent dimers and higher oligomers. The purified diabody Db(C207) (Table 5, B) and the fold-back diabody scfbDb(C207) Table 5, C) both ran as single bands on SDS gels. Their molecular sizes on HPLC are described below.

The Molecular Sizes of Diabody and Fold-Back Diabody Fusion Proteins.

Figure 11:
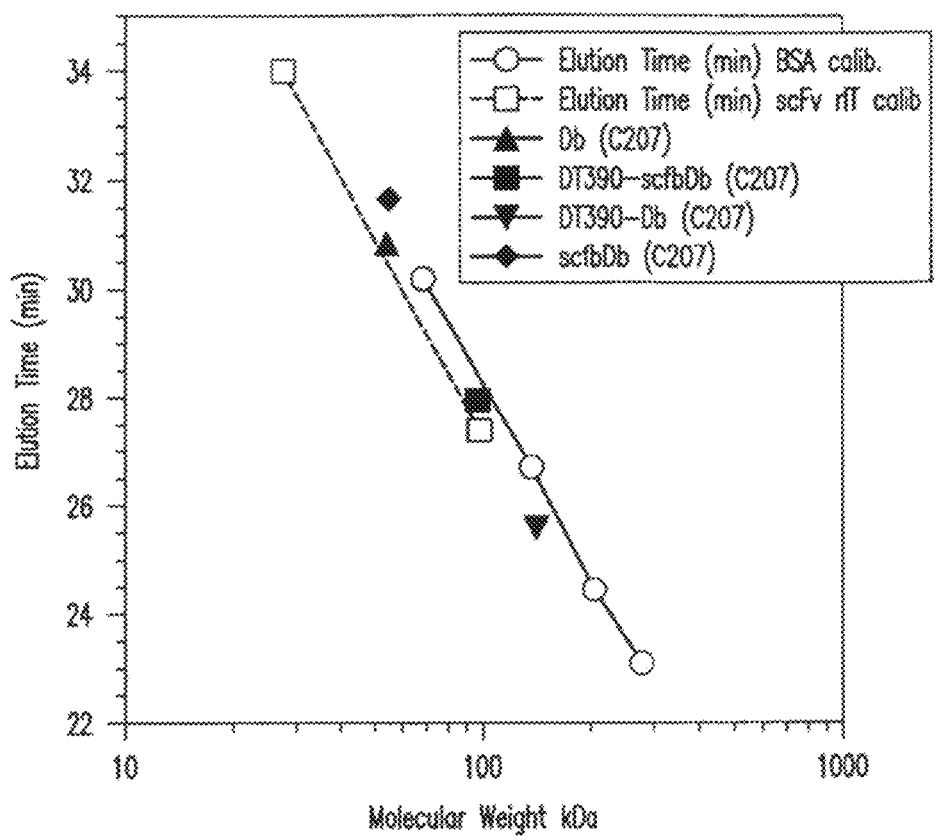
FIG. 11 shows the sizing of the diabody fusion-protein constructs shown in Table 5. The constructs are sized by plotting their elution times versus log MW on a calibrated Superdex 200 size exclusion column. The column has been calibrated with BSA that contains in addition to monomers (68 kDa) dimers, trimers and tetramers (open circles, solid line). Additionally, the column has been calibrated with scFv (M20), 27.5 kDa, and A-dmDT390bisFv(M20), 98.3 kDa, dashed line. The diabody constructs fall on the latter line when given the following molecular weight values: Db(C207), (Table 5, B) solid triangle, 53.7 kDa, calculated MW of [Db(C207)]2; A-dmDT390-scfbDb(C207), (Table 5, E) solid square, 97.1 kDa calculated monomer MW; A-dmDT390-Db(C207), (Table 5, F) inverted solid triangle, 141.1 kDa, calculated MW of [A-dmDT390-Db(C207)]2. The single-chain fold-back diabody, scfbDb(C207), (Table 5, C) solid diamond, having a monomeric MW of 54.6 kDa, elutes slightly above the dashed line indicating a more compact hydrodynamic structure than the corresponding dimeric diabody.

The size of the diabody (Table 5, B) and the diabody immunotoxin (Table 5, F) corresponds to a dimeric protein mediated through molecular associations between the $V_H$ and $V_L$ domains on neighboring molecules since intermolecular self-associations were prevented by the short GIS linker separating these domains. This is shown to be the case in FIG. 11 where the Superdex 200 size exclusion column elution times of these constructs are plotted versus log MW. The column was calibrated using BSA monomers and oligomers (solid line) and with scFv(M20) and A-dmDT390bisFv(M20), dashed line. The point for Db(C207) (Table 5,B), solid triangle, falls on the dashed line when given the calculated MW of the dimer, 53.7 kDa. The point for the diabody immunotoxin (Table 5, F), inverted solid triangle, falls on a linear extension of the dashed line when given the calculated MW of the dimer, 141.1 kDa. In contrast, the fold-back diabody (Table 5, C) and the corresponding fold-back diabody immunotoxin with the longer inter-domain $(G4S)_3$ linkers (Table 5, G) fall on or near the dashed line when given their respective monomer molecular weight values Relative Binding of scFv, Diabody and Single-Chain Fold-Back Diabody Constructs.

Figure 13:
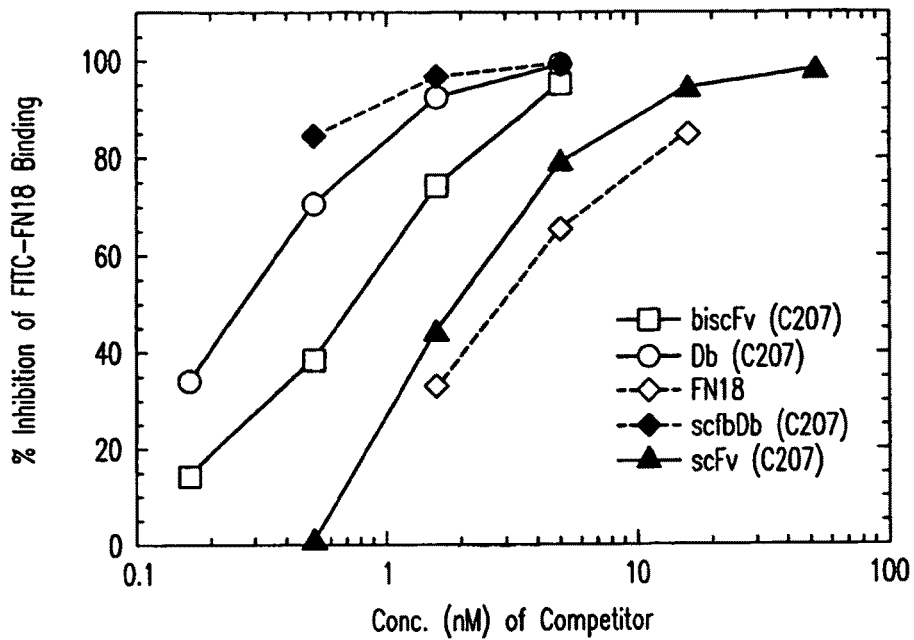
FIG. 13 shows the % inhibition of tracer FITC-labeled FN18 binding to HSC-F monkey T cells plotted versus the concentration of binding competitors consisting of scFv (C207), (Table 5, A) biscFv(C207), the diabody of C207, Db(C207), (Table 5,B) and the single-chain fold-back diabody of C207, scfbDb(C207) (Table 5, C). The relative functional binding affinity for any two competitors can be estimated from the ratio of their concentrations at equal % inhibition values. Estimates are considered to be reliable when comparing parallel curves or parallel curve regions. The rank order of competitor binding from highest to lowest is scfbDb(C207), Db(C207), biscFv(C207) and scFv(C207). FN18 competition for FITC-labeled FN18 is shown for a comparative standard. In replicate assays the ratio of concentrations at equal displacement for Db(C207)/scFv(C207) is 7±2 while the ratio for biscFv(C207)/scFv(C207) is 2.5±0.1 (errors are SD). See Table 5 for structural schematics of these fusion proteins.

The relative binding of these constructs to the monkey T cell line HSC-F is estimated from the inhibition of the anti-monkey anti-T cell antibody FN18 labeled with FITC by the constructs in a competition assay. The ratio of the construct concentrations at equal levels of inhibition reflects the relative avidity of the constructs and is shown in FIG. 13. The rank order of competitor binding from highest to lowest is scfbDb (C207) (Table 5, C), Db(C207) (Table 5, B), biscFv(C207) (Table 5, D) and scFv(C207) (Table 5, A). FN18 competition for FITC-labeled FN18 is shown for a comparative standard. In replicate assays the ratio of concentrations at equal displacement for Db(C207)/scFv(C207) is 7±2 while the ratio for biscFv(C207)/scFv(C207) is 2.5±0.1 (errors are SD).

Relative Binding of Immunotoxin Constructs Made with Scfv, Diabody and a Single-Chain Fold-Back Diabody.

Figure 14:
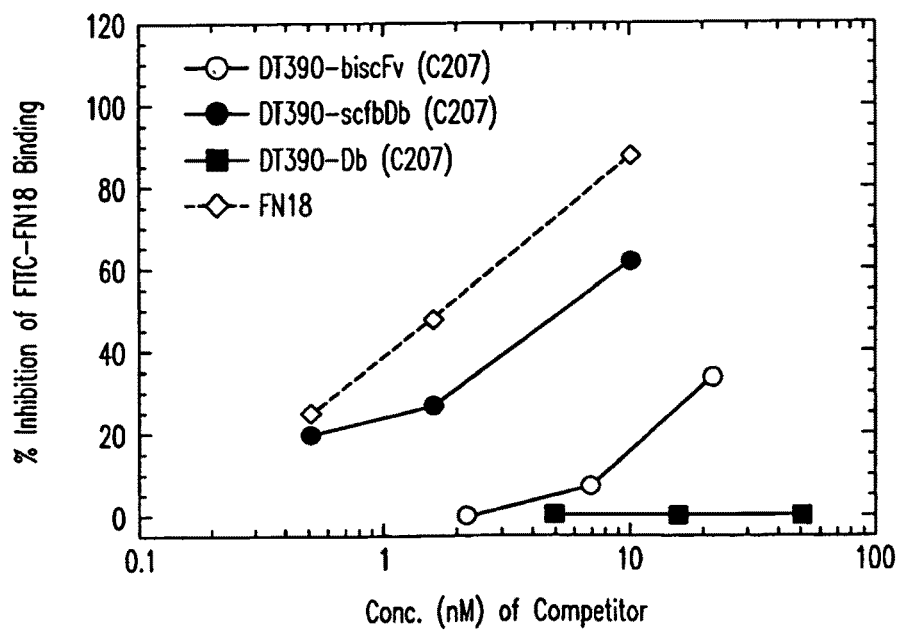
FIG. 14 shows another binding competition assay like FIG. 20 except that the competitors of FITC-labeled FN18 binding to HSC-F monkey T cells are now immunotoxin fusion proteins that use a diabody, A-dmDT390-Db(C207) (Table 5, F), a fold-back single-chain diabody, A-dmDT390-scfbDb (C207) (Table 5, G) and biscFv antibody moiety, A-dmDT390-biscFv(C207) (Table 5, E). The diabody immunotoxin is devoid of detectable binding to the T cells. The fold-back single-chain diabody shows 10-fold increase in binding to T cells compared to A-dmDT390-biscFv(C207). The data points for A-dmDT390-biscFv(C207) are for comparative purposes and were previously reported (Wang et al., 2007).

Although the diabody of C207 (Table 5, B) has high T cell binding, the immunotoxin made in the diabody format (Table 5, F) fails to show demonstrable binding judged by lack of inhibition FN18-FITC binding (solid squares, FIG. 14). In contrast the immunotoxin made in the fold-back diabody format (Table 5, G) exhibits robust binding, solid circles, 10-fold greater than that of the immunotoxin made in the biscFv format, (Table 5, E), empty circles.

Anti-T Cell Activity of Immunotoxin Made in the Fold-Back Diabody Format.

Figure 15:
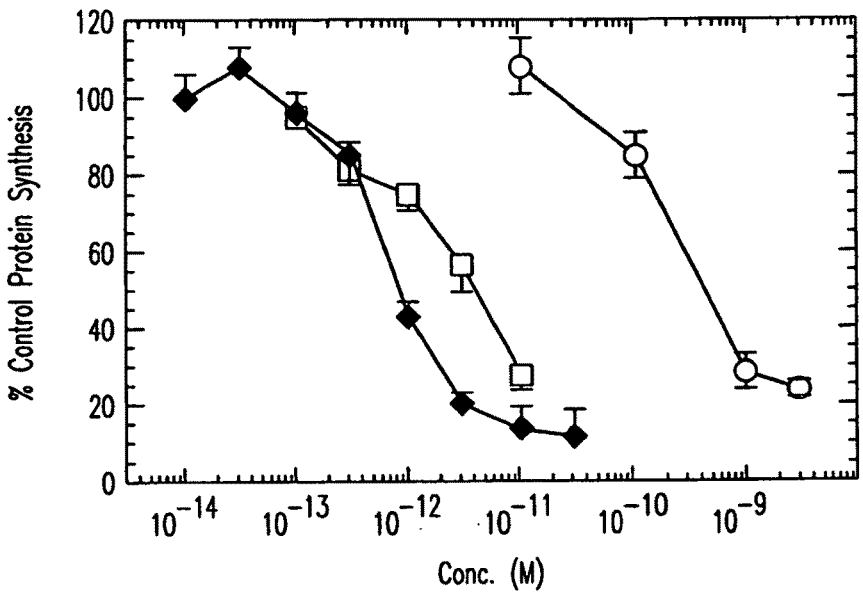
FIG. 15 shows the % control inhibition of protein synthesis for three immunotoxins on HSC-F monkey T cells is plotted versus the immunotoxin concentrations on the x-axis after a 24 h exposure. Each point is the mean of 6 replicates and 1 SD error bars are shown. The single-chain fold-back diabody recombinant immunotoxin, A-dmDT390-scfbDb(C207) (Table 5, G), solid diamonds, is the most potent immunotoxin, exceeding the immunotoxin constructed with the biscFv antibody moiety, A-dmDT390-biscFv(C207) (Table 5, E) by 5-fold (empty squares). Only single sided error bars are shown for these two immunotoxins.
Figure 16:
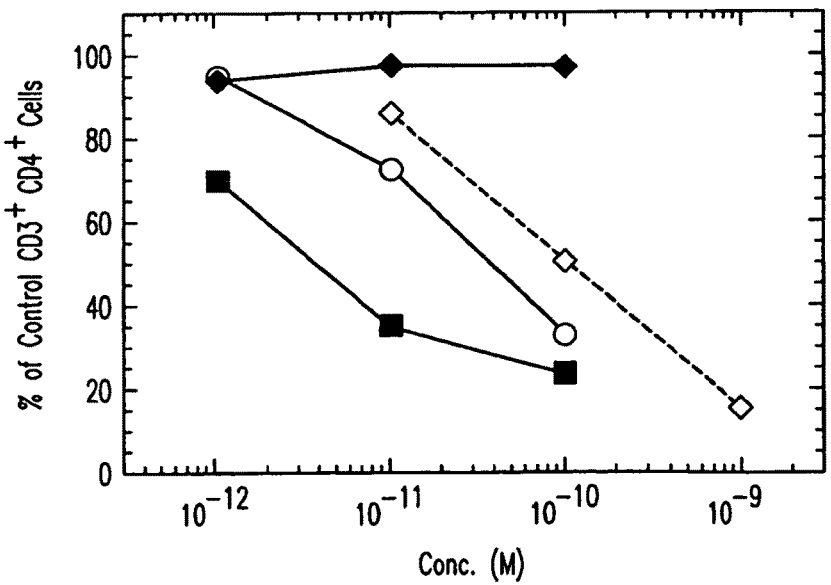
FIG. 16 shows the loss of resting monkey T cells from the lymphocyte gate by flow cytometry. PBMC were isolated from blood by gradient centrifugation and incubated for 72 h with anti-T cell immunotoxins made in various formats. The fold-back diabody immunotoxin, solid squares, is the most potent, exceeding the biscFv immunotoxin, empty circles, by 7±4-fold determined on two replicate assays. The diabody immunotoxin is inactive. Chemically conjugated FN18-CRM9 is provided as a reference.
Figure 17:
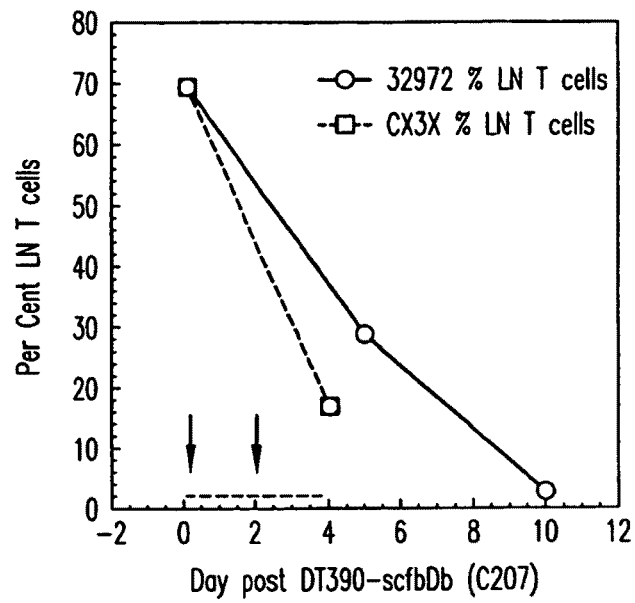
FIG. 17 shows the percent of monkey lymph node $CD3\epsilon^+$T cells present within the forward scatter/side scatter lymphocyte gate determined by flow cytometry after the administration of the fold-back diabody immunotoxin A-dmDT390-scfbDb(C207) (Table 5,G). One monkey, CX3X, dashed line, received an IV bolus of immunotoxin on days 0 and 2 of 75 µg/kg each (arrows). Monkey 32972, solid line, received immunotoxin as an intravenous bolus twice daily, 6 hours apart for 4 days at 25 µg/kg each. Lymph nodes were surgically removed under anesthesia, macerated and stained prior to flow cytometry. The time 0 point represents a mean monkey lymph node T cell percentage from 11 individual monkeys obtained prior to immunotoxin treatment.
Figure 18:
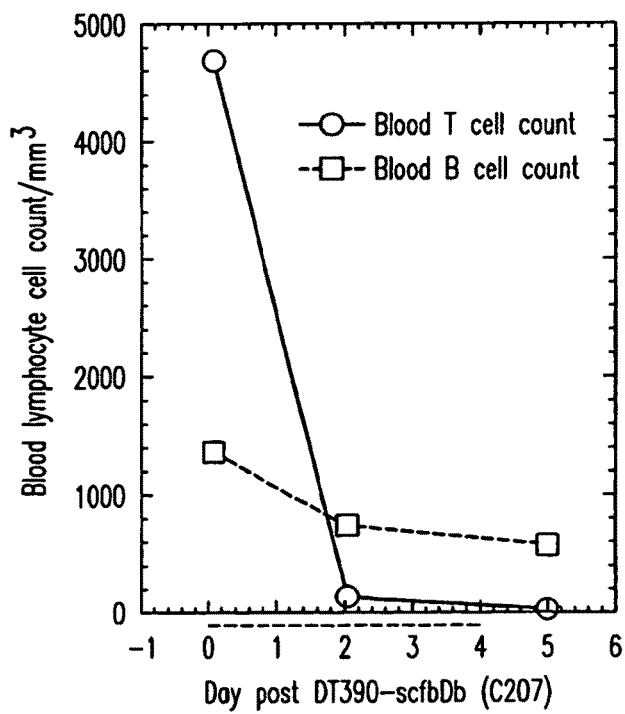
FIG. 18 shows the depletion of blood $CD3\epsilon^+$T cells, solid line, in monkey 32972 and changes in the $CD20^+$ B cell population enumerated by flow cytometry and total blood lymphocyte counts following intravenous administration of the fold-back diabody immunotoxin A-dmDT390-scfbDb (C207) (Table 5, G) [see FIG. 23 legend]. At day 5, after 4 days of immunotoxin administration, the blood T cell count was $19/mm^3$.

The anti-T cell activity of immunotoxin made in the fold-back diabody format was judged by two in vitro assays and by its effects in vivo. In FIG. 15 the % control inhibition of protein synthesis for three immunotoxins on the transformed HSC-F monkey T line is shown. The single-chain fold-back diabody recombinant immunotoxin, A-dmDT390scfbDb (C207) (Table 5, G), solid diamonds, is the most potent immunotoxin, exceeding the immunotoxin constructed with the biscFv antibody moiety, A-dmDT390-biscFv(C207) (Table 5, E) by 5-fold (empty squares). Similar results are shown in FIG. 16 after a 72-hour exposure of immunotoxins to cultured resting monkey T cells isolated from blood. In FIG. 17 the loss of lymph node T cells over time enumerated by flow cytometry following bolus intravenous administration of the fold-back diabody immunotoxin is shown for two monkeys. Monkey 32972 received the immunotoxin twice daily, 6 h apart, over 4 days, for a total dose of 0.2 mg/kg. Monkey CX3X received two intravenous bolus doses of immunotoxin, one on day 0 and one on day 2 for a total dose of 0.15 mg/kg. For a comparison, a third monkey AH44 received another biscFv immunotoxin, A-dmDT390biscFv(M20) in the same dose and schedule as monkey CX3X. This immunotoxin was described previously (Wang et al., 2007) and is 13.5-fold less active against resting T cells compared to A-dmDT390-bis-cFv(C207). Lymph nodes were not noticeably deleted of T cells 4 days after the initial immunotoxin dose. The profound loss of T cells in the blood for monkey 32972 is shown in FIG. 18. B cells are only moderately affected. T cells were present in the blood one month later but the percent of SP34$^+$T cells in the lymphocyte gate was reduced from the pre-treatment value of 66% to 18.7% while the % of CD20$^+$ B cells rose from 19.2 to 35.3 as did the percentage of CD2$^+$ SP34$^-$ cells (probable NK cells).

Discussion

This work shows that a fold-back diabody format for an anti-monkey CD3ε immunotoxin (Table 5, G) offers improvements in binding and bioactivity towards resting T cells and transformed T cell lines ranging from 4 to 10-fold compared to the biscFv format for the affinity matured mutant C207 (Table 5, E). This is a substantial improvement for a therapeutic agent and is consistent with the fact that the fold-back diabody format achieves profound in vivo depletion of T cells in the blood and lymph node compartments when the fold-back immunotoxin is administered twice daily over 4 days (FIGS. 17-18). This is the first report of using a fold-back divalent diabody format in an immunotoxin. Krauss et al. (2005) used a diabody format in an RNAase based immunotoxin targeted at B cells using the CD22 epitope. However, the results showed that the dimeric diabody format was inactive using the larger DT390 based toxin moiety, probably due to steric hindrance. Therefore a fold-back diabody format was tried. In this format two identical diabodies are linked through a longer linker that allows the diabody subunits to fold back head to tail.

There are a number of papers that compare the increase in functional affinity (avidity) on going from a scFv format to a divalent diabody format. In general, the increased functional affinity in the diabody format is the result of a decrease in the equilibrium dissociation constant ($K_D$) and is due to bivalent binding as demonstrated by using methods that independently can measure monovalent and bivalent $K_D$ values. Under most conditions of diabody binding to a protein antigen there exist two measurable $K_D$s, one for monovalent and one for bivalent binding and the overall avidity is determined by the fraction of bivalent binding (Huang et al., 2006). Because of steric constraints in diabody-protein bivalent binding, the fraction of multivalent binding never approaches the high values seen in some low molecular weight systems such as tris-vancomycin binding a trivalent D-Ala-D-Ala ligand (Rao et al., 1998). In this case the trivalent $K_D$ ($4\times10^{-17}$ M) was approximately equal to the third power of the monovalent $K_D$ ($1.6\times10^{-6}$ M).

The fold-back divalent diabody shares the divalent diabody features of enhanced rigidity and a close to 180 degree angle between the two antigen sites and these features contribute to enhanced improvements over the biscFv format. The simultaneous and concerted interaction of all 4 domains undoubtedly stabilizes the structure and provides extra thermal stability compared to the biscFv format where only 2 concerted domain interactions occur for each part of the biscFv. The rigid 180 degree angle between the two antigen sites permits divalent interactions between monovalently bound diabody-immunotoxin on neighboring cells in closely packed tissue such as lymph nodes, thus expanding the fraction of divalent binding sites beyond that limited on a single cell surface. This decreases the overall kinetic off rate and enhances signaling facilitating endocytosis of immunotoxin.

EXAMPLE 9

Cytotoxicity Data of Recombinant Anti-PSMA Immunotoxins

Prostate cancer is the most common non-skin neoplasm in men in the United States with 250,000 cases per year and is the second leading cause of cancer mortality in men with 30,000 deaths per year. One in six men will develop prostate cancer at some point in their lives. The disease is more common in older men and those of African-American ancestry and those with first-degree relatives with prostate cancer. Environmental factors including a high animal fat diet and low selenium and vitamin D may contribute to the high rate of disease in the United States.

Because of the location of the prostate gland and the propensity for cancer to originate in the peripheral zone of the organ, symptoms are often limited until late in disease progression. The symptoms are often nonspecific for cancer and include urinary hesitancy, nocturia, urgency, diminished urinary stream and incomplete bladder emptying. These symptoms may occur with local benign prostate hyperplasia (BPH) as well. Once pelvic or bone pain occurs, prostate cancer has spread and treatments are only palliative.

The molecular mechanisms leading to prostate carcinogenesis appear to be multiple and diverse. Disorders in cell renewal (sonic hedgehog, Notch and Wnt pathways), cell survival (PTEN and Ras signaling) and cell proliferation (MAPK pathways) may all been shown to contribute to prostate cancer formation and progression. Thus, there are multiple targets for new therapeutics, but the role of particular molecules in individual prostate cancer patients is unknown and unlikely to be solitary.

New therapeutics agents for prostate cancer may nevertheless take advantage of the persistence of several prostate differentiation antigens in most metastatic tumor deposits. The cell surface membrane 100 kilodalton glycoprotein prostate specific membrane antigen (PSMA) is expressed on epithelial prostate cells on both the prostate and all stages of androgen-insensitive or metastatic disease. The antigen is an enzyme and forms a homodimer on the cell surface and undergoes rapid endocytosis on antibody binding. The protein is absent from non-prostate tissues.

Figure 19A:
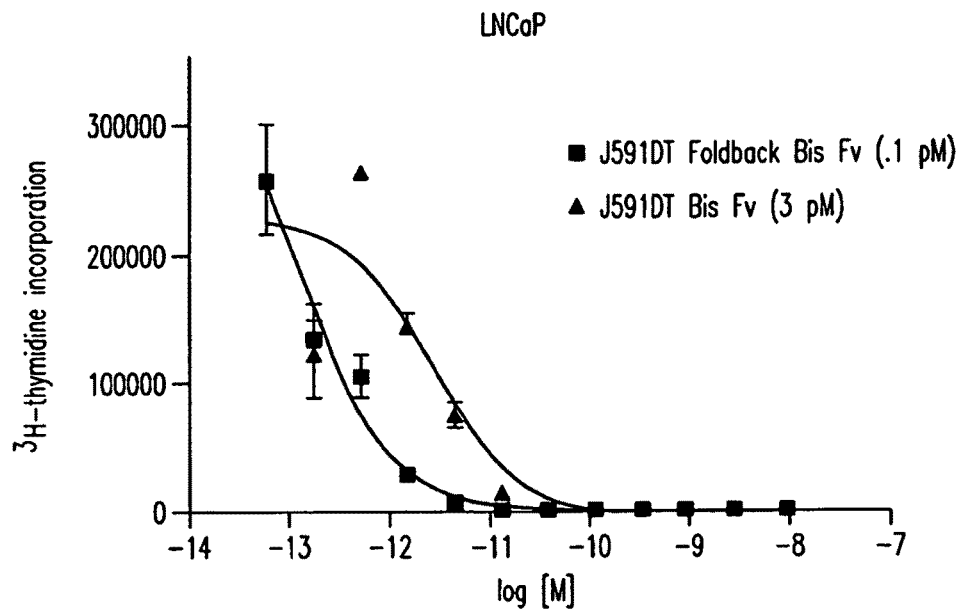
FIG. 19 shows the fold back format anti-PSMA immunotoxin was 18~30 fold more potent than the bisFv format immunotoxin.
Figure 19B:
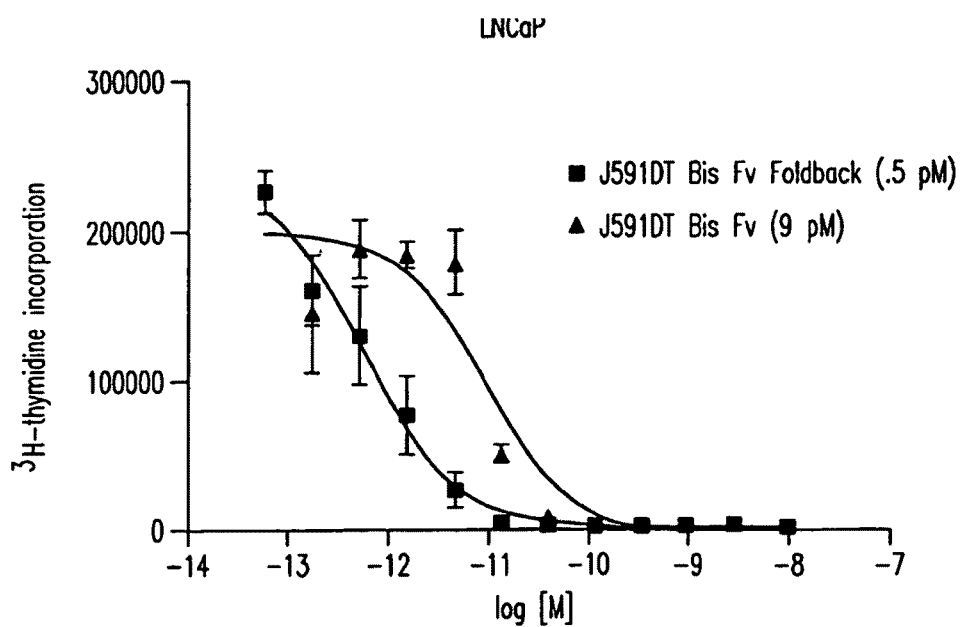

Using single chain Fv fragment of murine J591 anti-PSMA monoclonal antibody, recombinant fold-back format and bisFv format anti-PSMA immunotoxins were prepared in *Pichia pastoris* (see Table 7). Biological potency of fold-back format and bisFv format anti-PSMA immunotoxins was assayed with LNCaPs prostate carcinoma cells obtained from ATCC. Cells were maintained in RPMI 1640, 10% Fetal Bovine Serum at 37° C./5% $CO_2$. Duplicate 96-well flat bottomed plates containing $10^4$ LNCaP cells/well were incubated in 100 μL medium and 50 μL serial dilutions of fold-back or bisFv format immunotoxin yielding 0-10,000 pmols final concentration were added. After 48 hours at 37° C./5% $CO_2$, $^3$H-thymidine (Perkin Elmer) in 50 μL of media was added for an additional 18 hours. The cells were then harvested with a Skatron Cell Harvester (Molecular Devices), transferred to a glass fiber mat, and radioactivity gated for $^3$H measured using an LKB liquid scintillation counter (Perkin Elmer). The $IC_{50}$ of the recombinant immunotoxin was calculated with GraphPad Prism software. As shown in FIG. 19, the fold-back format anti-PSMA immunotoxin was 18~30 fold more potent than the bisFv format immunotoxin.

TABLE 7

Schematic of fusion proteins

| | | | (G$_4$S)$_3$ | (G$_4$S)$_3$ | (G$_4$S)$_3$ | |
|---|---|---|---|---|---|---|
| (E) A-dmDT390-biscFv(J591) | Catalytic domain | Translocation domain | VL$_{J591}$ | VH$_{J591}$ | VL$_{J591}$ | VH$_{J591}$ |

| | | | G$_4$S | (G$_4$S)$_3$ | G$_4$S | |
|---|---|---|---|---|---|---|
| (F) A-dmDT390-scfbDbFv(J591) | Catalytic domain | Translocation domain | VL$_{J591}$ | VH$_{J591}$ | VL$_{J591}$ | VH$_{J591}$ |

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. For example, the following United States patents and patent applications are herein incorporated by reference in their entirety: U.S. Pat. Nos. 6,103,235; 6,632,928; 5,916,773; 8,843,409; 6,319,691; 7,045,605; U.S. application Ser. Nos. 11/219,563, 10/296,085; 09/389,565; and 09/959,006.

REFERENCES

1. Nicholls, P. J., et al. (1993) *J Biol Chem* 268, 5302-5308.
2. Neville, D. J. (1987) Ann NY Acad Sci 507, 155-1643.
3. Williams, D. P., Parker, K., Bacha, P., Bishai, W., Borowski, M., Genbauffe, F., Strom, T. B. and Murphy, J. R. (1987) Protein Eng 1, 493-498
4. Johnson, V. G. and Youle, R. J. (1989) J Biol Chem 264, 17739-17744
5. Kreitman, R. J., Chaudhary, V. K., Waldmann, T. A., Hanchard, B., Cranston, B., FitzGerald, D. J. and Pastan, I. (1993) Leukemia 7, 553-562
6. Murphy, J. R. (1988) Cancer Treat Res 37, 123-124
7. Laske, D. W., Ilercil, O., Akbasak, A., Youle, R. J. and Oldfield, E. H. (1994) J Neurosurg 80, 520-526
8. Neville, D. J., Scharff, J. and Srinivasachar, K. (1992) J of Controlled Release 24, 133-141
9. Neville, D. J., Scharff, J. and Srinivasachar, K. (1992) Proc Natl Acad Sci USA 89, 2585-2589
10. Giannini, G., Rappuoli, R. and Ratti, G. (1984) Nucleic Acids Res 12, 4063-4069
11. Chang, T. M. and Neville, D. M. J. (1977) J Biol Chem 252, 1505-1514
12. Neville, D. J., Srinivasachar, K., Stone, R. and Scharff, J. (1989) J Biol Chem 264, 14653-14661
13. Shalaby, M. R., Shepard, H. M., Presta, L., Rodrigues, M. L., Beberley, P. C. L., Feldman, M. and Carter, P. (1992) J Exp Med 175, 217-225
14. Johnson, S, and Bird, R. E. (1991) in Methods in Enzymol, pp. 88-98, Academic Press, Inc., San Diego, Calif.
15. Grimont, F. and Grimont, P. A. D. (1991) in Nucleic acid techniques in bacterial systematics, pp. 252, E. A. G. Stackebrandt M. John Wiley and Sons, LTD, West Sussex, England
16. Esworthy, R. S, and Neville, D. M. J. (1984) J Biol Chem 258, 11496-11504
17. Pelchen-Matthews, A., Armes, J. E., Griffiths, G. and Marsh, M. (1991) J Exp Med 173, 575-578
18. Choe, S., Bennett, M. J., Fujii, G., Curmi, P. M., Kantardjieff, K. A., Collier, R. J. and Eisenberg, D. (1992) Nature 357, 216-222
19. LeMaistre, C. F., Meneghetti, C., Rosenblum, M., Reuben, J., Parker, K., Shaw, J., Deisseroth, A., Woodworth, T. and Parkinson, D. R. (1992) Blood 79, 2547-2554
20. Platanias, L. C., et al. (1994) Leuk Lymphoma 14, 257-262
21. Higashi, K., Asada, H., Kurata, T., Ishikawa, K., Hayami, M., Spriatna, Y., Sutarman, Y. and Yamanishi, K. (1989) J Gen Virol 70, 3171-3176
22. Youle, R. J. and Neville, D. M. J. (1982) J Biol Chem 257, 1598-1601
23. Williams, D. P., Snider, C. E., Strom, T. B. and Murphy, J. R. (1990) J Biol Chem 265, 11885-11889
24 Parlevliet et al. (1992) Transplant Int; 5:234-246.
25 Cosimi et al. (1981) Transplantation; 32:535-9.
26 Jaffers et al. (1986) Transplantation; 41:572-8.
27 Abramowicz et al. (1989) Transplantation; 47:606-8.
28 Burns et al. (1982) J Immunol; 129:1451-7.
29 Parren et al. (1991) Res Immunol; 142:749-63.
30 Waid et al. (1991) Transplant Proc; 23:1062-5.
31 Khazaeli et al. (1994) J Immunotherapy; 15:42-52.
32 Chen C and Okayama H. (1987); Mol Cell Biol 7:2745-52.
33 Slavin-Chiorini et al. (1993) Int J Cancer; 53:97-103.
34 Rigaut K D, Scharff J E, Neville D M Jr. (1995) Eur J Immunol; 25:2077-82.
35 Woodle E S, Thistlethwaite J R, Jolliffe L K, et al. (1992) J Immunol; 148:2756-63.
36 Miller A D, Rosman G J. (1989) BioTechniques 7:980-90.
37 Shu L M, Qi C F, Schlom J, Kashmiri S V S (1993) Proc Natl Acad Sci USA; 90:7995-9.
38 Mosmann T R, Williamson A R (1980) Cell; 20:283-92.
39 Capon D J, Chamow S M, Mordenti J, et al. (1989) Nature 337:525-31.
40 Anand N N, Mandal S, MacKenzie C R, et al. (1991) J Bio Chem 266:21874-9.
41 Sitia R, Neuberger M, Alberini C M, et al. (1990) Cell; 60:781-90.
42 Alberini C M, Bet P, Milstein C, Sitia R. (1990) Nature 347:485-7.
43 Fra A M, Fragioli C, Finazzi D, Sitia R, Alberini C M (1993) The EMBO Journal; 12:4755-61.
44 Wiersma E J, Shulman M J (1995); 154:5265-72.
45 Smith K G, Austyn J M, Hariri G, Beverley P C, Morris P J (1986) Eur J Immunol; 16:478-86.
46 Tax W J, Hermes F F, Willems R W, Capel P J, Koene R A (1984) J Immunol; 133:1185-9.
47 Lynch, R G, Sandor M., Metzger H, ed. Washington D.C.: American Society for Microbiology 1990:305-34.
48 Moretta I, Webb S R, Grossi C E, Lydyard M, Cooper M D. (1977) J Exp Med; 146:184-200.

49. Ferrarini M, Moretta L, Mingari M C, Tonda P, Perris B. (1976) Eur J Immunol; 6:520-1.
50. Mathur A, Lynch R G, Kohler G (1988); J Immunol; 140:143-7.
51. Pricop L, Rabinowich H, Morel P A, Sulica A, Whiteside T L, Herberman R B (1993) Immunol; 151:3018-29.
52. Emara M, Sanfilippo F (1992) Cell Immunol; 144:143-54.
53. Akari, H., Mori, K., Terao, K., Otani, I., Fukasawa, M., Mukai, R., and Yoshikawa, Y., (1996) In vitro immortalization of Old World monkey T lymphocytes with Herpesvirus saimiri: its susceptibility to infection with simian immunodeficiency viruses. *Virology* 218, 382-388.
54. Contreras, J. L., et al. (2003) Stable α- and β-islet cell function after tolerance induction to pancreatic islet allografts in diabetic primates. *Am. J. Transplant.* 3, 128-138.
55. Fechner, J. H. et al. (1997) Split tolerance induced by immunotoxin in a rhesus kidney allograft model. *Transplantation* 63, 1339-1345.
56. Hexham, J. M., Dudas, D., Hugo, R., Thompson, J., King, V., Dowling, C. Neville, D. M. Jr., Digan, M. E., and Lake, P. (2001) Influence of relative binding affinity on efficacy in a panel of anti-CD3 scFv immunotoxins. *Mol. Immunol.* 38, 397-408.
57. Holliger, P., Prospero, T., and Winter, G. (1993) "Diabodies": small bivalent and bispecific antibody fragments. *Proc. Natl. Acad. Sci. U.S.A.* 90, 6444-6448.
58. Hu, H., Stavrou, S., Baker, B. C., Tomatore, C., Scharff, J., Okunieff, P., and Neville, D. M. Jr. (1997) Depletion of T lymphocytes with immunotoxin retards the progress of experimental allergic encephalomyelitis in rhesus monkeys. *Cell. Immunol.* 177, 26-34.
59. Huang, B. C., Davem, S., Kennel, S. J. (2006) Mono and bivalent binding of a scFv and covalent diabody to murine laminin-1 using radioiodinated proteins and SPR measurements: effects on tissue retention in vivo. J. Immunol. Methods 313, 149-160.
60. Kontermann, R. E., and Muller, R. (1999) Intracellular and cell surface displayed single-chain diabodies. *J. Immunol. Methods* 226, 179-188.
61. Krauss, J., Arndt, M. A. E., Vu, B. K., Newton, D. L., Seeber, S., and Rybak, S. M. (2005) Efficient killing of CD22+ tumor cells by a humanized diabody-RNase fusion protein. *Biochem. Biophys. Res. Commun.* 331, 595-602.
62. Le Gall, F., Reusch, U., Little, M., and Kipriyanov, S. M. (2004) Effect of linker sequences between the antibody variable domains on the formation, stability and biological activity of a bispecific tandem diabody. *Protein Eng. Des. Sel.* 17, 357-366.
63. Liu Y. Y., Woo J. H. and Neville D. M. Jr. (2005) Over expression of an anti-CD3 immunotoxin increases the expression and secretion of the molecular chaperone Bip/Kar2p from *Pichia pastoris*. *Applied and Experimental Microbiology* 71, 5332-5340
64. Liu Y. Y., Wang, Z., Thomas, J., Goodwin, K. J., Stavrou, S., Neville, D. M. Jr. (2007) Polymorphisms of CD3ε in cynomolgus and rhesus monkeys and their relevance to anti-CD3 antibodies and immunotoxins. *Immunol. Cell Biol.* February 27; [Epub ahead of print]
65. Madshus, I. H., Olsnes, S., and Stenmark, H. (1992) Membrane translocation of diphtheria toxin carrying passenger protein domains. *Infect. Immun.* 60, 3296-3302.
66. Marano, N., Holowka, D. and Baird, B. (1989) Bivalent binding of an antibody to Jurkat cells induces association of the T cell receptor complex with the cytoskeleton. *J Immunol.* 143, 931-938.
67. Neville, D. M. Jr., Scharff, J., Rigaut, K., Hu, H., Shiloach, J., Slingerland, W., and Jonker, M. (1996) A new reagent for the induction of T cell depletion, anti-CD3-CRM9. *J. Immunother. Emphasis. Tumor Immunol.* 19, 85-92.
68. Nielsen, U. B., Adams, G. P., Weiner, L. M., and Marks, J. D. (2000) Targeting of bivalent anti-ErbB2 diabody antibody fragments to tumor cells is independent of the intrinsic antibody affinity. *Cancer Res.* 60, 6434-6440.
69. Perisic, O., Webb, P. A., Holliger, P., Winter, G., and Williams, R. L. (1994) Crystal structure of a diabody, a bivalent antibody fragment. *Structure* 2, 1217-1226.
70. Rao, J., Lahiri, J., Isaacs, L., Weis, R. M., Whitesides, G. M. (1998) A trivalent system from vancomycin.D-ala-D-Ala with higher affinity than avidin.biotin. *Science* 280, 708-711.
71. Thomas, J. M., et al. (1997) Preclinical studies of allograft tolerance in rhesus monkeys. *Transplantation* 64, 124-135;
72. Thompson, J., et al. (2001) Improved binding of a bivalent single-chain immunotoxin results in increased efficacy for in vivo T-cell depletion. *Protein Eng.* 14, 1035-1041.
73. Wang, Z., et al. (2007) Improvement of a recombinant anti-monkey CD3 diphtheria toxin based immunotoxin by yeast display affinity maturation of the scFv. *Bioconjug. Chem.* 18, 947-955.

SEQUENCES (1) Amino Acid Sequence of A-dmDT390-Foldback-bisFv (J591) (SEQ ID NO:12)
1~391: A-dmDT390
392~393: amino acid residues corresponding to NcoI restriction site
394~500: first VL of J591 antibody
501~505: GGGGS linker
506~620: first VH of J591 antibody
621~635: (G4S)3 linker
636~742: second VL of J591 antibody
743~747: GGGGS linker
748~862: second VH of J591 antibody
394~862: fold-back-bisFv(J591)

```
  1 AGADDVVDSS KSFVMENFAS YHGTKPGYVD SIQKGIQKPK SGTQGNYDDD WKGFYSTDNK  60
 61 YDAAGYSVDN ENPLSGKAGG VVKVTYPGLT KVLALKVDNA ETIKKELGLS LTEPLMEQVG 120
121 TEEFIKRFGD GASRVVLSLP FAEGSSSVEY INNWEQAKAL SVELEINFET RGKRGQDAMY 180
181 EYMAQACAGN RVRRSVGSSL SCINLDWDVI RDKTKTKIES LKEHGPIKNK MSESPAKTVS 240
241 EEKAKQYLEE FHQTALEHPE LSELKTVTGT NPVFAGANYA AWAVNVAQVI DSETADNLEK 300
301 TTAALSILPG IGSVMGIADG AVHHNTEEIV AQSIALSSLM VAQAIPLVGE LVDIGFAAYN 360
361 FVESIINLFQ VVHNSYNRPA YSPGHKTQPF LPWDIVMTQS HKFMSTSVGD RVSIICKASQ 420
```

```
421 DVGTAVDWYQ QKPGQSPKLL IYWASTRHTG VPDRFTGSGS GTDFTLTITN VQSEDLADYF 480
481 CQQYNSYPLT FGAGTMLDLK GGGGSEVQLQ QSGPELKKPG TSVRISCKTS GYTFTEYTIH 540
541 WVKQSHGKSL EWIGNINPNN GGTTYNQKFE DKATLTVDKS SSTAYMELRS LTSEDSAVYY 600
601 CAAGWNFDYW GQGTTLTVSS GGGGSGGGGS GGGGSDIVMT QSHKFMSTSV GDRVSIICKA 660
661 SQDVGTAVDW YQQKPGQSPK LLIYWASTRH TGVPDRFTGS GSGTDFTLTI TNVQSEDLAD 720
721 YFCQQYNSYP LTFGAGTMLD LKGGGGSEVQ LQQSGPELKK PGTSVRISCK TSGYTFTEYT 780
781 IHWVKQSHGK SLEWIGNINP NNGGTTYNQK FEDKATLTVD KSSSTAYMEL RSLTSEDSAV 840
841 YYCAAGWNFD YWGQGTTLTV SS
```

(2) DNA Sequences of A-dmDT390-Foldback-bisFv(J591) (SEQ ID NO:13)
  1~1173: DNA sequence coding for A-dmDT390
  1174~1179: NcoI restriction enzyme site
  1180~2592: DNA sequence coding for fold-back-bisFv (J591)
  2593~2595: Stop codon

```
   1 GCTGGTGCTG ACGACGTCGT CGACTCCTCC AAGTCCTTCG TCATGGAGAA
  51 CTTCGCTTCC TACCACGGGA CCAAGCCAGG TTACGTCGAC TCCATCCAGA
 101 AGGGTATCCA GAAGCCAAAG TCCGGCACCC AAGGTAACTA CGACGACGAC
 151 TGGAAGGGGT CTACTCCAC CGACAACAAG TACGACGCTG CGGGATACTC
 201 TGTAGATAAT GAAAACCCGC TCTCTGGAAA AGCTGGAGGC GTGGTCAAGG
 251 TCACCTACCC AGGTCTGACT AAGGTCTTGG CTTTGAAGGT CGACAACGCT
 301 GAGACCATCA AGAAGGAGTT GGGTTTGTCC TTGACTGAGC CATTGATGGA
 351 GCAAGTCGGT ACCGAAGAGT TCATCAAGAG ATTCGGTGAC GGTGCTTCCA
 401 GAGTCGTCTT GTCCTTGCCA TTCGCTGAGG GTTCTTCTAG CGTTGAATAT
 451 ATTAATAACT GGGAACAGGC TAAGGCTTTG TCTGTTGAAT GGAGATTAA
 501 CTTCGAAACC AGAGGTAAGA GAGGTCAAGA TGCGATGTAT GAGTATATGG
 551 CTCAAGCCTG TGCTGGTAAC AGAGTCAGAC GTTCTGTTGG TTCCTCTTTG
 601 TCCTGTATCA ACCTAGACTG GGACGTCATC AGAGACAAGA CTAAGACCAA
 651 GATCGAGTCT TTGAAAGAGC ATGGCCCAAT CAAGAACAAG ATGTCCGAAT
 701 CCCCCGCTAA GACCGTCTCC GAGGAAAAGG CCAAGCAATA CCTAGAAGAG
 751 TTCCACCAAA CCGCCTTGGA GCATCCTGAA TTGTCAGAAC TTAAAACCGT
 801 TACTGGGACC AATCCTGTAT TCGCTGGGGC TAACTATGCG GCGTGGGCAG
 851 TAAACGTTGC GCAAGTTATC GATAGCGAAA CAGCTGATAA TTTGGAAAAG
 901 ACAACTGCTG CTCTTTCGAT ACTTCCTGGT ATCGGTAGCG TAATGGGCAT
 951 TGCAGACGGT GCCGTTCACC ACAATACAGA AGAGATAGTG GCACAATCCA
1001 TCGCTTTGTC CTCTTTGATG GTTGCTCAAG CTATCCCATT GGTCGGTGAG
1051 TTGGTTGACA TCGGTTTCGC TGCCTACAAC TTCGTCGAGT CCATCATCAA
1101 CTTGTTCCAA GTCGTCCACA ACTCCTACAA CCGTCCGGCT TACTCCCCAG
1151 GTCACAAGAC CCAACCATTC TTGCCATGGC CATGGGATAT TGTTATGACT
1201 CAATCTCATA AGTTCATGTC CACTTCCGTC GGTGATAGAG TCTCTATTAT
1251 TTGTAAGGCT TCTCAGGACG TCGGTACTGC TGTTGATTGG TATCAACAAA
1301 AGCCAGGTCA ATCTCCAAAG TTGTTGATTT ACTGGGCTTC TACTAGACAT
1351 ACTGGTGTTC CAGATAGATT CACTGGTTCT GGTTCTGGTA CTGATTTCAC
```

-continued

```
1401 CTTGACTATC ACTAACGTCC AGTCTGAGGA CTTGGCTGAC TACTTCTGCC
1451 AGCAGTACAA CTCTTACCCA TTGACTTTCG GTGCTGGAAC CATGTTGGAT
1501 TTGAAGGGTG GAGGTGGATC TGAGGTCCAG TTGCAGCAAT CTGGACCAGA
1551 GTTGAAGAAG CCAGGTACTT CTGTCAGAAT TCTTGTAAG ACTTCTGGTT
1601 ACACTTTCAC TGAGTACACT ATTCATTGGG TTAAGCAATC TCATGGTAAG
1651 TCTTTGGAGT GGATTGGAAA CATCAACCCA ACAACGGTG GAACTACCTA
1701 CAACCAAAAG TTCGAGGATA AGGCTACTTT GACTGTTGAT AAGTCTTCTT
1751 CCACTGCTTA CATGGAATTG AGATCCTTGA CCTCTGAGGA TTCCGCTGTC
1801 TACTACTGTG CTGCTGGTTG GAACTTCGAT TACTGGGGAC AAGGAACCAC
1851 TTTGACTGTT TCCTCTGGAG GTGGCGGGTC TGGTGGAGGC GGATCCGGAG
1901 GTGGCGGATC TGATATTGTT ATGACTCAAT CTCATAAGTT CATGTCCACT
1951 TCCGTCGGTG ATAGAGTCTC TATTATTTGT AAGGCTTCTC AGGACGTCGG
2001 TACTGCTGTT GATTGGTATC AACAAAAGCC AGGTCAATCT CCAAAGTTGT
2051 TGATTTACTG GGCTTCTACT AGACATACTG GTGTTCCAGA TAGATTCACT
2101 GGTTCTGGTT CTGGTACTGA TTTCACCTTG ACTATCACTA ACGTCCAGTC
2151 TGAGGACTTG GCTGACTACT TCTGCCAGCA GTACAACTCT TACCCATTGA
2201 CTTTCGGTGC TGGAACCATG TTGGATTTGA AGGGTGGAGG TGGATCTGAG
2251 GTCCAGTTGC AGCAATCTGG ACCAGAGTTG AAGAAGCCAG GTACTTCTGT
2301 CAGAATTTCT TGTAAGACTT CTGGTTACAC TTTCACTGAG TACACTATTC
2351 ATTGGGTTAA GCAATCTCAT GGTAAGTCTT TGGAGTGGAT TGGAAACATC
2401 AACCCAAACA ACGGTGGAAC TACCTACAAC CAAAAGTTCG AGGATAAGGC
2451 TACTTTGACT GTTGATAAGT CTTCTTCCAC TGCTTACATG GAATTGAGAT
2501 CCTTGACCTC TGAGGATTCC GCTGTCTACT ACTGTGCTGC TGGTTGGAAC
2551 TTCGATTACT GGGGACAAGG AACCACTTTG ACTGTTTCCT CTTAA
```

40

C207 scFv Diabody DNA Sequence [G4S-VL-G4S-VH-(G4S)3-VL-G4S-VH] (SEQ ID NO:14)

```
GGTGGAGGTGGCTCTGACTTTGTTATGTCTCAATCTCCATCCTCCTTGGCTGTTTCTGTTGGTGAG
AGGGTTACTATGTCTTGTAAGTCCTCTCAATCTTTGTTGTACTTTTCTAACCGAAAGAACTACTTG
GCTTGGTACCAACAAAAGCCAGGTCAATCTCCTAAGTTGTTGATTAACTGGGCTTCCACCAGAGA
ATCTGGTGTCCCTGACAGATTCACTGGTTCTGGTTCTAGAACTGACTTCACTTTGACCATCTCTTC
TGTTAAGGCTGAAGACTTGGCTGTTTACTTCTGTCAACAATTCTACTCTTACCCTCCAACTTTCGG
TGGTGGTACCAAGTTGGAAATCAAGGGTGGCGGAGGTTCCCAAGTCCAATTGCAACAATCTGAA
GCTGAATTGGCTAGACCTGGTGCTTCTGTTAAGATGTCCTGTAAGGCTTCTGGTTACACCTTCACT
GACTACACTATCCACTGGTTGAGGCAAAAACCTGGTCAAGGTTTGGACTGGATTGGTTACTTCAA
CCCTTCTTCTGGATCTACTGAATACAACAGAAAGTTCAAGGACAGAACCATTTTGACTGCTGACA
GATCCTCTACCACTGTTTACATGCAATTGTCTTCTTTGACTTCTGAGGACTCTGCTGTCTACTACT
GTGCTAGAAAGGGTGAGAAGTTGTTGGGTAACAGATACTGGTACTTCGACGTCTGGGGTGCTGGT
ACCTCTGTCACCGTCTCCTCTGGAGGCGGAGGCAGCGGAGGCGGTGGATCCGGAGGGGGAGGCT
CGGACTTTGTTATGTCTCAATCTCCATCCTCCTTGGCTGTTTCTGTTGGTGAGAGGGTTACTATGT
CTTGTAAGTCCTCTCAATCTTTGTTGTACTTTTCTAACCGAAAGAACTACTTGGCTTGGTACCAAC
```

-continued

AAAAGCCAGGTCAATCTCCTAAGTTGTTGATTAACTGGGCTTCCACCAGAGAATCTGGTGTCCCT

GACAGATTCACTGGTTCTGGTTCTAGAACTGACTTCACTTTGACCATCTCTTCTGTTAAGGCTGAA

GACTTGGCTGTTTACTTCTGTCAACAATTCTACTCTTACCCTCCAACTTTCGGTGGTGGTACCAAG

TTGGAAATCAAGGGTGGCGGAGGTTCCCAAGTCCAATTGCAACAATCTGAAGCTGAATTGGCTAG

ACCTGGTGCTTCTGTTAAGATGTCCTGTAAGGCTTCTGGTTACACCTTCACTGACTACACTATCCA

CTGGTTGAGGCAAAAACCTGGTCAAGGTTTGGACTGGATTGGTTACTTCAACCCTTCTTCTGGAT

CTACTGAATACAACAGAAAGTTCAAGGACAGAACCATTTTGACTGCTGACAGATCCTCTACCACT

GTTTACATGCAATTGTCTTCTTTGACTTCTGAGGACTCTGCTGTCTACTACTGTGCTAGAAAGGGT

GAGAAGTTGTTGGGTAACAGATACTGGTACTTCGACGTCTGGGGTGCTGGTACCTCTGTCACCGT

CTCCTCT

C207 scFv Diabody AA Sequence [G4S-VL-G4S-VH-(G4S)3-VL-G4S-VH] (SEQ ID NO:15)

GGGGSDFVMSQSPSSLAVSVGERVTMSCKSSQSLLYFSNRKNYLAWYQQKPGQSPKLLINWASTRES

GVPDRFTGSGSRTDFTLTISSVKAEDLAVYFCQQFYSYPPTFGGGTKLEIKGGGGSQVQLQQSEAELA

RPGASVKMSCKASGYTFTDYTIHWLRQKPGQGLDWIGYFNPSSGSTEYNRKFKDRTILTADRSSTTV

YMQLSSLTSEDSAVYYCARKGEKLLGNRYWYFDVWGAGTSVTVSSGGGGSGGGGSGGGGSDFVMS

QSPSSLAVSVGERVTMSCKSSQSLLYFSNRKNYLAWYQQKPGQSPKLLINWASTRESGVPDRFTGSGS

RTDFTLTISSVKAEDLAVYFCQQFYSYPPTFGGGTKLEIKGGGGSQVQLQQSEAELARPGASVKMSCK

ASGYTFTDYTIHWLRQKPGQGLDWIGYFNPSSGSTEYNRKFKDRTILTADRSSTTVYMQLSSLTSEDS

AVYYCARKGEKLLGNRYWYFDVWGAGTSVTVSS

What is claimed is:

1. An immunotoxin fusion protein produced in *Pichia pastoris*, comprising a mutant diphtheria toxin moiety and a targeting moiety, wherein the targeting moiety is a single chain variable region bivalent diabody comprising a first scFv and a second scFv, wherein said first scFv and said second scFv share the same antigen specificity, and wherein the diabody comprises an anti-PSMA $V_L V_H$ region.

2. The immunotoxin of claim 1, wherein the diabody is a fold-back diabody.

3. The immunotoxin of claim 1, wherein the diabody anti-PSMA $V_L V_H$ region comprises the J591 $V_L V_H$ region.

4. The immunotoxin of claim 1, wherein the toxin moiety is a truncation mutant.

5. The immunotoxin of claim 4, wherein the truncation mutant comprises a deletion of 140, 141, 142, 143, 144, 145, 146, 147, 148, 149, or 150 C-terminal amino acids of the full length diphtheria toxin.

6. The immunotoxin of claim 4, wherein the immunotoxin is A-dmDT390scfbDb(J591).

7. The immunotoxin of claim 6, wherein the immunotoxin is A-dmDT390scfbDb(J591) where the furin site amino acid sequence cleavage site RVRRSV (SEQ ID NO: 24) has been replaced with the MMP cleavage site GPLGMLSQ (SEQ ID NO: 25).

8. The immunotoxin of claim 6, wherein the immunotoxin is A-dmDT390scfbDb(J591) where the furin cleavage site amino acid sequence RVRRSV (SEQ ID NO: 24) has been replaced with the PSA cleavage site HSSKLQ (SEQ ID NO: 26).

9. An immunotoxin fusion protein comprising a diphtheria toxin moiety and a targeting moiety, wherein the targeting moiety is a diabody, wherein said diabody comprises a first scFv and a second scFv, wherein said first scFv and said second scFv share the same antigen specificity, wherein the sequence from the amino terminus from left to right is toxin moiety $V_{L1}$, $L_2$, $V_{H1}$, $L_3$, $V_{L2}$, $L_4$, $V_{H2}$, wherein the toxin moiety comprises a truncation mutation $L_2$ and $L_4$ are $(G_4S)$ linkers, $L_3$ is a $(G_4S)_3$ linker, and $V_L$ and $V_H$ are the variable light and heavy domains, wherein the $V_{L1}$ and $V_{H1}$ comprise the $V_L V_H$ region of an anti-PSMA antibody.

10. The immunotoxin of claim 9, wherein the diabody is a fold-back diabody.

11. The immunotoxin of claim 9, wherein the anti-PSMA antibody is J591.

12. The immunotoxin of claim 9, wherein $V_{L1}$ and $V_{H1}$ are the same as $V_{L2}$ and $V_{H2}$.

13. The immunotoxin of claim 9, wherein the toxin moiety is a truncation mutant.

14. The immunotoxin of claim 13, wherein the truncation mutant comprises a deletion of 140, 141, 142, 143, 144, 145, 146, 147, 148, 149, or 150, C-terminal amino acids of the full length diphtheria toxin.

15. The immunotoxin of claim 1, wherein the diabody is not a fold-back diabody.

16. An immunotoxin, comprising a mutant diphtheria toxin moiety linked to a targeting moiety, wherein the targeting moiety is a single chain variable region diabody, and wherein the immunotoxin is AdmDT390scfbDb(J591) where the furin site amino acid sequence cleavage site RVRRSV (SEQ ID NO: 24) has been replaced with the MMP cleavage site GPLGMLSQ (SEQ ID NO: 25).

17. The immunotoxin of claim 16, wherein the mutant diphtheria toxin moiety is a truncation mutant.

18. An immunotoxin fusion protein comprising a diphtheria toxin moiety and a targeting moiety, wherein the targeting moiety is a diabody, wherein the sequence from the amino terminus from left to right is toxin moiety,$V_{L1}$, $L_2$, $V_{H1}$, $L_3$, $V_{L2}$, $L_4$, $V_{H2}$, wherein the toxin moiety comprises a truncation mutation, $L_2$, $L_3$ and $L_4$ are $(G_4S)_3$ linkers, and $V_L$ and $V_H$ are the variable light and heavy domains, wherein the $V_{L1}$ and $V_{H1}$ comprise the $V_L V_H$ region of an anti-PSMA antibody, and wherein the $V_{L1}$ and $V_{H1}$ and the $V_{L2}$ and $V_{H2}$ share the same antigen specificity.

* * * * *

```
                              SEQUENCE LISTING

<160> NUMBER OF SEQ ID NOS: 26

<210> SEQ ID NO 1
<211> LENGTH: 67
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 1
atgaaatacc tattgcctac ggcagccgct ggattgttat tactgcgctg cccaaccagc      60
gatggcc                                                                67

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 2
atgaaatacc tattgcctac ggcagccgct ggattgttat tactcgctgc ccaa             54

<210> SEQ ID NO 3
<211> LENGTH: 59
<212> TYPE: DNA
```

<213> ORGANISM: Artificial Sequence
<220> FEATURE:
<223> OTHER INFORMATION: Description of Artificial Sequence; note = synthetic construct

<400> SEQUENCE: 3
ggattgttat tactcgctgc ccaacaagcg atggccggcg ctgatgatgt tgttgattc    59

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence; note = synthetic construct

<400> SEQUENCE: 4
cggtactata aaactctttc caatcatcgt c                                  31

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence; note = synthetic construct

<400> SEQUENCE: 5
gacgatgatt ggaaagagtt ttatagtacc g                                  31

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence; note = synthetic construct

<400> SEQUENCE: 6
agatctgtcg actcatcagc ttttgatttc aaaaaatagc g                       41

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence; note = synthetic construct

<400> SEQUENCE: 7
ctagccatgg ggtggaggtg gttctgactt tgttatgtct caatctcc                48

<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence; note = synthetic construct

<400> SEQUENCE: 8
gagcatgcta gccatggggt ggaggtggct ctgactttgt tatgtctcaa tc           52

<210> SEQ ID NO 9
<211> LENGTH: 53
<212> TYPE: DNA
<213> ORGANISM: Artificial Sequence -continued

```
<220> FEATURE:
<223> OTHER INFORMATION: Description of Artificial Sequence; note =
      synthetic construct

<400> SEQUENCE: 9
cgatgcaatt ggacttggga acctccgcca cccttgattt ccaacttggt acc         53

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 10
tccaccccat ggcaagaatg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 11
ccacaactcc tacaaccgtc                                              20

<210> SEQ ID NO 12
<211> LENGTH: 862
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 12
```

Ala Gly Ala Asp Asp Val Val Asp Ser Ser Lys Ser Phe Val Met Glu
 1               5                  10                  15

Asn Phe Ala Ser Tyr His Gly Thr Lys Pro Gly Tyr Val Asp Ser Ile
             20                  25                  30

Gln Lys Gly Ile Gln Lys Pro Lys Ser Gly Thr Gln Gly Asn Tyr Asp
         35                  40                  45

Asp Asp Trp Lys Gly Phe Tyr Ser Thr Asp Asn Lys Tyr Asp Ala Ala
     50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Gly Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val

-continued

```
                180                 185                 190
Arg Arg Ser Val Gly Ser Ser Leu Ser Cys Ile Asn Leu Asp Trp Asp
            195                 200                 205
Val Ile Arg Asp Lys Thr Lys Thr Lys Ile Glu Ser Leu Lys Glu His
            210                 215                 220
Gly Pro Ile Lys Asn Lys Met Ser Glu Ser Pro Ala Lys Thr Val Ser
225                 230                 235                 240
Glu Glu Lys Ala Lys Gln Tyr Leu Glu Glu Phe His Gln Thr Ala Leu
                245                 250                 255
Glu His Pro Glu Leu Ser Glu Leu Lys Thr Val Thr Gly Thr Asn Pro
            260                 265                 270
Val Phe Ala Gly Ala Asn Tyr Ala Ala Trp Ala Val Asn Val Ala Gln
            275                 280                 285
Val Ile Asp Ser Glu Thr Ala Asp Asn Leu Glu Lys Thr Thr Ala Ala
            290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                325                 330                 335
Ser Ser Leu Met Val Ala Gln Ala Ile Pro Leu Val Gly Glu Leu Val
                340                 345                 350
Asp Ile Gly Phe Ala Ala Tyr Asn Phe Val Glu Ser Ile Ile Asn Leu
            355                 360                 365
Phe Gln Val Val His Asn Ser Tyr Asn Arg Pro Ala Tyr Ser Pro Gly
            370                 375                 380
His Lys Thr Gln Pro Phe Leu Pro Trp Asp Ile Val Met Thr Gln Ser
385                 390                 395                 400
His Lys Phe Met Ser Thr Ser Val Gly Asp Arg Val Ser Ile Ile Cys
                405                 410                 415
Lys Ala Ser Gln Asp Val Gly Thr Ala Val Asp Trp Tyr Gln Gln Lys
            420                 425                 430
Pro Gly Gln Ser Pro Lys Leu Leu Ile Tyr Trp Ala Ser Thr Arg His
            435                 440                 445
Thr Gly Val Pro Asp Arg Phe Thr Gly Ser Gly Ser Gly Thr Asp Phe
450                 455                 460
Thr Leu Thr Ile Thr Asn Val Gln Ser Glu Asp Leu Ala Asp Tyr Phe
465                 470                 475                 480
Cys Gln Gln Tyr Asn Ser Tyr Pro Leu Thr Phe Gly Ala Gly Thr Met
                485                 490                 495
Leu Asp Leu Lys Gly Gly Gly Ser Glu Val Gln Leu Gln Gln Ser
            500                 505                 510
Gly Pro Glu Leu Lys Lys Pro Gly Thr Ser Val Arg Ile Ser Cys Lys
            515                 520                 525
Thr Ser Gly Tyr Thr Phe Thr Glu Tyr Thr Ile His Trp Val Lys Gln
            530                 535                 540
Ser His Gly Lys Ser Leu Glu Trp Ile Gly Asn Ile Asn Pro Asn Asn
545                 550                 555                 560
Gly Gly Thr Thr Tyr Asn Gln Lys Phe Glu Asp Lys Ala Thr Leu Thr
                565                 570                 575
Val Asp Lys Ser Ser Ser Thr Ala Tyr Met Glu Leu Arg Ser Leu Thr
            580                 585                 590
Ser Glu Asp Ser Ala Val Tyr Tyr Cys Ala Ala Gly Trp Asn Phe Asp
            595                 600                 605
```

Tyr Trp Gly Gln Gly Thr Thr Leu Thr Val Ser Ser Gly Gly Gly
            610                 615                 620

Ser Gly Gly Gly Gly Ser Gly Gly Gly Gly Ser Asp Ile Val Met Thr
625                 630                 635                 640

Gln Ser His Lys Phe Met Ser Thr Ser Val Gly Asp Arg Val Ser Ile
                645                 650                 655

Ile Cys Lys Ala Ser Gln Asp Val Gly Thr Ala Val Asp Trp Tyr Gln
            660                 665                 670

Gln Lys Pro Gly Gln Ser Pro Lys Leu Leu Ile Tyr Trp Ala Ser Thr
        675                 680                 685

Arg His Thr Gly Val Pro Asp Arg Phe Thr Gly Ser Gly Ser Gly Thr
            690                 695                 700

Asp Phe Thr Leu Thr Ile Thr Asn Val Gln Ser Glu Asp Leu Ala Asp
705                 710                 715                 720

Tyr Phe Cys Gln Gln Tyr Asn Ser Tyr Pro Leu Thr Phe Gly Ala Gly
                725                 730                 735

Thr Met Leu Asp Leu Lys Gly Gly Gly Gly Ser Glu Val Gln Leu Gln
            740                 745                 750

Gln Ser Gly Pro Glu Leu Lys Lys Pro Gly Thr Ser Val Arg Ile Ser
        755                 760                 765

Cys Lys Thr Ser Gly Tyr Thr Phe Thr Glu Tyr Thr Ile His Trp Val
770                 775                 780

Lys Gln Ser His Gly Lys Ser Leu Glu Trp Ile Gly Asn Ile Asn Pro
785                 790                 795                 800

Asn Asn Gly Gly Thr Thr Tyr Asn Gln Lys Phe Glu Asp Lys Ala Thr
                805                 810                 815

Leu Thr Val Asp Lys Ser Ser Ser Thr Ala Tyr Met Glu Leu Arg Ser
            820                 825                 830

Leu Thr Ser Glu Asp Ser Ala Val Tyr Tyr Cys Ala Ala Gly Trp Asn
        835                 840                 845

Phe Asp Tyr Trp Gly Gln Gly Thr Thr Leu Thr Val Ser Ser
850                 855                 860

<210> SEQ ID NO 13
<211> LENGTH: 2595
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 13
gctggtgctg acgacgtcgt cgactcctcc aagtccttcg tcatggagaa cttcgcttcc      60
taccacggga ccaagccagg ttacgtcgac tccatccaga agggtatcca gaagccaaag     120
tccggcaccc aagtaactac gacgacgac tggaagggt tctactccac cgacaacaag      180
tacgacgctg cgggatactc tgtagataat gaaaacccgc tctctggaaa agctggaggc     240
gtggtcaagg tcacctaccc aggtctgact aaggtcttgg ctttgaaggt cgacaacgct     300
gagaccatca gaaggagtt gggtttgtcc ttgactgagc cattgatgga gcaagtcggt     360
accgaagagt tcatcaagag attcggtgac ggtgcttcca gagtcgtctt gtccttgcca     420
ttcgctgagg ttcttctag cgttgaatat attaataact gggaacaggc taaggctttg     480
tctgttgaat tggagattaa cttcgaaacc agaggtaaga gaggtcaaga tgcgatgtat     540
gagtatatgg ctcaagcctg tgctggtaac agagtcagac gttctgttgg ttcctctttg     600

```
tcctgtatca acctagactg ggacgtcatc agagacaaga ctaagaccaa gatcgagtct      660
ttgaaagagc atggcccaat caagaacaag atgtccgaat cccccgctaa gaccgtctcc      720
gaggaaaagg ccaagcaata cctagaagag ttccaccaaa ccgccttgga gcatcctgaa      780
ttgtcagaac ttaaaaccgt tactgggacc aatcctgtat tcgctggggc taactatgcg      840
gcgtgggcag taaacgttgc gcaagttatc gatagcgaaa cagctgataa tttggaaaag      900
acaactgctg ctctttcgat acttcctggt atcggtagcg taatgggcat tgcagacggt      960
gccgttcacc acaatacaga agagatagtg gcacaatcca tcgctttgtc ctctttgatg     1020
gttgctcaag ctatcccatt ggtcggtgag ttggttgaca tcggtttcgc tgcctacaac     1080
ttcgtcgagt ccatcatcaa cttgttccaa gtcgtccaca actcctacaa ccgtccggct     1140
tactccccag gtcacaagac ccaaccattc ttgccatggc catgggatat tgttatgact     1200
caatctcata agttcatgtc cacttccgtc ggtgatagag tctctattat ttgtaaggct     1260
tctcaggacg tcggtactgc tgttgattgg tatcaacaaa agccaggtca atctccaaag     1320
ttgttgattt actgggcttc tactagacat actggtgttc cagatagatt cactggttct     1380
ggttctggta ctgatttcac cttgactatc actaacgtcc agtctgagga cttggctgac     1440
tacttctgcc agcagtacaa ctcttaccca ttgactttcg gtgctggaac catgttggat     1500
ttgaagggtg gaggtggatc tgaggtccag ttgcagcaat ctggaccaga gttgaagaag     1560
ccaggtactt ctgtcagaat ttcttgtaag acttctggtt acactttcac tgagtacact     1620
attcattggg ttaagcaatc tcatggtaag tcttttggagt ggattggaaa catcaaccca     1680
aacaacggtg aactaccta caaccaaaag ttcgaggata aggctacttt gactgttgat     1740
aagtcttctt ccactgctta catggaattg agatccttga cctctgagga ttccgctgtc     1800
tactactgtg ctgctggttg gaacttcgat tactggggac aaggaaccac tttgactgtt     1860
tcctctggag gtggcgggtc tggtggaggc ggatccggag gtggcggatc tgatattgtt     1920
atgactcaat ctcataagtt catgtccact tccgtcggtg atagagtctc tattatttgt     1980
aaggcttctc aggacgtcgg tactgctgtt gattggtatc aacaaaagcc aggtcaatct     2040
ccaaagttgt tgatttactg ggcttctact agacatactg tgttccaga tagattcact     2100 ggttctggtt ctggtactga tttcaccttg actatcacta acgtccagtc tgaggacttg     2160
gctgactact ctgccagca gtacaactct tacccattga ctttcggtgc tggaaccatg     2220
ttggatttga ggtggagg tggatctgag gtccagttgc agcaatctgg accagagttg     2280
aagaagccag gtacttctgt cagaatttct tgtaagactt ctggttacac tttcactgag     2340
tacactattc attgggttaa gcaatctcat ggtaagtctt tggagtggat tggaaacatc     2400
aacccaaaca acggtggaac tacctacaac caaaagttcg aggataaggc tactttgact     2460
gttgataagt cttcttccac tgcttacatg gaattgagat ccttgacctc tgaggattcc     2520
gctgtctact actgtgctgc tggttggaac ttcgattact ggggacaagg aaccactttg     2580
actgtttcct cttaa                                                       2595
```

<210> SEQ ID NO 14
<211> LENGTH: 1512
<212> TYPE: DNA
<213> ORGANISM: Artificial Sequence
<220> FEATURE:
<223> OTHER INFORMATION: Description of Artificial Sequence; note = synthetic construct

<400> SEQUENCE: 14

```
ggtggaggtg gctctgactt tgttatgtct caatctccat cctccttggc tgtttctgtt    60
ggtgagaggg ttactatgtc ttgtaagtcc tctcaatctt tgttgtactt ttctaaccga   120
aagaactact tggcttggta ccaacaaaag ccaggtcaat ctcctaagtt gttgattaac   180
tgggcttcca ccagagaatc tggtgtccct gacagattca ctggttctgg ttctagaact   240
gacttcactt tgaccatctc ttctgttaag gctgaagact tggctgttta cttctgtcaa   300
caattctact cttaccctcc aactttcggt ggtggtacca agttggaaat caagggtggc   360
ggaggttccc aagtccaatt gcaacaatct gaagctgaat ggctagacc tggtgcttct   420
gttaagatgt cctgtaaggc ttctggttac accttcactg actacactat ccactggttg   480
aggcaaaaac ctggtcaagg tttggactgg attggttact caacccttc ttctggatct   540
actgaataca acagaaagtt caaggacaga accattttga ctgctgacag atcctctacc   600
actgtttaca tgcaattgtc ttctttgact tctgaggact ctgctgtcta ctactgtgct   660
agaaagggtg agaagttgtt gggtaacaga tactggtact cgacgtctg gggtgctggt   720
acctctgtca ccgtctcctc tggaggcgga ggcagcggag gcggtggatc cggagggga   780
ggctcggact tgttatgtc tcaatctcca tcctccttgg ctgtttctgt tggtgagagg   840
gttactatgt cttgtaagtc ctctcaatct tgttgtact tttctaaccg aaagaactac   900
ttggcttggt accaacaaaa gccaggtcaa tctcctaagt tgttgattaa ctgggcttcc   960
accagagaat ctggtgtccc tgacagattc actggttctg gttctagaac tgacttcact  1020
ttgaccatct cttctgttaa ggctgaagac ttggctgttt acttctgtca acaattctac  1080
tcttaccctc aactttcgg tggtggtacc aagttggaaa tcaagggtgg cggaggttcc  1140
caagtccaat tgcaacaatc tgaagctgaa ttggctagac ctggtgcttc tgttaagatg  1200
tcctgtaagg cttctggtta caccttcact gactacacta tccactggtt gaggcaaaaa  1260
cctggtcaag gtttggactg gattggttac ttcaacccct tcttctggat ctactgaatac  1320
aacagaaagt tcaaggacag aaccattttg actgctgaca gatcctctac cactgtttac  1380
atgcaattgt cttctttgac ttctgaggac tctgctgtct actactgtgc tagaaagggt  1440
gagaagttgt tgggtaacag atactggtac ttcgacgtct ggggtgctgg tacctctgtc  1500
accgtctcct ct                                                      1512
```

<210> SEQ ID NO 15
<211> LENGTH: 504
<212> TYPE: PRT
<213> ORGANISM: Artificial Sequence
<220> FEATURE:
<223> OTHER INFORMATION: Description of Artificial Sequence; note = synthetic construct

<400> SEQUENCE: 15

```
Gly Gly Gly Gly Ser Asp Phe Val Met Ser Gln Ser Pro Ser Ser Leu
1               5                   10                  15

Ala Val Ser Val Gly Glu Arg Val Thr Met Ser Cys Lys Ser Ser Gln
            20                  25                  30

Ser Leu Leu Tyr Phe Ser Asn Arg Lys Asn Tyr Leu Ala Trp Tyr Gln
        35                  40                  45

Gln Lys Pro Gly Gln Ser Pro Lys Leu Leu Ile Asn Trp Ala Ser Thr
    50                  55                  60

Arg Glu Ser Gly Val Pro Asp Arg Phe Thr Gly Ser Gly Ser Arg Thr
65                  70                  75                  80
```

```
Asp Phe Thr Leu Thr Ile Ser Ser Val Lys Ala Glu Asp Leu Ala Val
                85                  90                  95

Tyr Phe Cys Gln Gln Phe Tyr Ser Tyr Pro Pro Thr Phe Gly Gly Gly
            100                 105                 110

Thr Lys Leu Glu Ile Lys Gly Gly Gly Gly Ser Gln Val Gln Leu Gln
        115                 120                 125

Gln Ser Glu Ala Glu Leu Ala Arg Pro Gly Ala Ser Val Lys Met Ser
    130                 135                 140

Cys Lys Ala Ser Gly Tyr Thr Phe Thr Asp Tyr Thr Ile His Trp Leu
145                 150                 155                 160

Arg Gln Lys Pro Gly Gln Gly Leu Asp Trp Ile Gly Tyr Phe Asn Pro
                165                 170                 175

Ser Ser Gly Ser Thr Glu Tyr Asn Arg Lys Phe Lys Asp Arg Thr Ile
            180                 185                 190

Leu Thr Ala Asp Arg Ser Ser Thr Thr Val Tyr Met Gln Leu Ser Ser
        195                 200                 205

Leu Thr Ser Glu Asp Ser Ala Val Tyr Tyr Cys Ala Arg Lys Gly Glu
    210                 215                 220

Lys Leu Leu Gly Asn Arg Tyr Trp Tyr Phe Asp Val Trp Gly Ala Gly
225                 230                 235                 240

Thr Ser Val Thr Val Ser Ser Gly Gly Gly Ser Gly Gly Gly Gly
                245                 250                 255

Ser Gly Gly Gly Gly Ser Asp Phe Val Met Ser Gln Ser Pro Ser Ser
            260                 265                 270

Leu Ala Val Ser Val Gly Glu Arg Val Thr Met Ser Cys Lys Ser Ser
        275                 280                 285

Gln Ser Leu Leu Tyr Phe Ser Asn Arg Lys Asn Tyr Leu Ala Trp Tyr
    290                 295                 300

Gln Gln Lys Pro Gly Gln Ser Pro Lys Leu Leu Ile Asn Trp Ala Ser
305                 310                 315                 320

Thr Arg Glu Ser Gly Val Pro Asp Arg Phe Thr Gly Ser Gly Ser Arg
                325                 330                 335

Thr Asp Phe Thr Leu Thr Ile Ser Ser Val Lys Ala Glu Asp Leu Ala
            340                 345                 350

Val Tyr Phe Cys Gln Gln Phe Tyr Ser Tyr Pro Pro Thr Phe Gly Gly
        355                 360                 365

Gly Thr Lys Leu Glu Ile Lys Gly Gly Gly Gly Ser Gln Val Gln Leu
    370                 375                 380

Gln Gln Ser Glu Ala Glu Leu Ala Arg Pro Gly Ala Ser Val Lys Met
385                 390                 395                 400

Ser Cys Lys Ala Ser Gly Tyr Thr Phe Thr Asp Tyr Thr Ile His Trp
                405                 410                 415

Leu Arg Gln Lys Pro Gly Gln Gly Leu Asp Trp Ile Gly Tyr Phe Asn
            420                 425                 430

Pro Ser Ser Gly Ser Thr Glu Tyr Asn Arg Lys Phe Lys Asp Arg Thr
        435                 440                 445

Ile Leu Thr Ala Asp Arg Ser Ser Thr Thr Val Tyr Met Gln Leu Ser
    450                 455                 460

Ser Leu Thr Ser Glu Asp Ser Ala Val Tyr Tyr Cys Ala Arg Lys Gly
465                 470                 475                 480

Glu Lys Leu Leu Gly Asn Arg Tyr Trp Tyr Phe Asp Val Trp Gly Ala
                485                 490                 495

Gly Thr Ser Val Thr Val Ser Ser
```

-continued

<210> SEQ ID NO 16
<211> LENGTH: 345
<212> TYPE: DNA
<213> ORGANISM: Artificial Sequence
<220> FEATURE:
<223> OTHER INFORMATION: Description of Artificial Sequence; note = synthetic construct

<400> SEQUENCE: 16

```
gaggtccaac tggtacagtc tggacctgaa gtgaagaagc ctggggctac agtgaagata      60
tcctgcaaga cttctggata cacattcact gaatatacca tacactgggt gaagcaggcc     120
cctggaaagg gccttgagtg gattggaaac atcaatccta caatggtgg taccacctac      180
aatcagaagt tcgaggacaa ggccacacta actgtagaca gtccaccga tacagcctac      240
atggagctca gcagcctaag atctgaggat actgcagtct attattgtgc agctggttgg     300
aactttgact actggggcca agggaccctg ctcaccgtct cctca                     345
```

<210> SEQ ID NO 17
<211> LENGTH: 115
<212> TYPE: PRT
<213> ORGANISM: Artificial Sequence
<220> FEATURE:
<223> OTHER INFORMATION: Description of Artificial Sequence; note = synthetic construct

<400> SEQUENCE: 17

```
Glu Val Gln Leu Val Gln Ser Gly Pro Glu Val Lys Lys Pro Gly Ala
 1               5                  10                  15

Thr Val Lys Ile Ser Cys Lys Thr Ser Gly Tyr Thr Phe Thr Glu Tyr
                20                  25                  30

Thr Ile His Trp Val Lys Gln Ala Pro Gly Lys Gly Leu Glu Trp Ile
            35                  40                  45

Gly Asn Ile Asn Pro Asn Asn Gly Gly Thr Thr Tyr Asn Gln Lys Phe
        50                  55                  60

Glu Asp Lys Ala Thr Leu Thr Val Asp Lys Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Leu Thr
            100                 105                 110

Val Ser Ser
        115
```

<210> SEQ ID NO 18
<211> LENGTH: 115
<212> TYPE: PRT
<213> ORGANISM: Artificial Sequence
<220> FEATURE:
<223> OTHER INFORMATION: Description of Artificial Sequence; note = synthetic construct

<400> SEQUENCE: 18

```
Glu Val Gln Leu Gln Gln Ser Gly Pro Glu Leu Lys Lys Pro Gly Thr
 1               5                  10                  15

Ser Val Arg Ile Ser Cys Lys Thr Ser Gly Tyr Thr Phe Thr Glu Tyr
                20                  25                  30

Thr Ile His Trp Val Lys Gln Ser His Gly Lys Ser Leu Glu Trp Ile
            35                  40                  45
```

```
Gly Asn Ile Asn Pro Asn Asn Gly Gly Thr Thr Tyr Asn Gln Lys Phe
         50                  55                  60

Glu Asp Lys Ala Thr Leu Thr Val Asp Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Ala Gly Trp Asn Phe Asp Tyr Trp Gly Gln Gly Thr Thr Leu Thr
            100                 105                 110

Val Ser Ser
        115

<210> SEQ ID NO 19
<211> LENGTH: 345
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 19
gaggtccagt tgcagcaatc tggaccagag ttgaagaagc caggtacttc tgtcagaatt      60
tcttgtaaga cttctggtta cactttcact gagtacacta ttcattgggt taagcaatct    120
catggtaagt ctttggagtg gattggaaac atcaacccaa caacggtgg aactacctac     180 aaccaaaagt tcgaggataa ggctactttg actgttgata agtcttcttc cactgcttac    240
atggaattga gatccttgac ctctgaggat tccgctgtct actactgtgc tgctggttgg    300
aacttcgatt actggggaca aggaaccact ttgactgttt cctct                    345

<210> SEQ ID NO 20
<211> LENGTH: 321
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 20
gacatccaga tgacccagtc tccctcatcc ctgtccacat cagtaggaga cagggtcacc      60
ctcacctgta aggccagtca agatgtgggt actgctgtag actggtatca acagaaacca    120
ggaccatctc ctaaaactact gatttattgg gcatccactc ggcacactgg aatccctagt    180
cgcttctcag gcagtggatc tgggacagac ttcactctca ccatttctag tcttcagcct    240
gaagactttg cagattatta ctgtcagcaa tataacagct atcctctcac gttcggtcct    300
gggaccaagg tggacatcaa a                                              321

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 21

Asp Ile Gln Met Thr Gln Ser Pro Ser Ser Leu Ser Thr Ser Val Gly
  1               5                  10                  15

Asp Arg Val Thr Leu Thr Cys Lys Ala Ser Gln Asp Val Gly Thr Ala
                 20                  25                  30
```

-continued

```
Val Asp Trp Tyr Gln Gln Lys Pro Gly Pro Ser Pro Lys Leu Leu Ile
            35                  40                  45

Tyr Trp Ala Ser Thr Arg His Thr Gly Ile Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Asp Tyr Tyr Cys Gln Gln Tyr Asn Ser Tyr Pro Leu
                 85                  90                  95

Thr Phe Gly Pro Gly Thr Lys Val Asp Ile Lys
            100                 105
```

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence; note = synthetic construct

<400> SEQUENCE: 22

```
Asp Ile Val Met Thr Gln Ser His Lys Phe Met Ser Thr Ser Val Gly
 1               5                  10                  15

Asp Arg Val Ser Ile Ile Cys Lys Ala Ser Gln Asp Val Gly Thr Ala
                 20                  25                  30

Val Asp Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Thr Asn Val Gln Ser
 65                  70                  75                  80

Glu Asp Leu Ala Asp Tyr Phe Cys Gln Gln Tyr Asn Ser Tyr Pro Leu
                 85                  90                  95

Thr Phe Gly Ala Gly Thr Met Leu Asp Leu Lys
            100                 105
```

<210> SEQ ID NO 23
<211> LENGTH: 321
<212> TYPE: DNA
<213> ORGANISM: Artificial Sequence
<220> FEATURE:
<223> OTHER INFORMATION: Description of Artificial Sequence; note = synthetic construct

<400> SEQUENCE: 23

```
gatattgtta tgactcaatc tcataagttc atgtccactt ccgtcggtga tagagtctct      60
attatttgta aggcttctca ggacgtcggt actgctgttg attggtatca acaaaagcca     120
ggtcaatctc caaagttgtt gatttactgg gcttctacta gacatactgg tgttccagat     180
agattcactg gttctggttc tggtactgat ttcaccttga ctatcactaa cgtccagtct     240
gaggacttgg ctgactactt ctgccagcag tacaactctt acccattgac tttcggtgct     300
ggaaccatgt tggatttgaa g                                               321
```

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide cleavage site

<400> SEQUENCE: 24

-continued

```
Arg Val Arg Arg Ser Val
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide cleavage site

<400> SEQUENCE: 25

Gly Pro Leu Gly Met Leu Ser Gln
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide cleavage site

<400> SEQUENCE: 26

His Ser Ser Lys Leu Gln
1               5
```